(12) United States Patent
Oh

(10) Patent No.: US 10,918,625 B2
(45) Date of Patent: Feb. 16, 2021

(54) USE OF SESQUITERPENE DERIVATIVE

(71) Applicant: KOOKMIN UNIVERSITY INDUSTRY ACADEMY COOPERATION FOUNDATION, Seoul (KR)

(72) Inventor: Sangtaek Oh, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 16/686,940

(22) Filed: Nov. 18, 2019

(65) Prior Publication Data

US 2020/0078338 A1 Mar. 12, 2020

Related U.S. Application Data

(63) Continuation of application No. 16/301,583, filed as application No. PCT/KR2016/011558 on Oct. 14, 2016, now abandoned.

(30) Foreign Application Priority Data

Jul. 7, 2016 (KR) ........................ 10-2016-0086331

(51) Int. Cl.

| | | |
|---|---|---|
| *A61K 31/423* | (2006.01) | |
| *A61K 31/122* | (2006.01) | |
| *A61K 31/136* | (2006.01) | |
| *A23L 33/10* | (2016.01) | |
| *A61P 27/02* | (2006.01) | |
| *A61K 31/145* | (2006.01) | |
| *A61K 31/196* | (2006.01) | |
| *A61K 31/235* | (2006.01) | |
| *A61K 31/4184* | (2006.01) | |
| *A61K 9/00* | (2006.01) | |
| *A61K 31/015* | (2006.01) | |
| *A61K 9/06* | (2006.01) | |

(52) U.S. Cl.
CPC .......... *A61K 31/423* (2013.01); *A23L 33/10* (2016.08); *A61K 9/00* (2013.01); *A61K 9/06* (2013.01); *A61K 31/015* (2013.01); *A61K 31/122* (2013.01); *A61K 31/136* (2013.01); *A61K 31/145* (2013.01); *A61K 31/196* (2013.01); *A61K 31/235* (2013.01); *A61K 31/4184* (2013.01); *A61P 27/02* (2018.01); *A23V 2002/00* (2013.01)

(58) Field of Classification Search
CPC ... A61K 31/423; A61K 31/122; A61K 31/136
See application file for complete search history.

(56) References Cited

U.S. PATENT DOCUMENTS

| | | | |
|---|---|---|---|
| 5,744,623 A | 4/1998 | Gravalos et al. | |
| 2002/0012703 A1* | 1/2002 | Singh | A61K 31/203 |
| | | | 424/488 |
| 2009/0074795 A1 | 3/2009 | Farjo | |
| 2020/0078338 A1* | 3/2020 | Oh | A61K 31/235 |

FOREIGN PATENT DOCUMENTS

| | | |
|---|---|---|
| EP | 0731078 B1 | 3/2002 |
| KR | 1010593210000 | 8/2011 |
| KR | 10-1692378 | 1/2017 |
| KR | 10-1800346 | 11/2017 |
| WO | 2015108787 | 7/2015 |

OTHER PUBLICATIONS

Kim et al., "Wnt5a attenuates the pathogenic effects of the Wnt/β-catenin pathway in human retinal pigment epithelial cells via down-regulating β-catenin and Snail", BMB Rep. (2015), 48(9), pp. 525-530.
Ji et al., "Increased Levels of Dickkopf 3 in the Aqueous Humor of Patients With Diabetic Macular Edema", IOVS (Apr. 2016), vol. 57, No. 4, pp. 2296-2304.
Park et al., "Ilimaquinone and Ethylsmenoquinone, Marine Sponge Metabolites, Suppress the Proliferation of Multiple Myeloma Cells by Down-Regulating the Level of β-catenin", Mar. Drugs (2014), 12, pp. 3231-3244.
Senthilkumar et al., "Antiangiogenic effects of marine sponge derived compounds on cancer", Environmental Toxicology and Pharmacology (2013), 36, pp. 1097-1108.
Kong et al, "Antiproliferative and Antiangiogenic Activities of Smenospongine, a Marine Sponge Sesquiterpene Aminoquinone", Mar. Drugs. (2011), 9, pp. 154-161.
Riguera, "Isolating bioactive compounds from marine organisms", J Mar Biotechnol (1997), 5, pp. 187-193.
Kissau et al., "Develpopment of Natural Product-Derived Receptor Tyrosine Kinase Inhibitors Based on Conservation of Protein Domain Fold", J. Med. Chem, 2003, vol. 46, No. 14, pp. 2917-2931.

(Continued)

*Primary Examiner* — Matthew P Coughlin
(74) *Attorney, Agent, or Firm* — Duane Morris LLP; Gregory M. Lefkowitz; Jason M. Nolan

(57) ABSTRACT

The present disclosure relates to a novel use of a sesquiterpene derivative, more particularly to a composition for preventing, improving or treating macular degeneration or macular edema caused by vascular leakage in the eye, the composition containing a sesquiterpene derivative compound represented by Chemical Formula 1 of the present disclosure or a pharmaceutically acceptable salt thereof as an active ingredient. Whereas the intraocular disease-related treating agents available in the market should be injected directly into the vitreous cavity, thus causing pain and side effects, the sesquiterpene derivative compound of the present disclosure is delivered to the target tissue (eye) via different administration routes (oral, intraperitoneal, etc.) other than the intravitreal route. Accordingly, the sesquiterpene derivative compound provides excellent therapeutic effect without being restricted by the administration routes.

14 Claims, 3 Drawing Sheets

(56) References Cited

OTHER PUBLICATIONS

Daletos et al., "Cytotoxic and Protein Kinase Inhibiting Nakijiquinones and Nakijiquinols from the Sponge Dactylospongia metachromia", Journal of Natural Products, 2014, vol. 77, pp. 218-226.

Huang et al., "Blockade of VEGFR1 and 2 Suppresses Pathological Angiogenesis and Vascular Leakage in the Eye", PLoS ONE, Jun. 2011, vol. 5, Issue 6, e21411.

Loya et al., "Illimaquinone, a Selective Inhibitor of the RNase H Activity of Human Immunodeficiency Virus Type 1 Reverse Transcriptase", Antimicrobial Agents and Chemotherapy, Oct. 1990, vol. 34, No. 10, pp. 2009-2012.

Hwang et al., "Cytotoxic activity of rearranged drimane meroterpenoids against colon cancer cells via down-regulartion of β-catenin expression", J. Nat. Prod. 2015, vol. 78, pp. 453-461.

Chen et al., "Activation of the Wnt pathway plays a pathogenic role in diabetic retinopathy in humans and animal models", 2009, The American Journal of Pathology, vol. 175, No. 6, pp. 2676-2685.

Guo et al., "Matrigel and activin a promote cell-cell contact and anti-apoptotic activity in cultured human retinal pigment epithelium cells", 2016, Experimental Eye Research, vol. 147, pp. 37-49.

\* cited by examiner

USE OF SESQUITERPENE DERIVATIVE

CROSS REFERENCE TO RELATED APPLICATIONS

This application is a continuation of U.S. application Ser. No. 16/301,583, filed Nov. 14, 2018, which is a U.S. National Phase of International Application No. PCT/KR2016/011558, filed Oct. 14, 2016, which claims priority to S. Korean Application KR 10-2016-0086331, filed Jul. 7, 2016, the entireties of which are incorporated herein by reference.

TECHNICAL FIELD

The present disclosure relates to a novel use of a sesquiterpene derivative, more particularly to a composition for preventing, improving or treating macular degeneration or macular edema caused by vascular leakage in the eye, the composition containing a sesquiterpene derivative compound represented by Chemical Formula 1 or a pharmaceutically acceptable salt thereof as an active ingredient.

BACKGROUND ART

Macular edema refers to the swelling of the macula lutea. The edema is caused by fluid leaking from the retinal blood vessel. Blood is leaked from weak blood vessel walls and flown into the macula lutea packed with retinal cones which sense color and are responsible for vision during the day. Then, images are blurred at the center or right side of the central region. The vision worsens gradually over several months. All age-related macular degeneration (AMD) is associated with macular edema. Vascular leakage in the eye occurs due to various causes. For example, continued increase in blood pressure in in hypertensive patients causes breakdown of the blood-retinal barrier and the damage to the blood-retinal barrier causes retinal edema due to vascular leakage. The macula lutea is often damaged by macula tumentia following the removal of the eye lens for treatment of cataract.

For treatment of macular edema, laser photocoagulation, vitrectomy or systemic, intravitreal or sub-Tenon of steroids, etc. have been employed. Laser photocoagulation alleviates macula tumentia by blocking the blood vessels where fluid leakage occurs. However, care should be taken to avoid the fovea when irradiating laser because it is extremely vulnerable. If the fovea is damaged during the operation, the central vision may be impaired. Also, more than one laser treatments are often necessary to remove the swelling. Vitrectomy is employed when the laser treatment is ineffective, but this method is often associated with the high risk of tissue invasion which causes postoperative complications. The intravitreal administration of steroids may cause ocular hypertension, steroid-induced glaucoma and posterior subcapsular cataract. In addition, the intravitreal administration of steroids often cause postoperative complications.

In addition, other drugs administered directly into the vitreous cavity are known to require repeated administrations with 4-6 week intervals. The administration directly into the vitreous cavity also causes inconvenience of administration, pain and side effects.

The inventors of the present disclosure have researched to develop a medication exhibiting an excellent therapeutic effect for macular edema or macular degeneration related thereto, which reduces the inconvenience of administration and can be administered for a long time. In doing so, they have identified that a compound represented by Chemical Formula 1 exhibits therapeutic effect in a macular edema or macular degeneration animal model by effectively preventing vascular leakage in the eye and that the compound is targeted to the eye even when it is administered orally.

REFERENCES OF RELATED ART

Non-Patent Documents (Non-patent document 1) Joo-Hyun Kim et al., "Wnt5a attenuates the pathogenic effects of the Wnt/β-catenin pathway in human retinal pigment epithelial cells via down-regulating β-catenin and Snail", BMB Rep. 2015; 48(9): 525-530.

(Non-patent document 2) Bokjun Ji et al., "Increased Levels of Dickkopf 3 in the Aqueous Humor of Patients With Diabetic Macular Edema", Invest Ophthalmol Vis Sci. April 2016; 57; 2296-2304.

SUMMARY

The present disclosure is directed to providing a pharmaceutical composition for preventing or treating macular degeneration or macular edema caused by vascular leakage in the eye.

The present disclosure is also directed to providing a food composition for preventing or improving macular degeneration or macular edema caused by vascular leakage in the eye.

The above objects of the present disclosure can be achieved by the present disclosure as described below.

The present disclosure provides a pharmaceutical composition for preventing or treating macular degeneration or macular edema, which contains a compound represented by Chemical Formula 1 or a pharmaceutically acceptable salt thereof as an active ingredient:

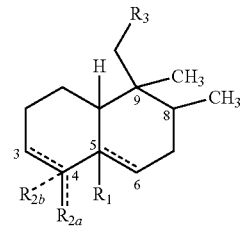

Chemical Formula 1 wherein the broken line denotes a single bond or a double bond, wherein i) if the bond between C-3 and C-4 and the bond between C-5 and C-6 are single bonds, $R_{2b}$ is nonexistent and $R_{2a}$ is $CH_2$;

ii) if the bond between C-3 and C-4 is a double bond, the bond between C-5 and C-6 is a single bond, $R_{2b}$ is nonexistent and $R_{2a}$ is $CH_3$; or iii) if the bond between C-5 and C-6 is a double bond, the bond between C-3 and C-4 is a single bond and $R_{2a}$ and $R_{2b}$ are $CH_3$, $R_1$ is H or $CH_3$, $R_3$ is a functional group selected from a group consisting of $R_{3a}$ through $R_{3d}$,

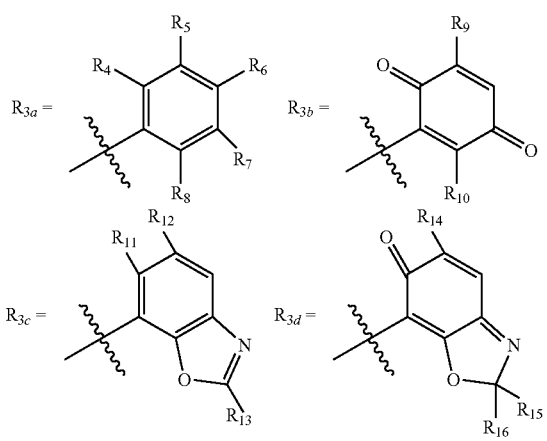

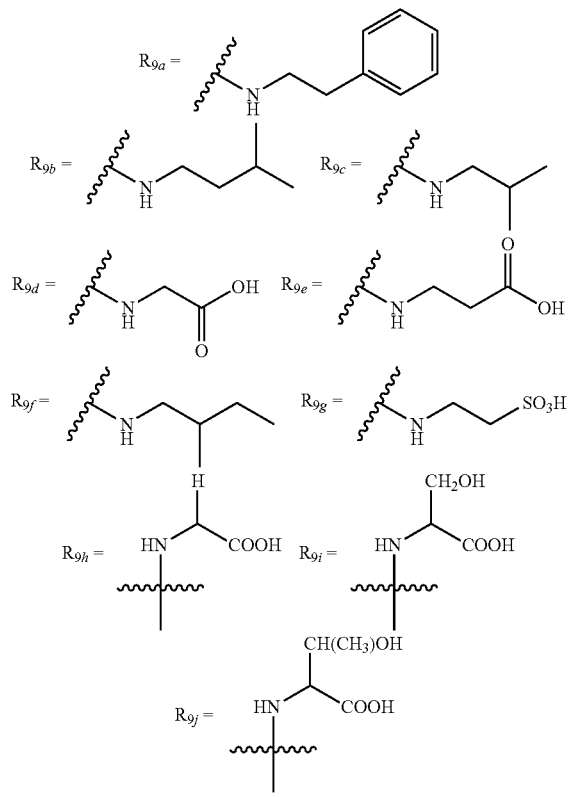

in $R_{1a}$,
i) each of $R_4$ and $R_7$ is OH or $OCH_3$ and $R_5$, $R_6$ and $R_8$ are H; or
ii) $R_5$ is $COOCH_3$, $R_7$ is H or OH, $R_8$ is OH and $R_4$ and $R_6$ are H,
in $R_{3b}$,
$R_9$ is a functional group selected from a group consisting of H, $NH_2$, $C_1$-$C_8$ alkoxy and $R_{9a}$ through $R_{9j}$ and $R_{10}$ is H or OH, in $R_{3c}$,
each of $R_{11}$ and $R_{12}$ is OH or OAc and $R_{13}$ is H; or
each of $R_{11}$ and $R_{12}$ is OH or $OCH_3$ and $R_{13}$ is $CH_3$ and
in $R_{3d}$,
$R_{14}$ is $OCH_3$ and $R_{15}$ and $R_{16}$ are $CH_3$.

The present disclosure also provides a pharmaceutical composition for inhibiting vascular leakage in the eye, which contains the compound represented by Chemical Formula 1 or a pharmaceutically acceptable salt thereof as an active ingredient The present disclosure also provides a food composition for preventing or improving macular degeneration or macular edema, which contains the compound represented by Chemical Formula 1 or a pharmaceutically acceptable salt thereof as an active ingredient.

BEST MODE

Figure 1:
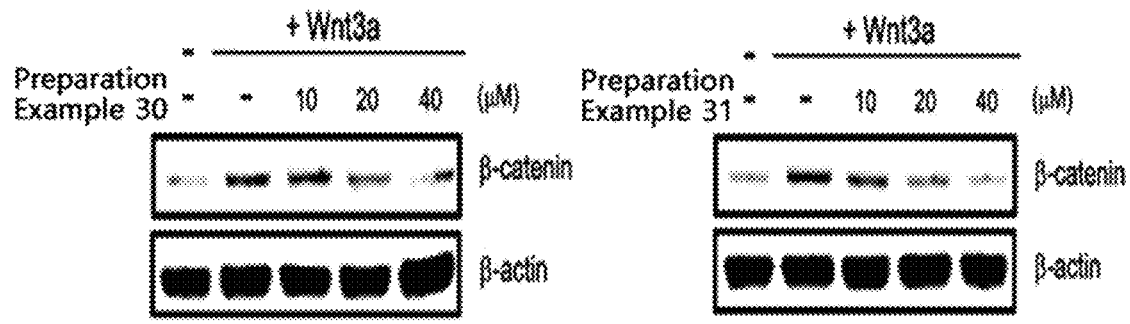
FIG. 1 shows a result of investigating the inhibitory effect of a compound of the present disclosure (Preparation Example 30 or Preparation Example 31) on β-catenin expression in HEK293 cells, in which the Wnt/β-catenin pathway is activated by treating with Wnt-3a CM, by western blot.

The inventors of the present disclosure have researched to develop a medication exhibiting an excellent therapeutic effect for macular edema or macular degeneration related thereto, which reduces the inconvenience of administration and can be administered for a long time. In doing so, they have identified that a compound represented by Chemical Formula 1 exhibits therapeutic effect for macular edema or macular degeneration diseases by effectively preventing vascular leakage in the eye, particularly in the retina.

Accordingly, in an aspect, the present disclosure relates to a pharmaceutical composition for preventing or treating macular degeneration or macular edema, which contains a compound represented by Chemical Formula 1 or a pharmaceutically acceptable salt thereof as an active ingredient.

Chemical Formula 1

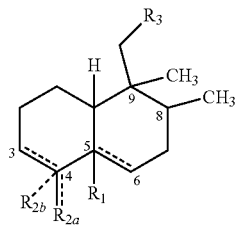

wherein
the broken line denotes a single bond or a double bond,
wherein
i) if the bond between C-3 and C-4 and the bond between C-5 and C-6 are single bonds, $R_{2b}$ is nonexistent and $R_{2a}$ is $CH_2$;
ii) if the bond between C-3 and C-4 is a double bond, the bond between C-5 and C-6 is a single bond, $R_{2b}$ is nonexistent and $R_{2a}$ is $CH_3$; or
iii) if the bond between C-5 and C-6 is a double bond, the bond between C-3 and C-4 is a single bond and $R_{2a}$ and $R_{2b}$ are $CH_3$,
$R_1$ is H or $CH_3$,
$R_3$ is a functional group selected from a group consisting of $R_{3a}$ through $R_{3d}$,

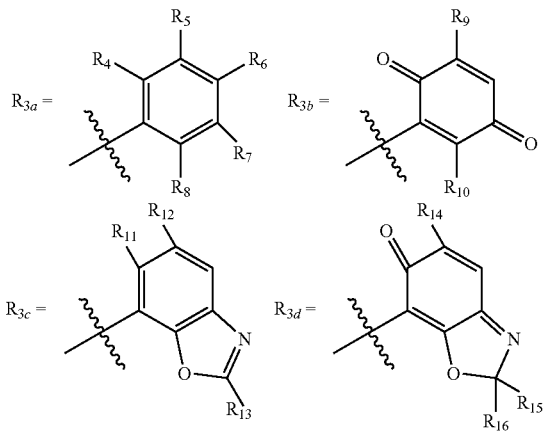

in $R_{3a}$,
i) each of $R_4$ and $R_7$ is OH or $OCH_3$ and $R_5$, $R_6$ and $R_8$ are H; or
ii) $R_5$ is $COOCH_3$, $R_7$ is H or OH, $R_8$ is OH and $R_4$ and $R_6$ are H,
in $R_{3b}$,
$R_9$ is a functional group selected from a group consisting of H, $NH_2$, $C_1$-$C_8$ alkoxy and $R_{9a}$ through $R_{9j}$ and $R_{10}$ is H or OH,

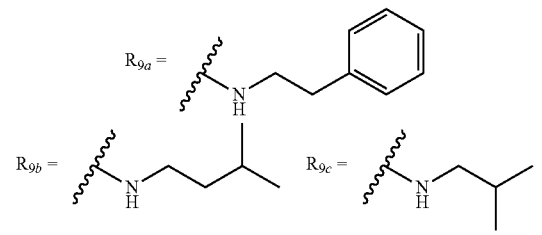

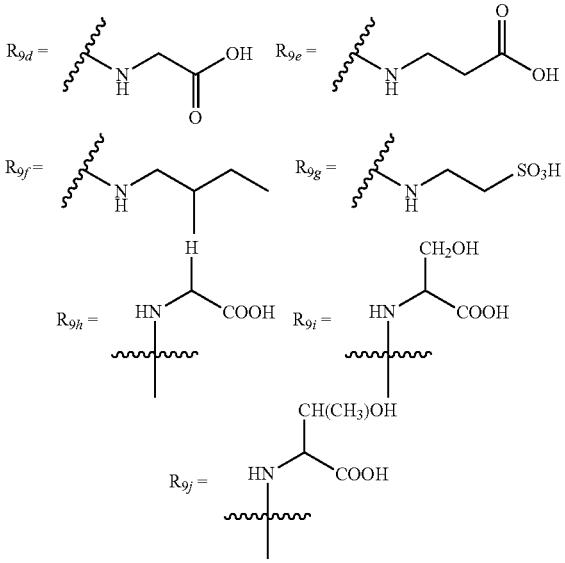

in $R_{1c}$,
each of $R_{11}$ and $R_{12}$ is OH or OAc and $R_{13}$ is H; or
each of $R_{11}$ and $R_{12}$ is OH or $OCH_3$ and $R_{13}$ is $CH_3$ and in $R_{3d}$,
$R_{14}$ is $OCH_3$ and $R_{15}$ and $R_{16}$ are $CH_3$.

In the present disclosure, the term alkoxy group refers to an alkyl group bonded to oxygen (O-alkyl group). In the present disclosure, the alkoxy group may be a $C_1$-$C_8$ alkoxy group selected from a group consisting of a methoxy group ($C_1$), an ethoxy group ($C_2$), a propoxy group ($C_3$), a butoxy group ($C_4$), a pentyloxy group ($C_5$), a hexyloxy group ($C_6$), a heptyloxy group ($C_7$) and an octyloxy group ($C_8$), although not being limited thereto. Specifically, the alkoxy group of the present disclosure may be a methoxy group or an ethoxy group.

In Chemical Formula 1,
i) the structure wherein, if the bond between C-3 and C-4 and the bond between C-5 and C-6 are single bonds, $R_{2b}$ is nonexistent and $R_{2a}$ is $CH_2$ may be represented by <Chemical Formula 1-1>;
ii) the structure wherein, if the bond between C-3 and C-4 is a double bond, the bond between C-5 and C-6 is a single bond, $R_{2b}$ is nonexistent and $R_{2a}$ is $CH_3$ may be represented by <Chemical Formula 1-2>; and
iii) the structure wherein, if the bond between C-5 and C-6 is a double bond, the bond between C-3 and C-4 is a single bond and $R_{2a}$ and $R_{2b}$ are $CH_3$ may be represented by <Chemical Formula 1-3>.

Chemical Formula 1-1

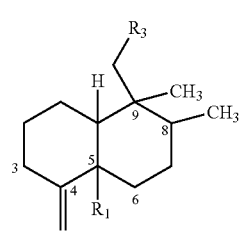

Chemical Formula 1-2

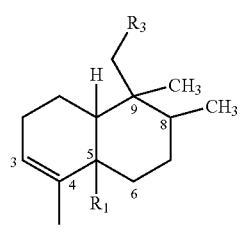

Chemical Formula 1-3

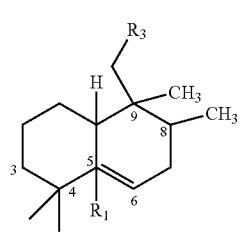

Specifically, the compound of the present disclosure of Chemical Formula 1 may be the compounds described in [Table 1], although not being limited thereto.

TABLE 1

| Preparation Example | Structure |
| --- | --- |
| 1 | <Chemical Formula 2> |
| 2 | <Chemical Formula 3> |

TABLE 1-continued

| Preparation Example | Structure |
| --- | --- |
| 3 | <Chemical Formula 4> |
| 4 | <Chemical Formula 5> |
| 5 | <Chemical Formula 6> |

TABLE 1-continued
| Preparation Example | Structure |
|---|---|
| 6 | <Chemical Formula 7> 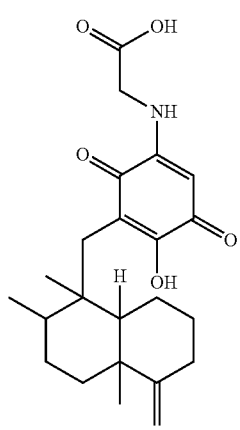 |
| 7 | <Chemical Formula 8> 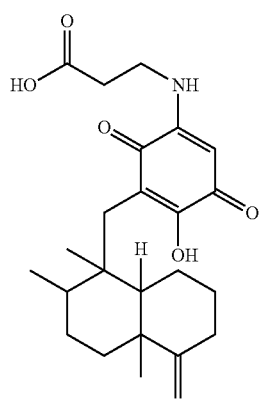 |
| 8 | <Chemical Formula 9> 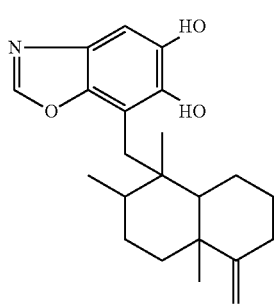 |
| 9 | <Chemical Formula 10> 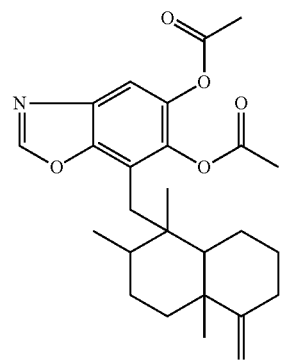 |
| 10 | <Chemical Formula 11> 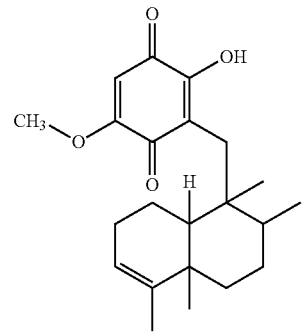 |
| 11 | <Chemical Formula 12> 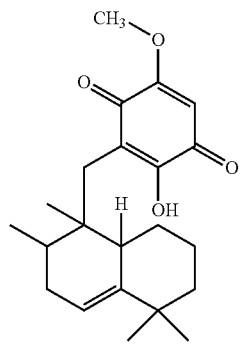 |
| 12 | <Chemical Formula 13> 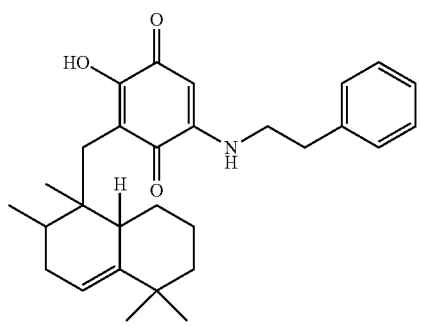 |

TABLE 1-continued
| Preparation Example | Structure |
| --- | --- |
| 13 | <Chemical Formula 14> 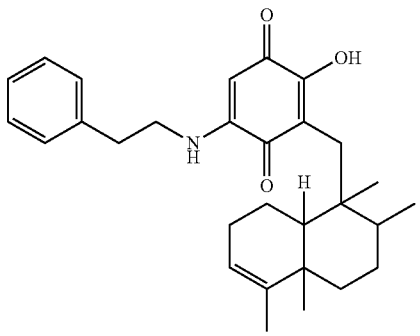 |
| 14 | <Chemical Formula 15> 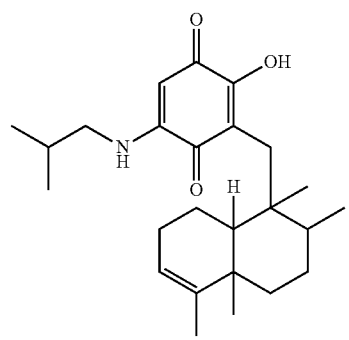 |
| 15 | <Chemical Formula 16> 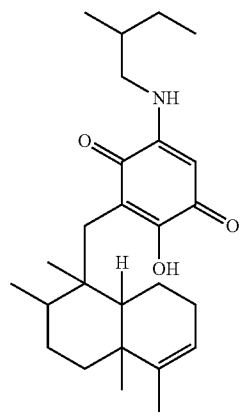 |
| 16 | <Chemical Formula 17> 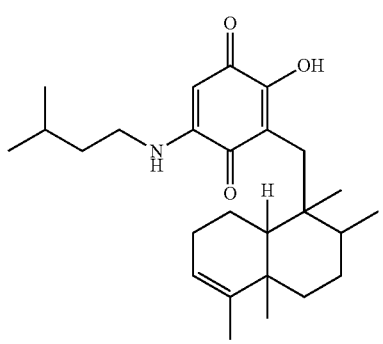 |
| 17 | <Chemical Formula 18> 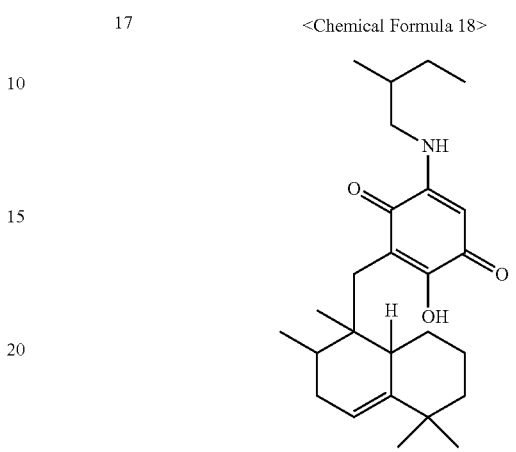 |
| 18 | <Chemical Formula 19> 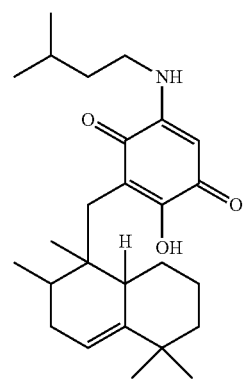 |
| 19 | <Chemical Formula 20> 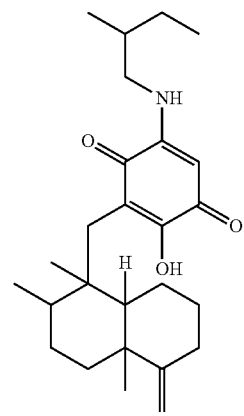 |

TABLE 1-continued

| Preparation Example | Structure |
|---|---|
| 20 | <Chemical Formula 21> |
| 21 | <Chemical Formula 22> |
| 22 | <Chemical Formula 23> |
| 23 | <Chemical Formula 24> |
| 24 | <Chemical Formula 25> |
| 25 | <Chemical Formula 26> |
| 26 | <Chemical Formula 27> |
| 27 | <Chemical Formula 28> |

TABLE 1-continued

| Preparation Example | Structure |
|---|---|
| 28 | <Chemical Formula 29> |
| 29 | <Chemical Formula 30> |
| 30 | <Chemical Formula 31> |
| 31 | <Chemical Formula 32> |
| 32 | <Chemical Formula 33> |
| 33 | <Chemical Formula 34> |
| 34 | <Chemical Formula 35> |

Specifically, the sesquiterpene derivative compound of the present disclosure may be one wherein, in Chemical Formula 1, if the bond between C-3 and C-4 and the bond between C-5 and C-6 are single bonds, $R_{2b}$ is nonexistent, $R_{2a}$ is $CH_2$ and $R_3$ is a functional group selected from a group consisting of $R_{3b}$ through $R_{3d}$.

Specifically, in $R_{3b}$, $R_9$ may be selected from a group consisting of ethoxy, methoxy and $R_{9a}$.

Specifically, in $R_{3c}$, $R_{11}$ may be OH, $R_{12}$ may be $OCH_3$ and $R_{13}$ may be $CH_3$.

Specifically, in $R_{3d}$, $R_{14}$ may be $OCH_3$ and $R_{15}$ and $R_{16}$ may be $CH_3$.

Most specifically, the compound of Chemical Formula 1 of the present disclosure may be a compound selected from a group consisting of:

3-[[(1R,2S,4aS,8aS)-1,2,4a-trimethyl-5-methylidene-3,4,6,7,8,8a-hexahydro-2H-naphthalen-1-yl]methyl]-4-hydroxy-5-(2-phenylethylamino)cyclohexa-3,5-diene-1,2-dione;

3-[[(1R,2S,4aS,8aS)-1,2,4a-trimethyl-5-methylidene-3,4,6,7,8,8a-hexahydro-2H-naphthalen-1-yl]methyl]-2-hydroxy-5-methoxycyclohexa-2,5-diene-1,4-dione;

3-[[(1S,2R,4aR,8aR)-1,2,4a-trimethyl-5-methylidene-3,4,6,7,8,8a-hexahydro-2H-naphthalen-1-yl]methyl]-5-ethoxy-2-hydroxycyclohexa-2,5-diene-1,4-dione;

18-methoxy-22-methyl-16-[{(5S,8S,9R,10S)-5,8,9-trimethyl-4-methylenedecahydronaphthalen-9-yl}methyl]benzo[d]-oxazol-17-ol; and 18-methoxy-22,22-dimethyl-16-[{(5R,8S,9R,10S)-5,8,9-trimethyl-4-methylenedecahydronaphthalen-9-yl}methyl]benzo[d]-oxazol-17(2H)-one.

The compound of Chemical Formula 1 of the present disclosure may be extracted from sponge. Specifically, the compound of Chemical Formula 1 for preventing or treating macular degeneration or macular edema caused by vascular leakage in the eye may be obtained by a method including a step of extracting one or more sponge selected from a group consisting of *Rhopaloeides* sp., *Spongia* sp., *Smenospongia* sp., *Hippospongia* sp., *Dactylospongia* sp., *Verongula* sp., *Dysidea* sp., sponge SS-1047, sponge SS-265 and sponge SS-1208 by adding a $C_1$-$C_6$ organic solvent.

The $C_1$-$C_6$ organic solvent may be selected from a group consisting of a $C_1$-$C_6$ alcohol (methanol, ethanol, propanol, butanol, pentanol, hexanol), acetone, an ether, benzene, chloroform, ethyl acetate, methylene chloride, hexane, cyclohexane, acetonitrile, dichloromethane and petroleum ether.

Specifically, the compound of the present disclosure of Chemical Formula 1 may be obtained by a method including: a step of extracting sponge by adding water, a $C_1$-$C_4$ alcohol or a mixture thereof as a solvent, thereby preparing a sponge extract; and a step of fractionating the extract by adding a second solvent and separating the same through chromatography.

As the chromatography, any one known to those skilled in the art can be used without limitation, including silica gel column chromatography, LH-20 column chromatography, ion-exchange chromatography, medium pressure liquid chromatography, thin-layer chromatography (TLC), silica gel vacuum liquid chromatography, high-performance liquid chromatography, etc.

The $C_1$-$C_4$ alcohol used to prepare the sponge extract may be selected from a group consisting of methanol, ethanol, propanol, isopropanol, butanol and isobutanol.

As the second solvent for fractionating the sponge extract, a $C_1$-$C_4$ alcohol, n-hexane, methylene chloride, acetone, chloroform, dichloromethane, ethyl acetate, acetonitrile or a mixture thereof may be used.

The compound of the present disclosure of Chemical Formula 1 includes a pharmaceutically acceptable salt thereof. In the present disclosure, the term 'pharmaceutically acceptable' means being physiologically acceptable and not causing allergic reactions such as gastroenteric trouble, dizziness, etc. or similar reactions when administered to human.

The pharmaceutically acceptable salt includes an acid addition salt with an inorganic acid or an organic acid. As the acid addition salt, an acid addition salt formed by a pharmaceutically acceptable free acid is useful. As the free acid, an inorganic acid or an organic acid may be used. As the inorganic acid, hydrochloric acid, bromic acid, sulfuric acid, phosphoric acid, etc. may be used. And, as the organic acid, citric acid, acetic acid, lactic acid, tartaric acid, fumaric acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholinoethanesulfonic acid, camphorsulfonic acid, 4-nitrobenzenesulfonic acid, hydroxy-O-sulfonic acid, 4-toluenesulfonic acid, galacturonic acid, embonic acid, glutamic acid, aspartic acid, etc. may be used.

In an example of the present disclosure, it was found out that the compound of the present disclosure of Chemical Formula 1 inhibits β-catenin in vitro, suggesting that it can inhibit vascular leakage by inhibiting the Wnt/β-catenin mechanism. In another example of the present disclosure, it was confirmed that the present disclosure compound exhibits therapeutic effect by inhibiting vascular leakage in a macular edema animal model in vivo. In addition, it was confirmed that it exhibits therapeutic effect regardless of administration routes because the compound was distributed in the target tissue (eye) even when it was administered through other administration routes (oral administration, intraperitoneal injection, etc.) rather than directly into the vitreous cavity.

Accordingly, in another aspect, the present disclosure relates to a pharmaceutical composition for inhibiting vascular leakage in the eye, which contains the compound of Chemical Formula 1 or a pharmaceutically acceptable salt thereof as an active ingredient.

In the present disclosure, the term 'vascular leakage' refers to the leakage of body fluid or blood plasma due to damage to the integrity of blood vessels. The vascular leakage in the eye constitutes the major pathological conditions of various eye diseases. In the present disclosure, the term 'vascular leakage in the eye' refers to vascular leakage in various tissues (choroid, retina, etc.) constituting the eye. Specifically, it may refer to vascular leakage in the retina, although not being limited thereto.

The pharmaceutical composition of the present disclosure has preventive or therapeutic effect for a disease caused by vascular leakage in the eye. The disease caused by vascular leakage in the eye may be any one known in the art. For example, it include retinal degeneration, macular degeneration, retinal edema and macular edema. Specifically, in the present disclosure, the disease caused by vascular leakage in the eye may be macular degeneration or macular edema.

The pharmaceutical composition according to the present disclosure may contain only the sesquiterpene derivative compound of Chemical Formula 1 or a pharmaceutically acceptable salt thereof or may further contain one or more pharmaceutically acceptable carrier, excipient or diluent.

As the pharmaceutically acceptable carrier, it may further contain, for example, a carrier for oral administration or a carrier for parenteral administration. The carrier for oral administration may include lactose, starch, cellulose derivatives, magnesium stearate, stearic acid, etc. And, the carrier for parenteral administration may include water, suitable oils, physiological saline, water-soluble glucose, glycol, etc. The pharmaceutical composition of the present disclosure may further contain a stabilizer and a preservative. A suitable stabilizer includes sodium bisulfite, sodium sulfite or an antioxidant such as ascorbic acid. A suitable preservative includes benzalkonium chloride, methyl- or propylparaben and chlorobutanol. In addition to these ingredients, the pharmaceutical composition of the present disclosure may further contain a lubricant, a humectant, a sweetener, a flavorant, an emulsifier, a suspending agent, etc. For other pharmaceutically acceptable carriers, reference can be made to the literature (Remington's Pharmaceutical Sciences, 19th ed., Mack Publishing Company, Easton, Pa., 1995).

The composition of the present disclosure may be administered to mammals including human by any means. For example, it may be administered orally or parenterally. The parenteral administration method may include intravenous, intramuscular, intraarterial, intramedullary, intradural, intracardiac, intraocular, intravitreal, transdermal, subcutaneous, intraabdominal, intranasal, intraintestinal, topical, sublingual or intrarectal administration, although not being limited thereto.

The pharmaceutical composition of the present disclosure may be prepared into a formulation for oral administration or parenteral administration depending on the administration routes.

For oral administration, the composition of the present disclosure may be formulated into a powder, a granule, a tablet, a pill, a sugar-coated tablet, a capsule, a solution, a gel, a syrup, a slurry, a suspension, etc. using the method known in the art. For example, as the formulation for oral administration, a tablet or a sugar-coated tablet may be prepared by mixing the active ingredient with a solid excipient, pulverizing the mixture, adding a suitable adjuvant and then processing into a granule mixture. Examples of the suitable excipient may include sugars including lactose, dextrose, sucrose, sorbitol, mannitol, xylitol, erythritol, maltitol, etc., a starches including corn starch, wheat starch, rice starch, potato starch, etc., celluloses including cellulose, methyl cellulose, sodium carboxymethyl cellulose, hydroxypropylmethyl cellulose, etc. and fillers such as gelatin, polyvinylpyrrolidone, etc. If necessary, crosslinked polyvinylpyrrolidone, agar, alginic acid, sodium alginate, etc. may be added as a disintegrant. In addition, the pharmaceutical composition of the present disclosure may further contain an antiagglomerant, a lubricant, a humectant, a flavor, an emulsifier, an antiseptic, etc.

For parenteral administration, the composition may be formulated into an injection, an eye drop, an ointment, a cream, a lotion, an oil, a gel, an aerosol or a nasal inhaler using the method known in the art. These formulations are described in the literature generally known in the field of pharmaceutical chemistry (Remington's Pharmaceutical Science, 15th Edition, 1975. Mack Publishing Company, Easton, Pa. 18042, Chapter 87: Blaug, Seymour).

Specifically, the pharmaceutical composition of the present disclosure may be prepared into a formulation selected from a group consisting of an oral medication, an injection, an eye drop and an ointment.

The total effective amount of the sesquiterpene derivative compound of the present disclosure or a pharmaceutically acceptable salt thereof may be administered to a patient with a single dose or a multiple dose according to the fractionated treatment protocol for long-term administration. The content of the active ingredient of the pharmaceutical composition of the present disclosure may vary depending on the severity of a disease. The effective administration dosage of the compound or a pharmaceutically acceptable salt thereof is determined in consideration of various factors including the route and number of administration of the pharmaceutical composition, the age, body weight, health condition and sex of a patient, the severity of a disease, diet, excretion rate, etc. Those of ordinary skill in the art will be able to determine the adequate effective administration dosage of the sesquiterpene derivative or a pharmaceutically acceptable salt thereof for prevention or treatment of a disease caused by vascular leakage in the eye in consideration of these factors. The pharmaceutical composition according to the present disclosure is not specially limited in formulation, administration route and administration method as long as the effect of the present disclosure can be achieved.

In another aspect, the present disclosure relates to a food composition for preventing or improving macular degeneration or macular edema, which contains the compound represented by Chemical Formula 1 or a pharmaceutically acceptable salt thereof as an active ingredient.

The food composition of the present disclosure includes all forms such as a functional food, a nutritional supplement, a health food, a food additive, a feed, etc. and is provided for animals including human or livestock. The food composition may be prepared into various forms according to the method known in the art.

For example, the health food may be prepared by preparing the sesquiterpene derivative of the present disclosure or a sponge extract containing the sesquiterpene into tea, juice or a drink for drinking or into a granule, a capsule or a powder. In addition, a composition may be prepared by mixing the sesquiterpene derivative of the present disclosure or a sponge extract containing the sesquiterpene with an active ingredient known to be effective in improving and preventing macular edema or macular degeneration.

Also, the functional food be prepared by adding the sesquiterpene derivative of the present disclosure or a sponge extract containing the sesquiterpene to beverages (including alcoholic beverage, fruit or processed fruit (e.g., canned fruit, bottling, jam, marmalade, etc.), fish, meat or processed foodstuffs thereof (e.g., ham, sausage corn beef, etc.), bread or noodles (e.g., udon, buckwheat noodle, instant noodle, spaghetti, macaroni, etc.), fruit juice, drinks, cookies, taffy, dairy products (e.g., butter, cheese, etc.), vegetable fats and oils, margarine, vegetable proteins, retort foods, frozen foods, condiments (e.g., soybean paste, soy sauce, etc.), etc.

In addition, the sesquiterpene derivative of the present disclosure or a sponge extract containing the sesquiterpene may be prepared into a powder or a concentrate for use as a food additive.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

<Preparation Example 1> Preparation of methyl 3-[[(1R,2S,4aR,8aS)-1,2,4a,5-tetramethyl-2,3,4,7,8, 8a-hexahydronaphthalen-1-yl]methyl]-4,5-dihydroxybenzoate A *Hyrtios* sp. (38 g dry weight) sample preserved in EtOH was extracted completely using MeOH. After evaporating the MeOH extract in vacuo, the remaining residue (15.6 g) was fractionated using water and a $CH_2Cl_2$ solvent. The organic phase was evaporated in vacuo and a gum (5.32 g) was obtained. 2.37 g of the gum was subjected to flash chromatography using a Si gel column and using hexane and EtOAc of increasing concentrations as eluents. Some of the resulting fractions were subjected to flash chromatography using a Si gel column and using hexane/EtOAc (100:0 to 50:50). Two UV-positive fractions were obtained and further purified by HPLC (UV detection at 210 nm, eluent 90:10 MeOH/H$_2$O) to obtain a compound of Preparation Example 1 (3 mg).

The obtained compound of Preparation Example 1 had the following physicochemical properties and was identified as 'methyl 3-[[(1R,2S,4aR,8aS)-1,2,4a,5-tetramethyl-2,3,4,7,8,8a-hexahydronaphthalen-1-yl]methyl]-4,5-dihydroxybenzoate'.

Amorphous solid.

IR (film) 3339, 1680, 1303 cm$^{-1}$.

UV (CH$_3$OH)) $\lambda_{max}$ 221 (17440), 269 (7460), 305 nm (3341, sh).

UV (CH$_3$OH/NaOH) $\lambda_{max}$ 210 (18520), 241 (13176), 284 (4310), 322 nm (6950).

$^1$H NMR (600 MHz) δ 7.49 (1H, d, 1.5), 7.45 (1H, d, 1.5), 5.32 (1H, bs), 3.87 (3H, s), 2.84 (1H, d, 14) and 2.60 (1H, d, 14) AB system, 1.64 (3H, bs), 0.98 (3H, d, 6), 0.95 (3H, s), 0.90 (3H, s).

$^{13}$C NMR (CDCl$_3$, 150.87 MHz): see [Table 2].

TABLE 2

| Carbon | Preparation Example 1(δ ppm) |
| --- | --- |
| C-4 | 19.7 |
| C-2 | 25 |
| C-3 | 124.3 |
| C-4 | 140 |
| C-5 | 37.7 |
| C-6 | 37.8 |
| C-7 | 29.5 |
| C-8 | 37.6 |
| C-9 | 43.9 |
| C-10 | 44.9 |
| C-11 | 38.1 |
| C-12 | 17.3 |
| C-13 | 18.4 |
| C-14 | 33 |
| C-15 | 20.5 |
| C-16 | 126.2 |
| C-17 | 149.2 |
| C-18 | 143.1 |
| C-19 | 114.6 |
| C-20 | 121.3 |
| C-21 | 128.1 |
| C-22 | 168.2 |
| C-23 | 52.8 |

<Preparation Example 2> Preparation of 3-[[(1S,2R,4aR,8aR)-1,2,4a-trimethyl-5-methylidene-3,4,6,7,8,8a-hexahydro-2H-naphthalen-1-yl]methyl]-2,5-dihydroxycyclohexa-2,5-diene-1,4-dione A sponge (Smenospongia sp.) sample (2 kg) was immersed in MeOH and extracted with CHCl$_3$/MeOH (1/1 mixture). The extract was evaporated under reduced pressure and an aqueous suspension thereof was extracted with CH$_2$Cl$_2$ (extract A). The extract A (8 g) was subjected to silica gel (CHCl$_3$/MeOH of increasing concentrations) chromatography. A fraction 1 eluted with 2% MeOH (in CHCl$_3$) and a fraction 2 eluted with 5% MeOH (in CHCl$_3$) were prepared therefrom. The fraction 1 was eluted with 30% AcOEt (in hexane) to obtain a compound of Preparation Example 2 (20 mg).

The obtained compound of Preparation Example 2 had the following physicochemical properties and was identified as '3-[[(1S,2R,4aR,8aR)-1,2,4a-trimethyl-5-methylidene-3,4,6,7,8,8a-hexahydro-2H-naphthalen-1-yl]methyl]-2,5-dihydroxycyclohexa-2,5-diene-1,4-dione'.

C$_{21}$H$_{28}$O$_4$.

m.p. >350° C.

SM m/e (%): 191 (40), 154 (12), 135 (44), 121 (65), 109 (56), 107 (87), 95 (100).

UV (EtOH) $\lambda_{max}$ nm (ε): 214, 286.

IR (KBr) ν cm$^{-1}$: 3324, 2940, 1645, 1535.

$^1$H NMR (MeOD, 80 MHz) δ ppm: 5.71 (1H, s), 4.76 (2H, br s), 2.40 (2H, br s), 1.01 (3H, s), 0.92 (3H, d, J=7 HZ), 0.78 (3H, s).

$^{13}$C NMR (δ ppm, CD$_3$OD, 20.115 MHz): see [Table 3].

<Preparation Example 3> Preparation of 3-[[(1R,2S,4aS,8aS)-1,2,4a-trimethyl-5-methylidene-3,4,6,7,8,8a-hexahydro-2H-naphthalen-1-yl]methyl]-4-hydroxy-5-(3-methylbutylamino)cyclohexa-3,5-diene-1,2-dione 44 g of dried sponge (Smenospongia sp.) was extracted with CH$_2$C$_{12}$ and then with MeOH (extract B). The extract B (4 g) was subjected to chromatography using a silica gel column (CHCl$_3$/increasing amounts MeOH) to obtain a fraction A eluted with 2% MeOH (in CHCl$_3$) and a fraction B eluted with 5% MeOH (in HCl$_3$). The faction A was purified with a Sephadex LH 20 (MeOH/CHCl$_3$: 60/40) column to obtain a compound of Preparation Example 3 (20 mg) and a compound of Preparation Example 4 (5 mg).

The obtained compound of Preparation Example 3 had the following physicochemical properties and was identified as '3-[[(1R,2S,4aS,8aS)-1,2,4a-trimethyl-5-methylidene-3,4,6,7,8,8a-hexahydro-2H-naphthalen-1-yl]methyl]-4-hydroxy-5-(3-methylbutylamino)cyclohexa-3,5-diene-1,2-dione'.

C$_{26}$H$_{39}$NO$_3$.

m.p.: 170-172° C.

SM m/e (%): 413 (4), 311 (8), 283 (12), 223 (100), 191 (11), 167 (22), 153 (27), 149 (15), 135 (14), 121 (16), 109 (18), 107 (12), 95 (79).

m/e 191.179, calc. 191.179 for C$_{14}$H$_{23}$; m/e 223.119, calc. 223.120 for C$_{12}$H$_{17}$NO$_3$.

UV (EtOH) $\lambda_{max}$ nm (ε): 204 (27230), 324 (14070).

IR (KBr) ν cm$^{-1}$: 3417, 3275, 1640, 1592.

$^1$H NMR (CDCl$_3$ 0.200 MHz) δ ppm: 8.41 (1H exch., s), 6.41 (1H exch., t). 5.36 (1H, s), 4.43 (br s), 3.20 (2H, dt), 2.48 (d), 2.37 (d) (AB syst.), 2.31 (dt), 2.07 (2H, m), 1.85 (1H, m), 1.80-1.05 (11H, m), 1.04 (3H, s), 0.95 (9H, 3d overlapped), 0.83 (3H, s), 0.78 (1H, dd).

$^{13}$C NMR (δ ppm, CDCl$_3$, 20.115 MHz): see [Table 3].

TABLE 3

| Carbon | Preparation Example 2(δ ppm) | Preparation Example 3(δ ppm) |
| --- | --- | --- |
| 1 | 24.49 t | 23.20 t |
| 2 | 29.48 t | 27.98 t |
| 3 | 38.30 t | 36.85 t |
| 4 | 162.35 s | 160.33 s |
| 5 | 41.61 s | 40.41 s |
| 6 | 33.70 t | 32.97 t |
| 7 | 30.05 t | 28.63 t |
| 8 | 39.20 d | 37.% d |
| 9 | 43.65 s | 42.89 s |
| 10 | 51.46 d | 50.01 d |
| 11 | 102.58 t | 102.39 t |
| 12 | 21.06 q | 20.48 q |
| 13 | 18.88 q | 17.80 q |

TABLE 3-continued

| Carbon | Preparation Example 2(δ ppm) | Preparation Example 3(δ ppm) |
|---|---|---|
| 14 | 17.85 q | 17.16 q |
| 15 | 33.94 t | 32.57 t |
| 16 | 114.45 s | 113.53 s |
| 17 | 188.82 s* | 157.06 s |
| 18 | 179.65 s* | 182.77 s |
| 19 | 101.79 d | 91.484 d |
| 20 | 174.72 s* | 150.21 s |
| 21 | 166.80 s* | 177.97 s |

*may be reversed

<Preparation Example 4> Preparation of 3-[[(1S, 2R,4aR,8aR)-1,2,4a-trimethyl-5-methylidene-3,4,6, 7,8,8a-hexahydro-2H-naphthalen-1-yl]methyl]-4-hydroxy-5-(2-methylpropylamino)cyclohexa-3,5-diene-1,2-dione A compound of Preparation Example 4 was prepared in the same manner as in Preparation Example 3. The obtained compound (Preparation Example 4) had the following physicochemical properties and was identified as '3-[[(1S,2R, 4aR,8aR)-1,2,4a-trimethyl-5-methylidene-3,4,6,7,8,8a-hexahydro-2H-naphthalen-1-yl]methyl]-4-hydroxy-5-(2-methylpropylamino)cyclohexa-3,5-diene-1,2-dione'.

$C_{25}H_{37}NO_3$.

SM m/e (%): 399 (5). 209 (100). 191(17), 166 (36). 152 (18), 135 (11), 121 (15), 109 (15), 107 (12), 95 (66).

UV (EtOH) $\lambda_{max}$ nm (ε): 210 (14000), 329 (20150).

IR (KBr) ν cm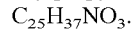: 3417, 3275, 1640, 1592.

$^1$H NMR (CDCl$_3$, 200 MHz) δ ppm: 6.53 (1H, s). 5.41 (1H, s), 4.45 (2H, br s), 2.95 (2H, dt), 2.48 (1H, d), 2.45 (1H, d, J=13 Hz), 1.03 (3H, s), 0.97 (9H, 3d overlapped), 0.82 (3H, s). 0.76 (1H, dd).

<Preparation Example 5> Preparation of 3-[[(1R, 2S,4aS,8aS)-1,2,4a-trimethyl-5-methylidene-3,4,6,7, 8,8a-hexahydro-2H-naphthalen-1-yl]methyl]-5-amino-4-hydroxycyclohexa-3,5-diene-1,2-dione MeOH and DCM crude extracts of Hippospongia sp. were combined and fractionated with MeOH, DCM, hexane and BuOH. Among them, the hexane, DCM and MeOH fractions were subjected to flash column chromatography and semi-preparative RP-HPLC to obtain a compound of Preparation Example 5.

The obtained compound (Preparation Example 5) had the following physicochemical properties and was identified as '3-[[(1R,2S,4aS,8aS)-1,2,4a-trimethyl-5-methylidene-3,4,6, 7,8,8a-hexahydro-2H-naphthalen-1-yl]methyl]-5-amino-4-hydroxycyclohexa-3,5-diene-1,2-dione'.

Purple solid.

$C_{21}H_{30}O_3N$ (HRESIMS m/z 344.2295, [M+H]$^+$).

UV (MeOH) $\lambda_{max}$ (log ε) 315 (3.58) nm.

IR (KBr) 3835, 3566, 1624, 1536 cm$^{-1}$.

$^1$H NMR (400 MHz, CD$_3$OD) δ: 2.17/1.43 (2H, m H-1), 1.39 (2H, m, H-2), 1.50/1.38 (2H, m, H-3), 2.34/2.05 (2H, m, H-6), 1.23/1.82 (2H, m, H-7), 1.23 (1H, m, H-8), 0.82 (1H, m, H-10), 4.44 (2H, s, H-11), 1.05 (3H, s, H-12), 0.98 (3H, d, J=6.4 Hz H-13), 0.84 (3H, s, H-14), 2.47/2.40 (2H, dd, J=13.7 Hz, H-15), 5.51 (1H, s, H-19).

$^{13}$C NMR (100 MHz, CD$_3$OD) δ: 22.8 (t, C-1), 27.5 (t, C-2), 36.4 (t, C-3), 160.1 (s, C-4), 39.9 (s, C-5), 32.5 (t, C-6), 28.3 (t, C-7), 37.6 (d, C-8), 42.1 (s, C-9), 49.7 (d, C-10), 101.1 (t, C-11), 19.4 (q, C-12), 16.9 (q, C-13), 16.2 (q, C-14), 31.6 (t, C-15), 113.7 (s, C-16), 159.4 (s, C-17), 183.2 (s, C-18), 93.6 (d, C-19), 183.2 (s, C-21).

<Preparation Example 6> Preparation of 2-[[5-[[(1R,2S,4aS,8aS)-1,2,4a-trimethyl-5-methylidene-3, 4,6,7,8,8a-hexahydro-2H-naphthalen-1-yl]methyl]-6-hydroxy-3,4-dioxocyclohexa-1,5-dien1-yl]amino] acetic Acid After freeze-drying sponge (Dactylospongia elegans), an extract obtained by adding MeOH (3×1 L) to the freeze-dried sponge (33 g dry weight) was concentrated in vacuo and subjected to reversed-phase C$_{18}$ vacuum liquid chromatography (0%, 20%, 50%, 70%, 90%, 100% MeOH in H$_2$O and 1:1 CH$_2$Cl$_2$/MeOH). 20%, 50% and 70% MeOH fractions were obtained and subjected to C$_{18}$ preparative HPLC (4 mL/min, gradient elution from 3:7 H$_2$O/MeCN/0.1% formic acid to 100% MeCN/0.1% formic acid over 10 min, through a 150×10 mm, 5 μm Phenomenex phenyl hexyl column). A Preparation Example 6 compound (11.7 mg, 0.035%), a Preparation Example 7 compound (1.4 mg, 0.004%) and a Preparation Example 8 compound (0.8 mg, 0.002%) were obtained therefrom.

The prepared Preparation Example 6 compound had the following physicochemical properties and was identified as '2-[[5-[[(1R,2S,4aS,8aS)-1,2,4a-trimethyl-5-methylidene-3, 4,6,7,8,8a-hexahydro-2H-naphthalen-1-yl]methyl]-6-hydroxy-3,4-dioxocyclohexa-1,5-dien-1-yl]amino]acetic acid'.

Amorphous, red solid;

[α]$_D$+94.4 (c 0.018, MeOH).

UV (PDA, CH$_3$CN/H$_2$O) $\lambda_{max}$ 218, 311, 494 nm.

IR (neat) ν$_{max}$ 3598, 2936, 2064, 1657 cm$^{-1}$.

$^1$H (300 MHz) and $^{13}$C (75 MHz) NMR (CD$_3$OD): see [Table 4].

HRESIMS m/z 424.2104 [M+Na]$^+$ (calcd for C$_{23}$H$_{31}$NO$_5$Na, 424.2094, Δ 1.0 mmu).

TABLE 4

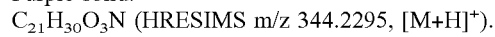

| no. | $\delta_C$, mult.[a,b] | $\delta_H$ (J in Hz)[a,c] | COSY[a] | gHMBC[a,d] | $\delta_{C'}$ mult.[b,e] | $\delta_H$ (J in Hz)[c,e] |
|---|---|---|---|---|---|---|
| 1 | 24.2, CH$_2$ | 2.19, br d (12.7) | H$_b$-1, H$_2$-2, H-10 | 2, 15 | 22.7, CH$_2$ | 2.09, m |
|  |  | 1.48, m | H$_a$-1, H$_a$-2, H-10 |  |  | 1.35, m |
| 2 | 29.7, CH$_2$ | 1.84, dd (12.7, 3.0) | H$_b$-1, H$_b$-2, H$_2$-3 |  | 28.0, CH$_2$ | 1.74, m |
|  |  | 1.23, m | H$_a$-1, H$_a$-2, H$_b$-3 |  |  | 1.14, m |
| 3 | 34.0, CH$_2$ | 2.35, ddd (13.8, 5.2, 3.0) | H$_a$-2, H$_b$-3, H$_2$-11 | 4 | 32.1, CH$_2$ | 2.23, m |
|  |  | 2.04, dd (13.8, 5.2) | H$_a$-2, H$_a$-3 | 1, 2, 4, 11 |  | 1.99, m |
| 4 | 161.4, C |  |  |  | 159.3, C |  |
| 5 | 41.3, C |  |  |  | 39.8, C |  |
| 6 | 37.8, CH$_2$ | 1.51, m | H$_b$-6, H$_a$-7 | 8, 10 | 36.4, CH$_2$ | 1.43, m |
|  |  | 1.41, m | H$_b$-6 | 5, 7, 8, 12 |  | 1.27, m |
| 7 | 28.8, CH$_2$ | 1.40, m | H$_2$-6 | 6, 8, 9 | 27.6, CH$_2$ | 1.32, m |
|  |  |  |  |  |  | 1.11, m |
| 8 | 38.9, CH | 1.25, m | H$_a$-7, H$_3$-13 | 7, 13 | 37.3, CH | 1.17, m |
| 9 | 43.7, C |  |  |  | 42.2, C |  |
| 10 | 50.9, CH | 0.85, m | H$_2$-1 | 1, 8, 9, 12, 15 | 49.3, CH | 0.74, m |

TABLE 4-continued

| no. | $\delta_C$, mult.[a,b] | $\delta_H$ (J in Hz)[a,c] | COSY[a] | gHMBC[a,d] | $\delta_C$, mult.[b,e] | $\delta_H$ (J in Hz)[c,e] |
|---|---|---|---|---|---|---|
| 11 | 103.1, CH$_2$ | 4.40, br s | H$_a$-3, H$_2$-11 | 3, 4, 5 | 102.9, CH$_2$ | 4.40, s |
|  |  |  |  |  |  | 4.37, s |
| 12 | 20.9, CH$_3$ | 1.05, s |  | 4, 5, 6, 10 | 20.2, CH$_3$ | 0.97, s |
| 13 | 18.5, CH$_3$ | 0.98, d (6.3) | H-8 | 7, 8, 9 | 18.1, CH$_3$ | 0.92 d (6.2) |
| 14 | 17.4, CH$_3$ | 0.84, s |  | 8, 9, 10, 15 | 17.3, CH$_3$ | 0.76, s |
| 15 | 33.1, CH$_2$ | 2.50, d (13.8) | H$_b$-15 | 8, 9, 10, 14, 16, 17, 21 | 32.0, CH$_2$ | 2.36, d (13.6) |
|  |  | 2.40, d (13.8) | H$_a$-15 | 8, 9, 10, 14, 16, 17, 21 |  | 2.27, d (13.6) |
| 16 | 115.4, C |  |  |  | 113.2, C |  |
| 17 | 159.4, C |  |  |  | 159.7, C |  |
| 18 | 182.2, C |  |  |  | 180.4, C |  |
| 19 | 93.6, CH | 5.27, s |  | 17, 18, 21 | 92.9, CH | 5.19, s |
| 20 | 150.9, C |  |  |  | 149.6, C |  |
| 21 | 183.8, C |  |  |  | 181.8, C |  |
| 22 |  |  |  |  |  | 7.56 t (5.8) |
| 23 | 44.7, CH$_2$ | 3.94, br s |  | 20, 24 | 42.1, CH$_2$ | 3.88, d (5.8) |
| 24 | 171.7, C |  |  |  | 169.8, C |  |

[a]CD$_3$OD.
[b]75 MHz.
[c]300 MHz.
[d]HMBC correlations are from proton(s) stated to the indicated carbons.
[e]DMSO-d$_6$ <Preparation Example 7> Preparation of 3-[[5-[[(1R,2S,4aS,8aS)-1,2,4a-trimethyl-5-methylidene-3,4,6,7,8,8a-hexahydro-2H-naphthalen-1-yl]methyl]-6-hydroxy-3,4-dioxocyclohexa-1,5-dien1-yl]amino]propanoic Acid A compound of Preparation Example 7 was prepared in the same manner as in Preparation Example 6. The prepared compound (Preparation Example 7) had the following physicochemical properties and was identified as '3-[[5-[[(1R,2S,4aS,8aS)-1,2,4a-trimethyl-5-methylidene-3,4,6,7,8,8a-hexahydro-2H-naphthalen-1-yl]methyl]-6-hydroxy-3,4-dioxocyclohexa-1,5-dien-1-yl]amino]propanoic acid'.

Amorphous, red solid.
$[\alpha]_D$+13 (c 0.06, MeOH).
UV (PDA, CH$_3$CN/H$_2$O) $\lambda_{max}$ 233, 314, 494 nm.
IR (neat) $\nu_{max}$ 3410, 2930, 1686, 1632, 1567 cm$^{-1}$.
HRESIMS m/z 438.2264 [M+Na]$^+$ (calcd for C$_{24}$H$_{33}$NO$_5$Na, 438.2251, $\Delta$ 1.3 mmu).
$^1$H NMR (CD$_3$OD, 300 MHz) δ 5.38 (1H, s, H-19), 4.40 (2H, s, H$_2$-11), 3.45 (2H, t, J=6.8 Hz, H$_2$-23), 2.59 (2H, t, J=6.8 Hz, H$_2$-24), 2.47 (1H, d, J=13.6 Hz, H$_a$-15), 2.38 (1H, d, J=13.6 Hz, H$_b$-15), 2.32 (1H, m, H$_a$-3), 2.16 (1H, m, H$_a$-1), 2.04 (1H, m, H$_b$-3), 1.80 (1H, m, H$_a$-2), 1.48 (1H, m, H$_a$-6), 1.43 (1H, m, H$_b$-1), 1.41 (1H, m, H$_a$-7), 1.36 (1H, m, H$_b$-6), 1.35 (1H, m, H$_b$-7), 1.29 (1H, m, H$_b$-2), 1.21 (1H, m, H-8), 1.04 (3H, s, H$_3$-12), 0.97 (3H, d, J=6.4 Hz, H$_3$-13), 0.83 (3H, s, H$_3$-14), 0.81 (1H, m, H-10).
$^{13}$C NMR (CD$_3$OD, 75 MHz) δ 183.4 (C, C-21), 179.6 (C, C-18), 176.0 (C, C-25), 162.9 (C, C-4), 161.1 (C, C-17), 152.0 (C, C-20), 115.5 (C, C-16), 103.3 (CH$_2$, C-11), 92.6 (CH, C-19), 51.1 (CH, C-10), 44.0 (C, C-9), 41.8 (C, C-5), 39.9 (CH$_2$, C-23), 39.0 (CH, C-8), 38.2 (CH$_2$, C-6), 34.5 (CH$_2$, C-24), 34.2 (CH$_2$, C-3), 33.4 (CH$_2$, C-15), 30.0 (CH$_2$, C-2), 29.4 (CH$_2$, C-7), 24.3 (CH$_2$, C-1), 21.4 (CH$_3$, C-12), 18.7 (CH$_3$, C-13), 18.1 (CH$_3$, C-14).

<Preparation Example 8> Preparation of 7-[[(1R,2S,4aS,8aS)-1,2,4a-trimethyl-5-methylidene-3,4,6,7,8,8a-hexahydro-2H-naphthalen-1-yl]methyl]-1,3-benzoxazole-5,6-diol A compound of Preparation Example 8 was prepared in the same manner as in Preparation Example 6. The prepared compound (Preparation Example 8) had the following physicochemical properties and was identified as '7-[[(1R,2S,4aS,8aS)-1,2,4a-trimethyl-5-methylidene-3,4,6,7,8,8a-hexahydro-2H-naphthalen-1-yl]methyl]-1,3-benzoxazole-5,6-diol'.

Colorless solid.
$[\alpha]_D$−6.7 (c 0.075, MeOH).
UV (PDA, CH$_3$CN/H$_2$O) $\lambda_{max}$ 236, 297, 323 (sh) nm.
IR (neat) $\nu_{max}$ 3408, 2927, 1541 cm$^{-1}$.
$^1$H (300 MHz) and 13C (75 MHz) NMR (CD$_3$OD): see [Table 5].
HRESIMS m/z 378.2050 [M+Na]$^+$ (calcd for C$_{22}$H$_{29}$NO$_3$Na, 378.2040, $\Delta$ 1.0 mmu).

TABLE 5

| no. | $\delta_C$, mult.[a] | $\delta_H$ (J in Hz)[b] | COSY | gHMBC[c] |
|---|---|---|---|---|
| 1 | 24.8, CH$_2$ | 2.37, m | H$_b$-1, H$_a$-2, H-10 | 2 |
|  |  | 1.55, m | H$_a$-1, H-10 |  |
| 2 | 30.2, CH$_2$ | 1.87, m | H$_b$-2, H$_a$-3 |  |
|  |  | 1.28, m | H$_a$-1, H$_a$-2, H$_2$-3 |  |
| 3 | 34.4, CH$_2$ | 2.32, m | H$_b$-2, H$_b$-3 | 2, 4, 11 |
|  |  | 2.03, m | H$_a$-2, H$_a$-3 | 5 |
| 4 | 161.8, C |  |  |  |
| 5 | 41.8, C |  |  |  |
| 6 | 38.5, CH$_2$ | 1.45, m |  | 8 |
| 7 | 29.5, CH$_2$ | 1.41, m |  |  |
| 8 | 38.7, CH | 1.41, m | H$_3$-13 |  |
| 9 | 44.2, C |  |  |  |
| 10 | 51.1, CH | 0.94, m | H$_2$-1 | 5, 9, 12, 14 |
| 11 | 103.4, CH$_2$ | 4.35, s |  | 3, 4, 5 |
|  |  | 4.32, s |  | 3, 4, 5 |
| 12 | 20.7, CH$_3$ | 1.07, s |  | 4, 5, 6, 10 |
| 13 | 19.2, CH$_3$ | 1.08, d (6.8) | H-8 | 7, 8, 9 |
| 14 | 18.3, CH$_3$ | 0.95, s |  | 8, 9, 10, 15 |
| 15 | 35.8, CH$_3$ | 2.94, d (13.9) | H$_b$-15 | 8, 9, 10, 14, 16, 17, 21 |
|  |  | 2.86, d (13.9) | H$_a$-15 | 8, 9, 10, 14, 16, 17, 21 |
| 16 | 111.0, C |  |  |  |
| 17 | 146.7, C |  |  |  |
| 18 | 145.2, C |  |  |  |
| 19 | 102.6, CH | 6.96, s |  | 17, 18, 20, 21 |
| 20 | 131.7, C |  |  |  |
| 21 | 146.7, C |  |  |  |
| 22 | 153.2, CH | 8.20, s |  | 20, 21 |

[a]75 MHz.
[b]300 MHz.
[c]HMBC correlations are from proton(s) stated to the indicated carbons.

<Preparation Example 9> Preparation of [7-[[(1R,2S,4aS,8aS)-1,2,4a-trimethyl-5-methylidene-3,4,6,7,8,8a-hexahydro-2H-naphthalen-1-yl]methyl]-6-acetyloxy-1,3-benzoxazol-5-yl]acetate As in Preparation Example 5, after freeze-drying sponge (*Dactylospongia elegans*), an extract was prepared by adding MeOH (3×1 L) to the freeze-dried sponge (33 g dry weight). The substance insoluble in MeOH (120 mg) was added to pyridine (0.5 mL) and stirred at room temperature for 12 hours after treating with (CH$_3$CO)$_2$O (0.5 mL). The obtained substance was concentrated in vacuo and subjected to sequential reversed-phase HPLC separation (A: H$_2$O/MeCN+0.1% formic acid (3:7) to 100% MeCN+0.1% formic acid over 10 min at 4 mL/min and held for an additional 10 min on a 150×10 mm, 5 μm Phenomenex Luna $C_{18}$ column; B: $H_2O$/MeOH with 0.1% formic acid (3:7) to 100% MeOH with 0.1% formic acid for 10 min at 4 mL/min and held for an additional 5 min on a 150×10 mm, 5 μm Phenomenex Luna phenyl hexyl column). The obtained compound of Preparation Example 9 (2.3 mg, 0.007%) had the following physicochemical properties and was identified as '[7-[[(1R,2S,4aS,8aS)-1,2,4a-trimethyl-5-methylidene-3,4,6,7,8,8a-hexahydro-2H-naphthalen-1-yl]methyl]-6-acetyloxy-1,3-benzoxazol-5-yl] acetate'.

Colorless oil.

$[\alpha]_D$ –170 (c 0.003, $CHCl_3$).

UV (PDA, $CH_3CN/H_2O$) $\lambda_{max}$ 233, 278, 284, 300 (sh) nm.

IR (neat) $\nu_{max}$ 3488, 2927, 1775, 1630, 1458 $cm^{-1}$.

HRESIMS m/z 462.2250 [M+Na]+ (calcd for $C_{26}H_{33}NO_5Na$, 462.2251, Δ 0.1 mmu).

$^1$H NMR ($CDCl_3$, 300 MHz) δ 8.07 (1H, s, H-22), 7.54 (1H, s, H-19), 4.42 (1H, d, J=1.6 Hz, $H_a$-11), 4.38 (1H, d, J=1.6 Hz, $H_b$-11), 2.83 (1H, d, J=14.2 Hz, $H_a$-15), 2.76 (1H, d, J=14.2 Hz, $H_b$-15), 2.35 (1H, m, $H_a$-3), 2.34 (s, a-OCOCH$_3$), 2.30 (s, b-OCOCH3), 2.08 (1H, m, $H_b$-3), 1.92 (1H, m, $H_a$-2), 1.58 (1H, m, $H_a$-1), 1.49 (1H, m, $H_a$-6), 1.45 (1H, m, $H_b$-1),1.43 (1H, m, H-8), 1.42 (2H, m, $H_2$-7), 1.28 (1H, m, $H_b$-6), 1.26 (1H, m, $H_b$-2), 1.07 (3H, s, $H_3$-12), 0.97 (3H, d, J=5.6 Hz, $H_3$-13), 0.94 (3H, s, $H_3$-14), 0.92 (1H, m, H-10).

$^{13}$C NMR ($CDCl_3$, 150 MHz) δ168.1 (C, a-OCOCH$_3$), 167.9 (C, b-OCOCH$_3$), 159.1 (C, C-4), 152.7 (CH, C-22), 147.9 (C, C-21), 140.4 (C, C-17), 137.4 (C, C-18), 136.6 (C, C-20), 118.3 (C, C-16), 111.9 (CH, C-19), 102.2 ($CH_2$, C-11), 50.1 (CH, C-10), 43.0 (C, C-9), 40.3 (C, C-5), 37.6 (CH, C-8), 36.2 ($CH_2$, C-6), 35.6 ($CH_2$, C-15), 32.6 ($CH_2$, C-3), 28.3 ($CH_2$, C-2), 27.7 ($CH_2$, C-7), 23.1 ($CH_2$, C-1), 20.1 (2×$CH_3$, —OCOCH$_3$), 19.9 ($CH_3$, C-12), 18.1 ($CH_3$, C-13), 16.8 ($CH_3$, C-14).

<Preparation Example 10> Preparation of 3-[[(1R, 2S,4aS,8aS)-1,2,4a,5-tetramethyl-2,3,4,7,8,8a-hexahydronaphthalen-1-yl]methyl]-2-hydroxy-5-methoxycyclohexa-2,5-diene-1,4-dione A sponge (Spongiidae SS-1047, 0.30 kg, wet weight) was obtained as described in the literature 'Yohei Takahashi et al., 2010' and extracted. Briefly, EtOAc-soluble substances (1.2 g) were fractionated using a silica gel column (n-hexane/EtOAc) and a fraction 1, a fraction 2 and a fraction 3 of low polarity and a polar fraction 4 were prepared. The fraction 3 was fractionated and purified by $C_{18}$ column (MeOH/$H_2O$) and $C_{18}$ HPLC (Luna 5u Phenyl-Hexyl, 250×10 mm; eluent, MeOH/$H_2O$/$CF_3CO_2H$, 85:15:0.05; flow rate, 2.5 mL/min; UV detection at 320 nm) to obtain compounds of Preparation Example 10 and Preparation Example 11.

The obtained Preparation Example 10 compound had the following physicochemical properties and was identified as '3-[[(1R,2S,4aS,8aS)-1,2,4a,5-tetramethyl-2,3,4,7,8,8a-hexahydronaphthalen-1-yl]methyl]-2-hydroxy-5-methoxycyclohexa-2,5-diene-1,4-dione'.

m.p.: 95-98° C.

$[\alpha]^{20}_{579}$+64.4° (c 0.27 $CHCl_3$).

IR (film) 3341, 1652, 1645, 1609, 1243 $cm^{-1}$.

UV ($CH_3OH$) $\lambda_{max}$ 213 (9600), 288 nm (13485).

UV ($CH_3OH$/NaOH) $\lambda_{max}$ 210 (12850), 290 (8930), 526 nm (1650).

$^1$H NMR (600 MHz, $CDCl_3$, δ, J in Hz): see [Table 6].

$^{13}$C NMR (150.87 MHz, $CDCl_3$): see [Table 6].

HREIMS m/z 358.2151 [M+] (12, calcd for $C_{22}H_{30}O_4$, 358.2144), 191.1803 (15, calcd for $C_{14}H_{23}$, 191.1800), 168.0423 (41, calcd for $C_8H_8O_4$, 168.0422), 121.1013 (12, calcd for $C_9H_{13}$, 121.1017), 107.0859 (30, calcd for $C_8H_{11}$, 107.0861), 95.0861 (100, calcd for $C_7H_{11}$, 95.0861).

TABLE 6

| position | $^1$H NMR | carbon | $^{13}$C NMR $1^a$ | $1^b$ | $1^c$ |
| --- | --- | --- | --- | --- | --- |
| $H_2$C-1 | 1.40, m<br>1.97, m | C-1 | 17.7 | 19.9 | 20.6 |
| $H_2$C-2 | 1.82, m<br>1.93, m | C-2 | 27.1 | 27.1 | 27.8 |
| HC-3 | 5.06, bs | C-3 | 121 | 121 | 121.6 |
| $H_2$C-6 | 0.96(ax), m<br>1.57(eq), ddd, 13.0, 3.0, 3.0 | C-4 | 143.9 | 143.9 | 144.7 |
| $H_2$C-7 | 1.25, m<br>1.28, m | C-5 | 43.1 | 38.6 | 39.2 |
| HC-8 | 1.17, m | C-6 | 36.1 | 36.1 | 36.7 |
| HC-10 | 0.95, bd, 12.0 | C-7 | 28.1 | 28.1 | 28.6 |
| $H_2$C-11 | 2.42, d, 14.0<br>2.55, d, 14.0<br>ABsystem | C-8 | 38.1 | 38.1 | 38.6 |
| $H_3$C-12 | 0.77, s | C-9 | 38.6 | 43.1 | 43.8 |
| $H_3$C-13 | 0.90, d, 6.0 | C-10 | 48.2 | 48.2 | 48.6 |
| $H_3$C-14 | 0.94, s | C-11 | 32.5 | 32.5 | 33 |
| $H_3$C-15 | 1.47, bs | C-12 | 17.3 | 17.3 | 18 |
| $H_3$C-0 | 3.79, s | C-13 | 18.1 | 17.7 | 18.4 |
| HC-18 | | C-14 | 19.9 | 20.2 | 20.9 |
| HC-19 | 5.77, s | C-15 | 20.2 | 18.1 | 18.9 |
| HC-21 | | C-16 | 117.8 | 117.8 | 118.3 |
| | | C-17 | 182.4 | 182.4 | 183 |
| | | C-18 | 161.8 | 161.8 | 162.5 |
| | | C-19 | 102 | 102 | 102.7 |
| | | C-20 | 182 | 182 | 182.8 |
| | | C-21 | 153.4 | 153.4 | 154 |
| | | C-22 | 56.8 | 56.8 | 57.5 |

<Preparation Example 11> Preparation of 2-hydroxy-5-methoxy-3-[[(1R,2S)-1,2,5,5-tetramethyl-2,3,6,7,8,8a-hexahydronaphthalen-1-yl]methyl]cyclohexa-2,5-diene-1,4-dione A compound of Preparation Example 11 was prepared in the same manner as in Preparation Example 10. The obtained compound (Preparation Example 11) had the following physicochemical properties and was identified as '2-hydroxy-5-methoxy-3-[[(1R,2S)-1,2,5,5-tetramethyl-2,3,6,7,8,8a-hexahydronaphthalen-1-yl]methyl]cyclohexa-2,5-diene-1,4-dione'.

Pale yellow feathery solid.

m.p. 108.5-109.5° C.

$C_{22}H_{30}O_4$ (high resolution FABMS (M+ 358.2146, Δ 0.2 mmu, $C_{22}H_{30}O_4$; MH+ 359.2223, Δ 0.1 mmu, $C_{22}H_{31}O_4$)).

$^1$H NMR (500 MHz, $CDCl_3$) δ: 0.73 (s, 3H), 0.90 (sh, 1H), 0.92 (s, 3H), 0.96 (d, J=7 Hz, 3H), 0.99 (s, 3H), 1.12 (ddd, J=13.5, 13.5, 4.3 Hz, 1H), 1.33-1.45 (complex mult., 4H), 1.73 (mult, 1H), 1.79 (br d, 1H), 1.95 (ddd, J=18, 17.5, 4.5 Hz, 1H), 2.08 (br d, J=13 Hz, 1H), 2.45 (d, cJ=13.0 HZ, 1H), 2.58 (d, J=13.0 Hz, 1H), 3.84 (s, 3H), 5.35 (br s, 1H), 5.84 (s, 1H), 7.45 (s, 1H);

$^{13}$C NMR (500 MHz, CDCl3), δ (mult., proton assignments): 16.0 (q, 0.73, C-14), 16.5 (q, 0.92, C-11), 22.7 (t, 1.40, 1.46, C-2), 27.9 (q, 0.96, C-13), 29.7 (q, 0.99, C-12). 30.6 (t, 0.90, 1.79, C-1), 31.5 (t, 1.73, 1.95, C-7), 32.7 (t, 2.45, 2.58, C-15), 36.3 (s, C-4), 36.4 (d, 1.36, C-8), 40.9 (s, C-g), 41.2 (t, 1.13, 1.32, C-3), 41.7 (s, 2.08, C-10), 56.8 (q, 3.86, C-22), 102.0 (d, 5.85, C-19),114.8 (d, 5.35, C-6), 118.3 (s, C-16), 146.3 (s, C-5), 152.8 (s, —OH, C-17), 161.5 (s, C-20), 182.0 (s, C-21), 182.4 (s, C-18).

<Preparation Example 12> Preparation of 3-[[(1R, 2S,8aS)-1,2,5,5-tetramethyl-2,3,6,7,8,8a-hexahydronaphthalen-1-yl]methyl]-4-hydroxy-5-(2-phenylethylamino)cyclohexa-3,5-diene-1,2-dione The fraction 1 obtained in Preparation Example 10 was refractionated by $C_{18}$ column (MeOH/H$_2$O) and $C_{18}$ HPLC (Wakosil-II 5C18AR, Wako Pure Chemical Industries, Ltd., 250×10 mm; eluent, MeCN/H$_2$O/CF$_3$CO$_2$H, 90:10:0.05; flow rate, 2.0 mL/min; UV detection at 300 nm) to obtain a compound of Preparation Example 11 (2.8 mg, 0.00093% wet weight) and a compound of Preparation Example 12 (24.7 mg, 0.0082%).

The obtained Preparation Example 12 compound had the following physicochemical properties and was identified as '3-[[(1R,2S,8aS)-1,2,5,5-tetramethyl-2,3,6,7,8,8a-hexahydronaphthalen-1-yl]methyl]-4-hydroxy-5-(2-phenylethylamino)cyclohexa-3,5-diene-1,2-dione'.

Purple-red, amorphous solid.

$[\alpha]^{23}_D$ −14 (c 0.2, CHC13).

IR (film) $v_{max}$ 3290, 1730, 1650, 1590, 1510, 1460, 1380, 1360, 1220 cm$^{-1}$.

UV (MeOH) $\lambda_{max}$ 336 (log 4.28), 507 nm (2.84).

$^1$H NMR (CDCl$_3$): see [Table 7].

$^{13}$C NMR (CDCl$_3$): see [Table 7].

EIMS m/z (%) 447 (M+, 9), 257 (100), 191 (2), 166 (20), 152 (5), 105 (10), 95 (15); HREIMS m/z 447.2790 [M]$^+$ (calcd for C$_{29}$H$_{37}$NO$_3$, 447.2773).

TABLE 7

| positn | $\delta_C$ | $\delta_H$ (m, J in Hz) | HBMC | NOESY |
|---|---|---|---|---|
| 1 | 30.5 CH$_2$ | 1.85 (m) | | 1b, 2a, 10, 14, 15a |
| | | 0.95 (m) | | 1a, 3b |
| 2 | 22.8 CH$_2$ | 1.49 (m) | | 1a, 1b, 2a, 3b |
| | | 1.32 (m) | | 2a, 3a, 12 |
| 3 | 41.3 CH$_2$ | 1.37 (m) | 2, 11, 12 | 3b |
| | | 1.16 (ddd, 13.5, 13.5, 4.1) | 2, 4, 11, 12 | 2a, 3a, 11 |
| 4 | 36.4 C | | | |
| 5 | 146.5 C | | | |
| 6 | 114.8 CH | 5.38 brs | 4, 8, 7, 10 | 7a, 7b, 11 |
| 7 | 31.6 CH$_2$ | 1.96 (ddd, 17.3, 5.2, 5.2) | 5, 6, 8, 9, 13 | 7b, 8, 13 |
| | | 1.77 (dddd, 17.3, 9.5, 2.6, 2.6) | 5, 6, 8, 13 | 7a, 8, 13, 14 |
| 8 | 36.3 CH | 1.39 (m) | 7, 9, 13 | 7a, 10, 13, 15b |
| 9 | 40.6 C | | | |
| 10 | 41.6 CH | 2.10 (m) | 5 | 1a, 2b, 8, 12, 15b |
| 11 | 29.7 CH$_3$ | 1.03$^b$ (brs) | 3, 4, 5, 12 | 3a, 3b |
| 12 | 28.0 CH$_3$ | 0.95$^b$ (s) | 3, 4, 5, 11 | 2b, 10 |
| 13 | 16.5 CH$_3$ | 0.99$^b$ (d, 6.7) | 7, 8, 9 | 7a, 7b, 8, 14, 15a, 15b |
| 14 | 15.9 CH$_3$ | 0.74$^b$ (s) | 8, 9, 10, 15 | 1a, 1b, 7b, 13, 15a, 15b |
| 15 | 32.7 CH$_2$ | 2.54 (d, 13.4) | 8, 9, 10, 14, 16, 17, 21 | 1a, 13, 14, 15b |
| | | 2.41 (d, 13.4) | 8, 9, 10, 14, 16, 17, 21 | 8, 10, 13, 15a |
| 16 | 114.7 C | | | |
| 17 | 156.5 C | | | |
| 18 | 178.5 C | | | |
| 10 | 91.8 CH | 5.42 (s) | 17, 21 | 22, 23 |
| 20 | 149.9 C | | | |
| 21 | 183.0 C | | | |
| 22 | 44.0 CH$_2$ | 3.44$^a$ (td, 6.9, 6.1) | 20, 23, 24 | 19, 23, 25 |
| 23 | 34.2 CH$_2$ | 2.95$^a$ (t, 6.9) | 22, 24, 25 | 19, 22, 25 |
| 24 | 137.4 C | | | |
| 25 | 128.5$^c$ CH | 7.19$^a$ (d, 7.3) | 23, 27 | 22, 23 |
| 26 | 128.9$^c$ CH | 7.33$^a$ (dd, 7.3, 7.3) | 24, 27 | |
| 27 | 127.0 CH | 7.26 (t, 7.3) | 25 | |
| 20-NH | | 6.54 (brs) | 19, 21 | |

$^a$2H
$^b$3H
$^c$2C

<Preparation Example 13> Preparation of 3-[[(1R, 2S,4aS,8aS)-1,2,4a,5-tetramethyl-2,3,4,7,8,8a-hexahydronaphthalen-1-yl]methyl]-4-hydroxy-5-(2-phenylethylamino)cyclohexa-3,5-diene-1,2-dione A compound of Preparation Example 13 was prepared in the same manner as in Preparation Example 12. The obtained compound (Preparation Example 13) had the following physicochemical properties and was identified as '3-[[(1R,2S,4aS,8aS)-1,2,4a,5-tetramethyl-2,3,4,7,8,8a-hexahydronaphthalen-1-yl]methyl]-4-hydroxy-5-(2-phenylethylamino)cyclohexa-3,5-diene-1,2-dione'.

Purple-red. amorphous solid.

$[\alpha]^{25}_D$+180 (c 0.1, CHCl$_3$).

IR (film) $v_{max}$ 3270, 1730, 1640, 1590, 1510, 1460, 1380, 1210 cm$^{-1}$.

UV (MeOH) $\lambda_{max}$ 335 (log 4.20), 502 nm (2.74).

$^1$H NMR (CDCl$_3$): see [Table 8].

$^{13}$C NMR (CDCl$_3$): see [Table 8].

EIMS m/z (%) 447 (M+, 25), 257 (100), 209 (17), 191 (18), 168 (45), 166 (48), 152 (17), 119 (42), 105 (40);

HREIMS m/z 447.2783 [M]$^+$ (calcd for C$_{29}$H$_{37}$NO$_3$, 447.2773).

TABLE 8

| Pos. | $\delta_C$ | | $\delta_H$ (m, J in Hz) | HMBC | NOESY |
|---|---|---|---|---|---|
| 1 | 19.9 | $CH_2$ | 2.03 (m) | 5 | 1b, 2b, 10, 14, 15a |
| | | | 1.45 (dddd, 12.0, 12.0, 12.0, 6.1) | | 1a, 2a, 12, 14 |
| 2 | 27.0 | $CH_2$ | 1.98 (m) | | 1b, 2a, 2b, 3, 10 |
| | | | 1.81 (m) | | 1a, 2a, 3 |
| 3 | 120.8 | CH | 5.12 (brs) | | 2a, 2b, 11 |
| 4 | 144.1 | C | | | |
| 5 | 38.5 | C | | | |
| 6 | 36.0 | C | 1.62 (ddd, 12.2, 3.1, 3.1) | | 6b, 7 |
| | | | 1.05 (ddd, 12.2, 12.2, 4.8) | | 6a, 7 |
| 7 | 28.0 | $CH_2$ | 1.32$^a$ (m) | | 6a, 6b, 8, 13, 14 |
| 8 | 37.7 | CH | 1.26 (m) | | 7, 10 |
| 9 | 42.7 | C | | | |
| 10 | 47.6 | CH | 1.03 (overlapped) | | 1a, 2b, 8, 15a |
| 11 | 18.2 | $CH_3$ | 1.54$^b$ (brs) | 3, 4, 5 | 3, 12 |
| 12 | 20.1 | $CH_3$ | 1.00$^b$ (s) | 4, 5, 6, 10 | 6a, 6b, 14 |
| 13 | 17.7 | $CH_3$ | 0.95$^b$ (d, 6.3) | 7, 8, 9 | 7, 14 |
| 14 | 17.3 | $CH_3$ | 0.82$^b$ (s) | 8, 9, 10, 15 | 1a, 1b, 8, 12, 13, 15a, 15b |
| 15 | 32.4 | $CH_2$ | 2.56 (d, 13.9) | 8, 9, 14, 16, 17, 21 | 1a, 10, 14, 15b |
| | | | 2.41 (d, 13.9) | 9, 10, 14, 16, 17, 21 | 13, 14, 15a |
| 16 | 113.9 | C | | | |
| 17 | 156.9 | C | | | |
| 18 | 178.3 | C | | | |
| 19 | 91.8 | CH | 5.40 (s) | 17, 21 | 22 |
| 20 | 150.9 | C | | | |
| 21 | 182.8 | C | | | |
| 22 | 44.0 | $CH_3$ | 3.42$^c$ (td, 7.1, 6.7) | 20, 23, 24 | 19, 23, 25, 20-NH |
| 23 | 34.3 | $CH_3$ | 2.95$^c$ (t, 7.1) | 22, 24, 25 | 19, 22, 25, 20-NH |
| 24 | 137.4 | C | | | |
| 25 | 128.6$^c$ | CH | 7.18$^c$ (d, 7.2) | 23, 27 | 22, 23, 26 |
| 26 | 128.9$^c$ | CH | 7.33$^c$ (dd, 7.4, 7.2) | 24, 25 | 25, 27 |
| 27 | 127.1 | CH | 7.26 (t, 7.4) | 25 | 26 |
| 17-OH | | | 8.36 (brs) | | 22, 23 |
| 20-NH | | | 6.46 (brt, 6.7) | | 22, 23 |

$^a$2H,
$^b$3H,
$^c$2C.

<Preparation Example 14> Preparation of 3-[[(1R, 2S,4aS,8aS)-1,2,4a,5-tetramethyl-2,3,4,7,8,8a-hexa-hydronaphthalen-1-yl]methyl]-4-hydroxy-5-(2-methylpropylamino)cyclohexa-3,5-diene-1,2-dione The fraction 2 obtained in Preparation Example 10 was subjected to $C_{18}$ column (MeOH/$H_2O$/$CF_3CO_2H$) and $C_{18}$ HPLC (Luna 5u Phenyl-Hexyl, Phenomenex, 250×10 mm; eluent, MeCN/$H_2O$/$CF_3CO_2H$, 80:20:0.05; flow rate, 2.0 mL/min; UV detection at 300 nm) to obtain a compound of Preparation Example 14 (0.9 mg, 0.00030%), a fraction γ and a fraction δ.

The obtained compound of Preparation Example 14 had the following physicochemical properties and was identified as '3-[[(1R,2S,4aS,8aS)-1,2,4a,5-tetramethyl-2,3,4,7,8,8a-hexahydronaphthalen-1-yl]methyl]-4-hydroxy-5-(2-methylpropylamino)cyclohexa-3,5-diene-1,2-dione'.

Purple-red, amorphous solid.

$[\alpha]^{23}_D$+160 (c 0.1, $CHCl_3$).

IR (film) $\nu_{max}$ 3270, 1730, 1640, 1590, 1510, 1380, 1210 $cm^{-1}$.

UV (MeOH) max 334 (log 4.29), 509 nm (2.86).

$^1$H NMR ($CDCl_3$): see [Table 9].

$^{13}$C NMR ($CDCl_3$): see [Table 9].

EIMS m/z (%) 399 (M+, 8), 209 (100), 191 (3), 166 (11), 152 (9), 107 (9), 95 (22).

HREIMS m/z 399.2790 [M]$^+$ (calcd for $C_{25}H_{37}NO_3$, 399.2773).

TABLE 9

| posim | $\delta_C$ | | $\delta_H$ (m, J in Hz) | HMBC | NOESY |
|---|---|---|---|---|---|
| 1 | 19.9 | $CH_2$ | 2.04 (m) | 2, 3, 5, 9, 10 | 1b, 3, 10, 15a |
| | | | 1.45 (dddd, 12.0, 12.0, 12.0, 6.1) | 2, 5, 10 | 1a, 14 |
| 2 | 27.1 | $CH_2$ | 1.99 (m) | | 1b, 2b |
| | | | 1.86 (m) | | 2a, 3, 10 |
| 3 | 120.8 | CH | 5.12 (brs) | 12 | 1a, 2b, 11 |
| 4 | 144.1 | C | | | |
| 5 | 38.5 | C | | | |
| 6 | 36.0 | $CH_2$ | 1.61 (ddd, 12.7, 3.2, 3.2) | 7 | 6b, 7 |
| | | | 1.04 (m) | | 6a, 7 |
| 7 | 27.9 | $CH_2$ | 1.34$^a$ (m) | 8 | 6a, 6b, 13, 14 |
| 8 | 37.7 | CH | 1.27 (m) | | 10, 13 |
| 9 | 42.6 | C | | | |
| 10 | 47.6 | CH | 1.04 (m) | 1, 2, 5, 9 | 1a, 2b, 8 |
| 11 | 18.1 | $CH_3$ | 1.53$^b$ (brs) | 3, 4, 5, 6 | 3, 12 |

TABLE 9-continued

| posim | $\delta_C$ | | $\delta_H$ (m, J in Hz) | HMBC | NOESY |
|---|---|---|---|---|---|
| 12 | 20.1 | $CH_3$ | 1.00[b] (s) | 4, 5, 6, 10 | 11, 14 |
| 13 | 17.7 | $CH_3$ | 0.96[b] (d, 6.1) | 7, 8, 9 | 7, 8, 15b |
| 14 | 17.3 | $CH_3$ | 0.82[b] (s) | 8, 9, 10, 15 | 1b, 7, 12, 13, 15a, 15b |
| 15 | 32.4 | $CH_2$ | 2.56 (d, 13.9) | 8, 9, 14, 16, 17, 21 | 1a, 14, 15b |
|  |  |  | 2.42 (d, 13.9) | 8, 9, 10, 14, 16, 17, 21 | 13, 14, 15a |
| 16 | 113.9 | C | | | |
| 17 | 157.1 | C | | | |
| 18 | 178.1 | C | | | |
| 19 | 91.6 | CH | 5.37 (s) | 17, 21 | 22 |
| 20 | 150.5 | C | | | |
| 21 | 182.9 | C | | | |
| 22 | 50.3 | $CH_2$ | 2.97[a] (dd, 6.4, 6.4) | 20, 23, 24 | 19, 23, 24, 20-NH |
| 23 | 27.6 | CH | 1.96[a] (m) | 22, 24 | |
| 24 | 20.2[d] | $CH_3$ | 0.98[c] (d, 6.7) | 22, 23 | 22, 23 |
| 20-NH | | | 6.53 (brs) | | 22 |

[a]2H,
[b]3H,
[c]6H,
[d]2C.

<Preparation Example 15> Preparation of 3-[[1R,2S,4aS,8aS)-1,2,4a,5-tetramethyl-2,3,4,7,8,8a-hexahydronaphthalen-1-yl]methyl]-4-hydroxy-5-[[(2S)-2-methylbutyl]amino]cyclohexa-3,5-diene-1,2-dione The fraction γ obtained in Preparation Example 14 was purified by $C_{18}$ HPLC (Luna 5u C18 (2), Phenomenex, 250×10 mm; MeOH/$H_2O$/$Et_2NH$, 70:30:0.1; flow rate, 2.0 mL/min; UV detection at 300 nm) to obtain a compound of Preparation Example 15 (1.4 mg, 0.00047%) and a compound of Preparation Example 16 (4.0 mg, 0.0013%).

The compound of Preparation Example 15 had the following physicochemical properties and was identified as '3-[[(1R,2S,4 aS,8aS)-1,2,4a,5-tetramethyl-2,3,4,7,8,8a-hexahydronaphthalen-1-yl]methyl]-4-hydroxy-5-[[(2S)-2-methylbutyl]amino]cyclohexa-3,5-diene-1,2-dione'.

Purple-red, amorphous solid.
$[\alpha]^{21}_D$+136 (c 0.25, $CHCl_3$).
IR (film) $v_{max}$ 3270, 1680, 1650, 1590, 1510, 1450, 1380, 1210 $cm^{-1}$.
UV (MeOH) $\lambda_{max}$ 336 (log 4.09), 505 nm (2.67).
NMR ($CDCl_3$): see [Table 10].
$^{13}$C NMR ($CDCl_3$): see [Table 10].
HREIMS mlz 413.2940 [M]$^+$ (calcd for $C_{26}H_{39}NO_3$, 413.2930).

TABLE 10

| Pos. | $\delta_C$ | | $\delta_H$ (m, J in Hz) | HMBC | NOESY |
|---|---|---|---|---|---|
| 1 | 19.9 | $CH_2$ | 2.04 (m) | 2, 3, 5, 10 | 1b, 10, 15a |
|  |  |  | 1.47 (m) | | 12, 14 |
| 2 | 27.1 | $CH_2$ | 1.99 (m) | | 1b, 2b |
|  |  |  | 1.85 (m) | | 2a, 10 |
| 3 | 120.8 | CH | 5.12 (brs) | | 2a, 2b, 11 |
| 4 | 144.1 | C | | | |
| 5 | 38.5 | C | | | |
| 6 | 36.0 | $CH_2$ | 1.62 (ddd, 12.7, 3.0, 3.0) | | 6b, 7, 11, 12 |
|  |  |  | 1.04 (m) | | 6a |
| 7 | 27.9 | $CH_2$ | 1.35[a] (m) | | 6a, 6b, |
| 8 | 37.7 | CH | 1.27 (m) | | 10, 13 |
| 9 | 42.7 | C | | | |
| 10 | 47.6 | CH | 1.04 (m) | 2, 5, 9 | 1a, 2b, 8 |
| 11 | 18.1 | $CH_3$ | 1.53[b] (brs) | 3, 4, 5 | 3, 6a |
| 12 | 19.9 | $CH_3$ | 0.99[b] (s) | 4, 5, 6 | 6a, 14 |
| 13 | 17.7 | $CH_3$ | 0.96[b] (d, 6.8) | 7, 8 | 8, 14, 15b |
| 14 | 17.3 | $CH_3$ | 0.82[b] (s) | 8, 9, 10, 15 | 1b, 7, 12, 13, 15a, 15b |
| 15 | 32.4 | $CH_2$ | 2.55 (d, 13.9) | 8, 9, 14, 16, 17, 21 | 1a, 14, 15b |
|  |  |  | 2.42 (d, 13.9) | 8, 9, 10, 14, 16, 17, 21 | 13, 14, 15a |
| 16 | 113.8 | C | | | |
| 17 | 157.2 | C | | | |
| 18 | 178.1 | C | | | |
| 19 | 91.5 | CH | 5.37 (s) | 17, 21 | 22a, 22b, 23 |
| 20 | 150.6 | C | | | |
| 21 | 182.9 | C | | | |
| 22 | 48.7 | $CH_2$ | 3.08 (ddd, 13.2, 6.5, 6.5) | 20, 23, 24, 26 | 19, 26, 20-NH |
|  |  |  | 2.95 (ddd, 13.2, 6.7, 6.7) | 20, 23, 24, 26 | 19, 26, 20-NH |
| 23 | 34.0 | CH | 1.74 (m) | 22, 24 | 22a, 22b, 24a, 26 |
| 24 | 27.2 | $CH_3$ | 1.44 (m) | 23, 26 | 23, 24b, 25 |
|  |  |  | 1.24 (m) | 26 | 24a, 25 |

TABLE 10-continued

| Pos. | $\delta_C$ | | $\delta_H$ (m, J in Hz) | HMBC | NOESY |
|---|---|---|---|---|---|
| 25 | 11.1 | $CH_3$ | 0.93[b] (t, 7.4) | 23, 24 | 24a, 24b |
| 26 | 17.4 | $CH_3$ | 0.96[b] (d, 6.8) | 22, 23, 24 | 22a, 22b, 23 |
| 20-NH | | | 6.53 (brs) | | 22a, 22b |

[a]2H,
[b]3H.

<Preparation Example 16> Preparation of 3-[[(1R, 2S,4aS,8aS)-1,2,4a,5-tetramethyl-2,3,4,7,8,8a-hexahydronaphthalen-1-yl]methyl]-4-hydroxy-5-(3-methylbutylamino)cyclohexa-3,5-diene-1,2-dione A compound of Preparation Example 16 was prepared in the same manner as in Preparation Example 15. It had the following physicochemical properties and was identified as '3-[[(1R,2S,4aS,8aS)-1,2,4a,5-tetramethyl-2,3,4,7,8,8a-hexahydronaphthalen-1-yl]methyl]-4-hydroxy-5-(3-methylbutylamino)cyclohexa-3,5-diene-1,2-dione'.

Purple-red, amorphous solid.
$[\alpha]^{21}_D$+124 (c 0.25, $CHCl_3$).
IR (film) $\nu_{max}$ 3270, 1680, 1640, 1590, 1510, 1380, 1210 $cm^{-1}$.
UV (MeOH) $\lambda_{max}$ 336 (log 4.17), 515 nm (2.55).
$^1$H NMR ($CDCl_3$): see [Table 11].
$^{13}$C NMR ($CDCl_3$): see [Table 11].
EIMS m/z (%) 413 (M+, 7), 223 (100), 191 (3), 166 (8), 152 (9), 107 (8), 95 (18);
HREIMS m/z 413.2947 [M]$^+$ (calcd for $C_{26}H_{39}NO_3$, 413.2930).

<Preparation Example 17> Preparation of 3-[[(1R, 2S,8aS)-1,2,5,5-tetramethyl-2,3,6,7,8,8a-hexahydronaphthalen-1-yl]methyl]-4-hydroxy-5-[[(2S)-2-methylbutyl]amino]cyclohexa-3,5-diene-1,2-dione The fraction δ obtained in Preparation Example 14 was refractionated by $C_{18}$ HPLC (Luna 5u Phenyl-Hexyl, 250× 10 mm; MeOH/$H_2O$/$Et_2NH$, 65:35:0.1; flow rate, 2.0 mL/min; UV detection at 300 nm) to obtain a compound of Preparation Example 17 (0.7 mg, 0.00023%) and a compound of Preparation Example 18 (1.6 mg, 0.00053%).

The obtained Preparation Example 17 compound had the following physicochemical properties and was identified as '3-[[(1R,2S,8aS)-1,2,5,5-tetramethyl-2,3,6,7,8,8a-hexahydronaphthalen-1-yl]methyl]-4-hydroxy-5-[[(2S)-2-methylbutyl]amino]cyclohexa-3,5-diene-1,2-dione'.

Purple-red, amorphous solid.
$[\alpha]^{23}_D$-42 (c 0.25, $CHCl_3$).
IR (film) $\nu_{max}$ 3290, 1680, 1650, 1590, 1520, 1460, 1390, 1200 $cm^{-1}$.
UV (MeOH) $\lambda_{max}$ 338 (log 4.06), 511 nm (2.63).
$^1$H NMR ($CDCl_3$): see [Table 12].
$^{13}$C NMR ($CDCl_3$): see [Table 12].

TABLE 11

| Pos. | $\delta_C$ | | $\delta_H$ (m, J in Hz) | HMBC | NOESY |
|---|---|---|---|---|---|
| 1 | 20.1 | $CH_2$ | 2.03 (m) | 2, 3, 5, 9, 10 | 1b, 15a |
| | | | 1.44 (dddd, 12.1, 12.1, 12.1, 6.2) | 2, 5, 10 | 1a, 8 |
| 2 | 27.0 | $CH_2$ | 1.98 (ddd, 17.5, 5.3, 5.3) | | 2b, 3 |
| | | | 1.85 (m) | | 2a, 3 |
| 3 | 120.7 | CH | 5.10 (brs) | 11 | 2a, 2b, 11 |
| 4 | 144.0 | C | | | |
| 5 | 38.4 | C | | | |
| 6 | 35.9 | $CH_2$ | 1.60 (ddd, 12.8, 3.3, 3.3) | | 6b, 7 |
| | | | 1.03 (m) | | 6a, 8 |
| 7 | 27.9 | $CH_2$ | 1.33[a] (m) | 5, 6, 8, 9 | |
| 8 | 37.6 | CH | 1.25 (m) | 14 | 1b |
| 9 | 42.6 | C | | | |
| 10 | 47.5 | CH | 1.03 (m) | | 8 |
| 11 | 18.1 | $CH_3$ | 1.52[b] (brs) | 3, 4, 5 | 3, 12 |
| 12 | 19.8 | $CH_3$ | 0.98[b] (s) | 4, 5, 6, 10 | 1b, 6a, 14 |
| 13 | 17.7 | $CH_3$ | 0.94[b] (d, 6.2) | 7, 9 | 7, 15b |
| 14 | 17.2 | $CH_3$ | 0.81[b] (s) | 8, 9, 10, 15 | 1b, 8, 12, 15a, 15b |
| 15 | 32.4 | $CH_2$ | 2.54 (d, 14.0) | 8, 9, 14, 16, 17, 21 | 1a, 14, 15a |
| | | | 2.41 (d, 14.0) | 8, 9, 10, 14, 16, 17, 21 | 13, 14, 15b |
| 16 | 113.8 | C | | | |
| 17 | 157.2 | C | | | |
| 18 | 178.0 | C | | | |
| 19 | 91.5 | CH | 5.37 (s) | 17, 21 | 22, 23, 25 |
| 20 | 150.3 | C | | | |
| 21 | 182.8 | C | | | |
| 22 | 41.1 | $CH_2$ | 3.15[a] (dt, 7.3, 6.6) | 20, 23, 24 | 19, 23, 25 |
| 23 | 36.8 | $CH_2$ | 1.55[b] (td, 7.3, 6.7) | 22, 24, 25 | 19, 22, 25 |
| 24 | 25.9 | CH | 1.66 (d sept, 6.7, 6.7) | 23, 25 | 25 |
| 25 | 22.3[d] | $CH_3$ | 0.93[c] (d, 6.7) | 23, 24 | 19, 23, 24 |
| 17-OH | | | 7.92 (brs) | | |
| 20-NH | | | 6.46 (brs) | 19, 21 | 22 |

[a]2H,
[b]3H,
[c]6H,
[d]2C.

EIMS m/z (%) 413 (M+, 15), 223 (100), 191 (10), 168 (15), 166 (14), 152 (16), 119 (18).

HREIMS m/z 413.2916 [M]+ (calcd for $C_{26}H_{39}NO_3$, 413.2930).

TABLE 12

| Pos. | $\delta_C$ | $\delta_H$ (m, J in Hz) | HMBC | NOESY |
|---|---|---|---|---|
| 1 | 30.6 CH$_2$ | 1.87 (m) | | 1b, 2a, 2b, 10, 14, 15a |
|   |   | 0.96 (m) | | 1a |
| 2 | 22.8 CH$_2$ | 1.50 (m) | | 1a, 1b, 2b |
|   |   | 1.40 (m) | | 2a, 3a, 3b |
| 3 | 41.4 CH$_2$ | 1.38 (m) | | 2a, 2b, 3b |
|   |   | 1.16 (ddd, 13.1, 13.1, 4.4) | | 2a, 2b, 3a |
| 4 | 36.3 C | | | |
| 5 | 146.5 C | | | |
| 6 | 114.9 CH | 5.40 (brs) | 4, 7, 8, 10 | 7a, 7b, 11 |
| 7 | 31.6 CH$_2$ | 1.97 (ddd, 17.6, 4.3, 4.3) | 5 | 7b, 8, 13 |
|   |   | 1.78 (m) | 5, 6 | 6, 7a |
| 8 | 36.4 CH | 1.40 (m) | | 7a, 10, 12 |
| 9 | 40.6 C | | | |
| 10 | 41.6 CH | 2.11 (m) | | 1a, 8, 12, 15b |
| 11 | 29.7 CH$_3$ | 1.03$^b$ (brs) | 3, 4, 5, 12 | 3a, 3b |
| 12 | 28.0 CH$_3$ | 0.96$^b$ (s) | 3, 4, 5, 11 | 8, 10 |
| 13 | 16.6 CH$_3$ | 1.00$^b$ (d, 6.7) | 7, 8, 9 | 7a, 8, 14, 15a, 15b |
| 14 | 15.9 CH$_3$ | 0.74$^b$ (s) | 8, 9, 10, 15 | 1a, 7b, 13, 15a, 15b |
| 15 | 32.8 CH$_2$ | 2.56 (d, 13.5) | 8, 9, 10, 14, 16, 17, 21 | 1a, 13, 14, 15b |
|   |   | 2.42 (d, 13.5) | 8, 9, 10, 14, 16, 17, 21 | 8, 10, 13, 14, 15a |
| 16 | 114.5 C | | | |
| 17 | 156.7 C | | | |
| 18 | 178.3 C | | | |
| 19 | 91.5 CH | 5.40 (s) | 17, 21 | 22a, 22b |
| 20 | 150.5 C | | | |
| 21 | 183.1 C | | | |
| 22 | 48.7 CH$_2$ | 3.11 (ddd, 13.1, 6.4, 6.4) | 20, 23, 24, 26 | 19, 22b, 23, 26 |
|   |   | 3.00 (ddd, 13.1, 6.7, 6.7) | 20, 23, 24, 26 | 19, 22a, 23, 26 |
| 23 | 34.0 CH$_2$ | 1.76 (m) | 22, 24, 25, 26 | 22a, 22b, 24a, 26 |
| 24 | 27.2 CH | 1.44 (m) | 22, 23, 25, 26 | 23, 24b, 25 |
|   |   | 1.23 (m) | 22, 23, 25, 26 | 24a |
| 25 | 11.1 CH$_3$ | 0.93$^b$ (t, 7.5) | 23, 24 | 24a |
| 26 | 17.3 CH$_3$ | 0.97$^b$ (d, 6.7) | 22, 23, 24 | 22a, 22b, 23 |
| 20-NH | | 6.58 (brs) | | |

$^a$2H,
$^b$3H.

<Preparation Example 18> Preparation of 3-[[(1R, 2S,8aS)-1,2,5,5-tetramethyl-2,3,6,7,8,8a-hexahydronaphthalen-1-yl]methyl]-4-hydroxy-5-(3-methylbutylamino)cyclohexa-3,5-diene-1,2-dione A compound of Preparation Example 18 was prepared in the same manner as in Preparation Example 17. It had the following physicochemical properties and was identified as '3-[[(1R,2S,8aS)-1,2,5,5-tetramethyl-2,3,6,7,8,8a-hexahydronaphthalen-1-yl]methyl]-4-hydroxy-5-(3-methylbutylamino)cyclohexa-3,5-diene-1,2-dione' compound.

Purple-red, amorphous solid.

$[\alpha]^{21}_D$ –38 (c 0.2, CHCl$_3$).

IR (film) $\nu_{max}$ 3270, 1680, 1650, 1590, 1510, 1460, 1380, 1200 cm$^{-1}$.

UV (MeOH) $\lambda_{max}$ 338 (log 4.21), 515 nm (2.63).

$^1$H NMR (CDCl$_3$): see [Table 13].

$^{13}$C NMR (CDCl3): see [Table 13].

EIMS m/z (%) 413 (M+, 24), 223 (100), 191 (13), 166 (20), 152 (17), 119 (20).

HREIMS m/z 413.2947 [M]+ (calcd for $C_{29}H_{37}NO_3$, 413.2930).

TABLE 13

| Pos. | $\delta_C$ | $\delta_H$ (m, J in Hz) | HMBC | NOESY |
|---|---|---|---|---|
| 1 | 30.6 CH$_2$ | 1.87 (m) | | 1b, 2a, 2b, 10, 14, 15a |
|   |   | 0.93 (m) | | 1a, 2a, 2b, 14 |
| 2 | 22.8 CH$_2$ | 1.50 (m) | | 1a, 1b, 2b, 3a, 3b |
|   |   | 1.38 (m) | | 3a, 3b, 12 |
| 3 | 41.4 CH$_2$ | 1.38 (m) | | 2a, 2b |
|   |   | 1.16 (ddd, 13.0, 13.0, 4.2) | | 2a, 2b |
| 4 | 36.4 C | | | |
| 5 | 146.5 C | | | |
| 6 | 114.9 CH | 5.39 (brs) | 4, 7, 8, 10 | 7a, 7b, 11 |
| 7 | 31.6 CH$_2$ | 1.98 (m) | | 6, 7b, 8, 13 |
|   |   | 1.77 (m) | 8 | 6, 7a, 13, 14 |
| 8 | 36.3 CH | 1.38 (m) | | 7a, 7b, 10, 15b |
| 9 | 40.6 C | | | |
| 10 | 41.6 CH | 2.11 (m) | | 1a, 8, 12, 15a |
| 11 | 29.7 CH$_3$ | 1.03$^b$ (brs) | 3, 4, 5, 12 | 6 |
| 12 | 28.0 CH$_3$ | 0.95$^b$ (s) | 3, 4, 5, 11 | 2b, 10 |

TABLE 13-continued

| Pos. | $\delta_C$ | | $\delta_H$ (m, J in Hz) | HMBC | NOESY |
|---|---|---|---|---|---|
| 13 | 16.6 | CH$_3$ | 0.99$^b$ (d, 6.7) | 7, 8, 9 | 7a, 7b, 8, 14, 15a, 15b |
| 14 | 16.0 | CH$_3$ | 0.74$^b$ (s) | 8, 9, 10, 15 | 1a, 1b, 7b, 13, 15a, 15b |
| 15 | 32.7 | CH$_2$ | 2.55 (d, 13.4) | 8, 9, 10, 14, 16, 17, 21 | 1a, 13, 14, 15b |
|  |  |  | 2.42 (d, 13.4) | 8, 9, 10, 14, 16, 17, 21 | 8, 10, 13, 14, 15a |
| 16 | 114.5 | C |  |  |  |
| 17 | 156.7 | C |  |  |  |
| 18 | 178.3 | C |  |  |  |
| 19 | 91.5 | CH | 5.39 (s) | 17, 21 |  |
| 20 | 150.1 | C |  |  |  |
| 21 | 183.1 | C |  |  |  |
| 22 | 41.7 | CH$_2$ | 3.18$^a$ (td, 6.7, 6.3) | 20, 23, 24, | 23, 25 |
| 23 | 36.9 | CH$_2$ | 1.57$^a$ (dt, 6.7, 6.7) | 22, 24, 25 | 22, 25 |
| 24 | 25.9 | CH | 1.68 (d, sept, 6.7, 6.7) | 25 | 25 |
| 25 | 22.3$^d$ | CH$_3$ | 0.95$^c$ (d, overlapped) | 23, 24 | 22, 23, 24 |
| 20-NH |  |  | 6.43 (brs) |  |  |

$^a$2H,
$^b$3H,
$^c$6H,
$^d$2C.

<Preparation Example 19> Preparation of 3-[[(1R,2S,4aS,8aS)-1,2,4a-trimethyl-5-methylidene-3,4,6,7,8,8a-hexahydro-2H-naphthalen-1-yl]methyl]-4-hydroxy-5-[[(2S)-2-methylbutyl]amino]cyclohexa-3,5-diene-1,2-dione A sponge (Spongiidae SS-265) was obtained as described in the literature 'Yohei Takahashi et al., 2010' and extracted. Briefly, an extract was prepared by adding MeOH (4.3 and 3.2 L) to sponge SS-265 (1.4 kg, wet weight). The MeOH extract (68.4 g) was fractionated with CHCl$_3$ and H$_2$O. The CHCl$_3$-soluble substances (2.3 g) were subjected to silica gel column (n-hexane/EtOAc), C$_{18}$ column (MeOH/H$_2$O), silica gel column (n-hexane/acetone) and C$_{18}$ HPLC (Wakosil-II 5C18AR, 250×10 mm; eluent, MeCN/H$_2$O/CF$_3$CO$_2$H, 90:10:0.1; flow rate, 2.0 mL/min; UV detection at 300 nm and Luna 5u C$_{18}$(2), 250×10 mm; MeOH/H$_2$O/Et$_2$NH, 70:30:0.1; flow rate, 2.0 mL/min; UV detection at 300 nm) repeatedly to obtain a compound of Preparation Example 19 (1.8 mg, 0.00013%).

The obtained Preparation Example 19 compound had the following physicochemical properties and was identified as '3-[[(1R,2S,4aS,8aS)-1,2,4a-trimethyl-5-methylidene-3,4,6,7,8,8a-hexahydro-2H-naphthalen-1-yl]methyl]-4-hydroxy-5-[[(2S)-2-methylbutyl]amino]cyclohexa-3,5-diene-1,2-dione'.

Purple-red, amorphous solid.
[α]$^{22}_D$+33 (c 0.2, CHCl$_3$).
IR (film) $v_{max}$ 3280, 1640, 1590, 1510, 1380, 1200 cm$^{-1}$.
UV (MeOH) $\lambda_{max}$ 501 (log 2.88), 327 (4.17), 243 (3.86), 208 nm (4.25).
$^1$H NMR (CDCl$_3$): see [Table 14].
$^{13}$C NMR (CDCl$_3$): see [Table 14].
EIMS m/z (%) 413 (M+, 15), 223 (100), 191 (3), 166 (10), 152 (10), 95 (10).
HREIMS m/z 413.2934 [M]$^+$ (calcd for C$_{26}$H$_{39}$NO$_3$, 413.2930).

TABLE 14

| Pos. | $\delta_C$ | | $\delta_H$ (m, J in Hz) | HMBC | NOESY |
|---|---|---|---|---|---|
| 1 | 23.2 | CH$_2$ | 2.09 (m) | 3, 5 | 1b, 8, 10, 15a |
|  |  |  | 1.43 (m) |  | 1a, 2b, 3a |
| 2 | 28.7 | CH$_2$ | 1.84 (m) |  | 1a, 2b, 3a, 3b |
|  |  |  | 1.14 (m) |  | 2a, 3b |
| 3 | 33.0 | CH$_2$ | 2.32 (ddd, 13.7, 13.7, 5.4) | 2, 4, 11 | 1b, 2a, 3b, 12 |
|  |  |  | 2.05 (m) | 1, 5 | 2a, 2b, 3a, 11a |
| 4 | 160.5 | C |  |  |  |
| 5 | 40.4 | C |  |  |  |
| 6 | 36.7 | CH$_2$ | 1.51 (m) | 5, 7, 8, 10 | 6b, 11b |
|  |  |  | 1.36 (m) |  | 6a, 11b |
| 7 | 28.0 | CH$_2$ | 1.39$^a$ (m) |  | 12, 14 |
| 8 | 37.9 | CH | 1.18 (m) |  | 10 |
| 9 | 42.9 | C |  |  |  |
| 10 | 50.0 | CH | 0.78 (dd, 11.6, 1.8) | 1, 5, 8, 9, 12, 14, 15 | 1a, 2b, 6b, 8, 15a |
| 11 | 102.5 | CH$_2$ | 4.43 (s) | 3, 4, 5 | 3b |
|  |  |  | 4.42 (s) | 3, 4, 5 | 6a, 6b |
| 12 | 20.5 | CH$_3$ | 1.04$^b$ (s) | 3, 4, 6, 10 | 3a, 7, 14 |
| 13 | 17.9$^c$ | CH$_3$ | 0.96$^{b,c}$ (d, 6.4) | 7, 8, 9 | 7, 15b |
| 14 | 17.2 | CH$_3$ | 0.82$^b$ (s) | 8, 9, 10, 15 | 7, 12, 15a, 15b |
| 15 | 32.5 | CH$_2$ | 2.48 (d, 14.0) | 8, 9, 10, 14, 16, 17, 21 | 1a, 10, 14, 15b |
|  |  |  | 2.39 (d, 14.0) | 8, 9, 10, 14, 16, 17, 21 | 8, 13, 14, 15a |
| 16 | 113.5 | C |  |  |  |
| 17 | 157.3 | C |  |  |  |
| 18 | 178.1 | C |  |  |  |
| 19 | 91.6 | CH | 5.36 (s) | 17, 21 | 22a, 22b, 23 |
| 20 | 150.5 | C |  |  |  |
| 21 | 182.9 | C |  |  |  |

TABLE 14-continued

| Pos. | $\delta_C$ | | $\delta_H$ (m, J in Hz) | HMBC | NOESY |
|---|---|---|---|---|---|
| 22 | 48.7 | $CH_2$ | 3.08 (ddd, 13.2, 6.6, 6.6) | 20, 23, 24, 26 | 19, 22b, 23, 24a, 20-NH |
|  |  |  | 2.95 (ddd, 13.2, 6.7, 6.7) | 20, 23, 24, 26 | 19, 22a, 23, 20-NH |
| 23 | 34.0 | $CH_2$ | 1.75 (m) | 22, 24, 25, 26 | 22a, 22b, 24a, 24b, 25, 26 |
| 24 | 27.2 | CH | 1.45 (m) | 22, 23, 25, 26 | 22a, 23, 24b, 25 |
|  |  |  | 1.23 (m) | 22, 23, 25, 26 | 23, 24a |
| 25 | 11.1 | $CH_3$ | $0.93^b$ (t, 7.4) | 23, 24 | 23, 24a |
| 26 | $17.4^c$ | $CH_3$ | $0.96^{b,c}$ (d, 6.8) | 22, 23, 24 | 23 |
| 20-NH |  |  | 6.51 (brs) |  | 22a, 22b, 23, 26 |

[a]2H,
[b]3H,
[c]interchangeable.

<Preparation Example 20> Preparation of 2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien1-yl]amino]ethanesulfonic Acid A sponge (Spongiidae SS-1208) was obtained as described in the literature 'Yohei Takahashi et al., 2010' and extracted. Briefly, an extract was prepared by adding MeOH (3×0.8 L) and MeOH/toluene (3:1, 1×0.8 L) to sponge SS-1208 (0.4 kg, wet weight). The extract mixture (15.9 g) was fractionated with $CHCl_3$ and $H_2O$ (3×500 mL). The $CHCl_3$-soluble fraction (2.7 g) was subjected to silica gel column (n-hexane/EtOAc and $CHCl_3$/MeOH), $C_{18}$ column (MeOH/$H_2O$/$CF_3CO_2H$) and $C_{18}$ HPLC (Luna 5u Phenyl-Hexyl, 250×10 mm; eluent, MeCN/$H_2O$/$CF_3CO_2H$, 70:30:0.1; flow rate, 2.0 mL/min; UV detection at 300 nm and Wakosil-II 5C18AR, 250×10 mm; eluent, MeCN/$H_2O$/$CF_3CO_2H$, 75:25:0.1; flow rate, 2.0 mL/min; UV detection at 300 nm) repeatedly to obtain a compound of Preparation Example 20 (0.8 mg, 0.00020%).

The obtained Preparation Example 20 compound had the following physicochemical properties and was identified as '2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien-1-yl]amino]ethanesulfonic acid'.

Purple-red, amorphous solid.
$[\alpha]^{22}_D$ +38 (c 0.2, MeOH).
IR (KBr) $\nu_{max}$ 3450, 1640, 1600, 1530, 1380, 1210 $cm^{-1}$.
UV (MeOH) $\lambda_{max}$ 237 (log 2.8), 345 (4.00), 513 nm (2.47).
$^1$H NMR (DMSO-$d_6$): see [Table 15].
$^{13}$C NMR (DMSO-$d_6$): see [Table 15].
ESIMS (neg) m/z 450 [M–H]$^-$.
HRESIMS (neg) m/z 450.1955 [M–H]$^-$ (calcd for $C_{23}H_{32}NO_6S$, 450.1950).

TABLE 15

| Pos. | $\delta_C$ | | $\delta_H$ (m, J in Hz) | HMBC | NOESY |
|---|---|---|---|---|---|
| 1 | 19.4 | $CH_2$ | 1.99 (m) |  | 1b, 15a |
|  |  |  | 1.33 (m) |  | 1a, 2, 12, 14 |
| 2 | 26.3 | $CH_2$ | $1.88^a$ (m) |  | 1b, 10 |
| 3 | 120.8 | $CH_2$ | 5.05 (brs) | 12 | 2 |
| 4 | 143.1 | C |  |  |  |
| 5 | 37.8 | C |  |  |  |
| 6 | 35.4 | C | 1.53 (m) |  | 6b, 7, 12 |
|  |  |  | 0.96 (m) |  | 6a |
| 7 | 27.5 | $CH_2$ | $1.27^a$ (m) |  | 6a, 13 |
| 8 | 37.1 | CH | 1.22 (m) |  | 13, 14 |
| 9 | 41.8 | C |  |  |  |
| 10 | 47.0 | CH | 0.96 (m) | 14 | 2, 15b |
| 11 | 17.9 | $CH_3$ | $1.47^b$ (brs) | 3, 4, 5 |  |
| 12 | 19.9 | $CH_3$ | $0.93^b$ (s) | 3, 4, 6, 10 | 1b, 6a, 14 |
| 13 | 17.8 | $CH_3$ | $0.90^b$ (d, 6.0) | 7, 8, 9 | 7, 8 |
| 14 | 17.2 | $CH_3$ | $0.74^b$ (s) | 8, 9, 10, 15 | 1b, 8, 12, 15a |
| 15 | 32.0 | $CH_2$ | 2.41 (d, 13.6) | 16, 17, 21 | 1a, 15b |
|  |  |  | 2.30 (d, 13.6) | 9, 10, 16, 17, 21 | 10, 15a |
| 16 | 113.6 | C |  |  |  |
| 17 | $158.8^c$ | C |  |  |  |
| 18 | 178.0 | C |  |  |  |
| 19 | 91.6 | CH | 5.26 (s) | 17, 21 | 22, 23 |
| 20 | $d$ | C |  |  |  |
| 21 | $182.7^c$ | C |  |  |  |
| 22 | $39.2^c$ | $CH_2$ | $3.33^a$ (overlapped) | 23 |  |
| 23 | 48.0 | $CH_2$ | $2.69^a$ (brt, 6.4) | 22 | 19, 20-NH |
| 20-NH |  |  | 7.96 (brs) |  | 23 |

[a]2H,
[b]3H,
[c]assigned from HMBC spectrum.
[d]not observed.

<Preparation Example 21> Preparation of methyl 3-[[(1R,2S,4aS,8aS)-1,2,4a-trimethyl-5-methyl-idene-3,4,6,7,8,8a-hexahydro-2H-naphthalen-1-yl]methyl]-4-hydroxybenzoate After freeze-drying a sponge (*Dactylospongia elegans*), the freeze-dried sponge (2.6 kg, wet weight) was chopped and immersed in MeOH overnight to prepare an extract. The MeOH extract was fractionated with hexane, 90% methanol, n-BuOH and $H_2O$. The 90% methanol fraction was evaporated under reduced pressure to obtain 12 g of a 90% MeOH extract. 2 g of the 90% MeOH extract was separated by $SiO_2$ column (hexane-AcOEt-acetone-MeOH) to obtain three fractions, Fr. A (0.42 g), Fr. B (0.73 g) and Fr. C (0.83 g). Among the fractions, Fr. A and Fr. B were separated by ODS column (MeOH—$H_2O$) or HPLC (Cosmosil 5SL, hexane-AcOEt=7:1) to obtain a compound of Preparation Example 21 (20 mg, 1%) and a compound of Preparation Example 22 (17 mg, 0.85%).

The obtained Preparation Example 21 compound had the following physicochemical properties and was identified as 'methyl 3-[[(1R,2S,4aS,8aS)-1,2,4a-trimethyl-5-methyl-idene-3,4,6,7,8,8a-hexahydro-2H-naphthalen-1-yl]methyl]-4-hydroxybenzoate'.

White solid.

$[\alpha]^{27}_D$+17.3 (c 0.12, $CHCl_3$).

$^1$H NMR (500 MHz, $CDCl_3$) δ: 7.77 (1H, s), 7.77-7.74 (1H, m), 6.77 (1H, d, J=8.0 Hz), 6.01 (1H, s), 4.41 (1H, s), 4.36 (1H, s), 3.87 (3H, s), 2.68 (1H, d, J=14.3 Hz), 2.64 (1H, d, J=14.3 Hz), 2.33 (1H, td, J=13.7, 5.2 Hz), 2.08 (2H, d, J=13.7 Hz), 1.93-1.89 (1H, m), 1.61-1.56 (1H, m), 1.47 (1H, dt, J=12.2, 3.2 Hz), 1.41-1.38 (3H, m), 1.31-1.27 (1H, m), 1.22-1.19 (1H, m), 1.06 (3H, s), 1.02 (3H, d, J=6.9 Hz), 0.96 (1H, dd, J=12.0, 1.7 Hz), 0.88 (3H, s).

$^{13}$C NMR (125 MHz, $CDCl_3$) δ: 167.6, 160.0, 159.2, 135.0, 129.3, 125.2, 121.6, 115.3, 102.8, 52.0, 48.0, 42.0, 40.2, 37.0, 36.5, 36.3, 33.0, 27.8, 27.7, 23.2, 20.5, 17.62, 17.59.

IR (KBr): 3341, 1686, 1601, 1426, 1287 $cm^{-1}$.

MS (ESI-TOF) m/z: 379 [M+Na]$^+$.

HRMS (ESI-TOF) m/z: 379.2249 (calcd for $C_{23}H_{32}O_3Na$; found: 379.2266).

<Preparation Example 22> Preparation of methyl 3-[[(1S,2R,4aR,8aR)-1,2,4a-trimethyl-5-methyl-idene-3,4,6,7,8,8a-hexahydro-2H-naphthalen-1-yl]methyl]-4,5-dihydroxybenzoate A compound of Preparation Example 22 was prepared in the same manner as in Preparation Example 21. It had the following physicochemical properties and was identified as 'methyl 3-[[(1 S,2R,4aR,8aR)-1,2,4a-trimethyl-5-methyl-idene-3,4,6,7,8,8a-hexahydro-2H-naphthalen-1-yl]methyl]-4,5-dihydroxybenzoate'.

White solid.

$[\alpha]^{26}_D$+10.4 (c 0.19, $CHCl_3$).

$^1$H NMR (500 MHz, $CDCl_3$) δ: 7.49 (1H, d, J=2.0 Hz), 7.40 (1H, d, J=2.0 Hz), 5.90 (2H, S), 4.41 (1H, s), 4.37 (1H, s), 3.87 (3H, s), 2.68 (1H, d, J=14.3 Hz), 2.65 (1H, d, J=14.3 Hz), 2.34 (1H, td, J=13.7, 5.0 Hz), 2.09 (2H, d, J=14.3 Hz), 1.93-1.91 (1H, m), 1.60-1.55 (1H, m), 1.47 (1H, dt, J=11.6, 2.7 Hz), 1.43-1.35 (3H, m), 1.33-1.19 (2H, m), 1.06 (3H, s), 1.03 (3H, d, J=6.3 Hz), 0.96 (1H, d, J=11.5 Hz), 0.88 (3H, s).

$^{13}$C NMR (125 MHz, $CDCl_3$) δ: 167.7, 160.1, 148.7, 142.3, 127.4, 125.2, 120.3, 114.0, 102.8, 52.1, 48.0, 42.1, 40.2, 37.0, 36.5, 36.3, 33.0, 27.9, 27.7, 23.2, 20.6, 17.64, 17.59.

IR (KBr): 3341, 1686, 1601, 1426, 1287 $cm^{-1}$.

MS (ESI-TOF) m/z: 395 [M+Na]$^+$.

HRMS (ESI-TOF) m/z: 395.2198 (calcd for $C_{23}H_{32}O_4Na$; found: 395.2214).

<Preparation Example 23> Preparation of (−)-(1R,4aS,8aS)-1β,2β,4β,-trimethyl-1α[(2',5'-dimethoxy-phenyl)methyl]-5-exo-methylene-(3H)-1,4,4a,5,6,7,8,8aα-octahydronaphthalene After adding anhydrous 95% potassium tert-butoxide (217 mg, 1.93 mmol) to 7.5 mL of benzene, a suspension was prepared by stirring the same. Then, 657 mg (0.62 mmol) of methyltriphenylphosphonium bromide was added. The prepared light yellow solution was heated for 30 minutes under reflux. A heated ylide solution was added dropwise to a solution of 212 mg (0.62 mmol) of the ketone (−)-(1R,4aS,8aS)-1β,2β,4aβ-trimethyl-1α[(2',5'-dimethoy-phenyl)methyl]-1,2,3,4,4a,5,6,7,8,8aα-decahydronaphtha-len-5-one dissolved in 3 mL of benzene. After heat-treating further for 22 hours, the reaction mixture was cooled and diluted by stirring fast while sequentially adding 10 mL of ether and 3 mL of $H_2O$. After phase separation was completed, the organic phase was washed with 2 mL of $H_2O$ and 3 mL of saturated brine and then dried ($MgSO_4$). An almost colorless oil obtained by concentrating under reduced pressure was separated by silica gel column (10×2.5 cm) chromatography using 5% EtOAc (in hexane) as an eluent to obtain a compound of Preparation Example 23 (180 mg, 85%).

The obtained Preparation Example 23 compound had the following physicochemical properties and was identified as (−)-(1R,4aS,8aS)-1β,2β,4β,-trimethyl-1α[(2',5'-dimethoxy-phenyl)methyl]-5-exo-methylene-(3H)-1,4,4a,5,6,7,8,8aα-octahydronaphthalene'.

$[\alpha]^{25}_D$−40.4° (c 0.5, $CH_2Cl_2$).

m.p.: 77-78° C.

Silica gel TLC $R_f$ 0.70 (15% EtOAc in hexane).

$^1$H NMR ($CDCl_3$) δ 0.86 (s, 3H), 1.01 (d, 3H, J=5.5 Hz), 1.07 (s, 3H), 1.15-1.65 (m, 7H), 1.70-1.95 (m, 2H), 2.05-2.15 (m, 2H), 2.20-2.45 (m, 1H), 2.64 (AB q, 2H, J=14 Hz), 3.72 (s, 3H), 3.75 (s, 3H), 4.33-4.47 (m, 2H), 6.65-6.77 (m, 3H).

Anal calcd for $C_{23}H_{34}O_2$: C, 80.65; H, 10.00. found: C, 80.82; H, 10.04.

<Preparation Example 24> Preparation of dimethyl ether of 2-[[(1R,2S,4aS,8aS)-1,2,4a,5-tetramethyl-2,3,4,7,8,8a-hexahydronaphthalen-1-yl]methyl]benzene-1,4-diol The compound of Preparation Example 23 (108.5 mg, 0.317 mmol) and rhodium trichloride hydrate (16.7 mg, 0.06 mmol, 20 mol %) were added to 11 mL of EtOH solution and the prepared mixture was heated under reflux. After heat-treating for 20 hours, the reaction mixture was cooled and quenched by adding 5 mL of $H_2O$. The aqueous phase was extracted three times with 10 mL of $CH_2Cl_2$ and the extract was combined, dried ($MgSO_4$) and concentrated to obtain a faintly colored oil. The residue was purified with a silica gel (10% EtOAc in hexane) plug and concentrated to obtain a clear colorless oil. Then, a compound of Preparation Example 24 was obtained by slowly solidifying the same under a high-pressure condition. The obtained Preparation Example 24 compound had the following physicochemical properties and was identified as 'dimethyl ether of 2-[[(1R,2S,4aS,8aS)-1,2,4a,5-tetramethyl-2,3,4,7,8,8a-hexahydronaphthalen-1-yl]methyl]benzene-1,4-diol'.

$[\alpha]^{25}_D$+8.88° (c 0.18, $CH_2C_{12}$).

m.p.: 63-68° C.

Silica gel TLC $R_f$ 0.71 (15% EtOAc in hexane), 0.37 (5% EtOAc in hexane).

$^1$H NMR (CDCl$_3$) δ 0.75-1.15 (m, 4H), 0.87 (s, 3H), 1.01 (s, 3H), 1.24-1.65 (m, 9H), 2.0-2.15 (br m, 3H), 2.70 (br s, 2H), 3.72 (s, 3H), 3.75 (s, 3H), 5.15 (br s, 1H), 6.65-6.85 (m, 3H).

Mass spectrum (chemical ionization, negative ion), m/z 341 (M−1)$^−$.

<Preparation Example 25> Preparation of 2-[[(1R,2S,4aS,8aS)-1,2,4a,5-tetramethyl-2,3,4,7,8,8a-hexahydronaphthalen-1-yl]methyl]cyclohexa-2,5-diene-1,4-dione A solution obtained by adding the compound of Preparation Example 24 (70.0 mg, 0.204 mmol) to 3.5 mL of THF was added dropwise to 448 mg (0.82 mmol) of a ceric ammonium nitrate solution (in 3.5 mL of H$_2$O) under stirring. 15 minutes later, the reaction mixture was diluted sequentially with 3 mL of saturated brine and 10 mL of ethyl ether. After phase separation was completed, the aqueous phase fraction was extracted three times with 10 mL of CH$_2$C$_{12}$. The extracted solution was combined, dried (MgSO$_4$), concentrated and purified by silica gel column (15×2 cm) chromatography to obtain an orange oil. It was eluted with 5% EtOAc (in hexane) to obtain a compound of Preparation Example 25 (25 mg, 40%). The obtained compound had the following physicochemical properties and was identified as '2-[[(1R,2S,4aS,8aS)-1,2,4a,5-tetramethyl-2,3,4,7,8,8a-hexahydronaphthalen-1-yl]methyl]cyclohexa-2,5-diene-1,4-dione'.

$[\alpha]^{25}_D$+21° (c 0.02, CH$_2$C$_{12}$).

Silica gel TLC $R_f$ 0.55 (15% EtOAc in hexane); $\lambda_{max}$ (CH$_3$OH) 292 nm.

$^1$H NMR (CDCl$_3$) δ 0.80-2.15 (m, 5H), 0.85 (s, 3H), 0.93 (d, 3H, J=6.5 Hz), 1.00 (s, 3H), 1.53 (br s, 1H), 2.45-2.67 (AB q, 2H, J=13.5 Hz), 5.14 (br s, 1H), 6.51 (br s, 1H), 6.71 (m, 2H).

Mass spectrum (chemical ionization) m/z 312 [M+1]$^+$; mass spectrum (electron impact), m/z 311.199 (C$_{21}$H$_{27}$O$_2$ requires 311.201).

<Preparation Example 26> Preparation of 2-[[(1R,2S,4aS,8aS)-1,2,4a,5-tetramethyl-2,3,4,7,8,8a-hexahydronaphthalen-1-yl]methyl]benzene-1,4-diol 25 mg (0.08 mmol) of the compound of Preparation Example 25 was dissolved in 2 mL of ethyl ether and a Na$_2$S$_2$O$_4$ solution (56 mg Na$_2$S$_2$O$_4$ in 2 mL of H$_2$O, 0.32 mol) was added dropwise to the resulting solution under vigorous stirring. 45 minutes later, the reaction mixture was diluted with 2 mL of saturated brine and 10 mL of ethyl ether. After phase separation was completed, the extracted aqueous phase fraction was further extracted three times with 10 mL of ethyl ether. The extracted ether solution was combined, dried (Na$_2$SO$_4$), concentrated and purified by silica gel column (18×1 cm) chromatography to obtain an oily residue. It was eluted with a 15% EtOAc (in hexane) solution to obtain a clear colorless oil. The oil was solidified in vacuo to obtain a compound of Preparation Example 26 (23 mg, 92%). The obtained compound had the following physicochemical properties and was identified as '2-[[(1R,2S,4aS,8aS)-1,2,4a,5-tetramethyl-2,3,4,7,8,8a-hexahydronaphthalen-1-yl]methyl]benzene-1,4-diol'.

(+)-1: $[\alpha]^{25}_D$+22.0° (c 1.35, CDCl$_3$).

(−)-1: $[\alpha]^{25}_D$−19.5° (c 1.0, CKCl$_3$).

m.p.: 125-127° C.

Silica gel TLC $R_f$ 0.10 (15% EtOAc in hexane); $\lambda_{max}$ (DMSO) 305 nm.

$^1$H NMR (CDCl$_3$) δ 0.86 (s, 3H), 0.99 (d, 3H, J=8 Hz), 1.02 (s, 3H), 1.51 (br s, 3H), 1.2-1.65 (m, 7H), 1.9-2.15 (m, 3H), 2.54-2.70 (AB q, 2H, J=14 HZ), 4.38 (br s, 1H), 4.41 (br s, 1H), 5.14 (br s, 1H) and 6.59 (m, 3H); mass spectrum (chemical ionization), m/z 315 [M+1]$^+$.

Mass spectrum (electron impact), m/z 314.225 [M]$^+$ (C$_{21}$H$_{30}$O$_2$ requires 314.225).

<Preparation Example 27> Preparation of 2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien1-yl]amino]acetic Acid The compound of Preparation Example 10 (3.0 mg, 8.4 μmol) and glycine (0.8 mg, 10 μmol) were added to EtOH (1 mL) and stirred for 24 hours at room temperature in the presence of NaHCO$_3$ (11 mg, 130 μmol). A residue prepared through filtration and evaporation was subjected to C$_{18}$ reversed-phase HPLC (YMC-Pack AM-323, 1.0×25 cm; flow rate 2.5 mL/min; UV detection at 300 nm; eluent CH$_3$CN/H$_2$O/CF$_3$CO$_2$H, 85:15:0.1) to obtain a compound of Preparation Example 27 (1.6 mg, 47%).

The obtained Preparation Example 27 compound had the following physicochemical properties and was identified as '2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien-1-yl]amino]acetic acid'.

m.p.: 156-158° C.

$[\alpha]^{20}_D$−71.7° (C 1.0, MeOH).

IR (KBr) v$_{max}$ 3300, 1720, 1640, 1580, 1370, 1200 cm$^1$.

UV (MeOH) $\lambda_{max}$ 317 (c 11800) and 488 nm (860).

ELMS m/z (%) 401 (M$^+$, 1). 385(1), 357(4), 343(3), 211(20), 191(25) and 95(100).

FABMS (positive) m/z 404 [M+2H+H]$^+$; HRFABMS m/z 404.2461 [M+2H+H]$^+$, calcd for C$_{23}$H$_{34}$NO$_5$, 404.2437.

NMR (CD$_3$OD): see [Table 16].

$^{13}$C NMR (CD$_3$OD): see [Table 16].

TABLE 16

| position | $^1$H$^a$ | J(Hz) | $^{13}$C$^a$ | | H coupled with C$^b$ |
|---|---|---|---|---|---|
| 1 | 2.10 m | | 21.1 | t | |
|   | 1.44 m | | | | |
| 2 | 1.93$^c$ m | | 28.0 | t | H-10 |
| 3 | 5.08 brs | | 121.9 | d | H-11 |
| 4 | | | 144.9 | s | H-11, H-12 |
| 5 | | | 39.6 | s | H-10, H-11, H-12 |
| 6 | 1.63 m | | 37.4 | t | H-12 |
|   | 1.03 m | | | | |
| 7 | 1.36$^c$ m | | 29.2 | t | H-13 |
| 8 | 1.32 m | | 39.0 | d | H-10, H-14, H-15 |
| 9 | | | 43.6 | s | H-10, H-13, H-14, H-15 |
| 10 | 1.10 m | | 49.9 | d | H-12, H-14, H-15 |
| 11 | 1.50 s | | 18.4 | q | |
| 12 | 1.00 s | | 20.7 | q | H-10 |
| 13 | 0.97 d | 7.0 | 18.4 | q | |
| 14 | 0.82 s | | 17.8 | q | H-10, H-15 |
| 15 | 2.57 d | 13.6 | 33.3 | t | H-14 |
|   | 2.42 d | 13.6 | | | |
| 16 | | | 115.9 | s | H-15 |

TABLE 16-continued

| position | $^1H^a$ | J(Hz) | $^{13}C^a$ | | H coupled with $C^b$ |
|---|---|---|---|---|---|
| 17 | | | 159.6 | s | H-15, H-19 |
| 18 | | | 180.8 | s | |
| 19 | 5.28 | s | 93.8 | d | |
| 20 | | | 151.5 | s | H-22 |
| 21 | | | 184.0 | s | H-15, H-19 |
| 22 | 3.96 | s | 44.9 | t | |
| 23 | | | 171.9 | s | H-22 |

$^a$δ in ppm
$^b$HMBC correlations
$^c$2H

<Preparation Example 28> Preparation of (2S)-2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien1-yl]amino]-3-hydroxypropanoic Acid The compound of Preparation Example 10 (3.0 mg, 8.4 μmol) and L-serine (1.3 mg, 10 pmol) were added to EtOH (1 mL) and stirred for 24 hours at 40° C. in the presence of NaHCO₃ (27 mg, 34 μmol). A residue prepared through filtration and evaporation was subjected to $C_{18}$ reversed-phase HPLC (YMC-Pack AM-323, 1.0×25 cm; flow rate 2.5 mL/min; UV detection at 300 nm; eluent $CH_3CN/H_2O/CF_3CO_2H$, 85:15:0.1) to obtain a compound of Preparation Example 28 (1.7 mg, 46%).

The obtained Preparation Example 28 compound had the following physicochemical properties and was identified as '(2S)-2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien-1-yl]amino]-3-hydroxypropanoic acid'.

m.p.: 198-200° C.
$[\alpha]^{17}_D$ −71° (c 0.73, EtOH).
IR (K Br) $\nu_{max}$ 3400, 1670, 1630, 1590, 1540, 1380, 1200 cm$^{-1}$.
UV (MeOH) $\lambda_{max}$ 321 (c 12100) and 498 nm (920).
FABMS (negative, diethanolamine matrix) m/z 432 [M+2H−H]⁻.
HRFABMS m/z 432.2381 [M+2H−H]⁻, calcd for $C_{24}H_{34}NO_6$ 432.2386.
$^1$HNMR (DMSO-d₆): see [Table 17].
$^{13}$C NMR (DMSO-d₆): see [Table 17].

TABLE 17

| position | $^1H^a$ | J(Hz) | $^{13}C^a$ | | H coupled with $C^b$ |
|---|---|---|---|---|---|
| 1 | 2.01 | m | 18.9 | t | H-10 |
|   | 1.39 | m | | | H-10 |
| 2 | 1.92$^c$ | m | 25.8 | t | |
| 3 | 5.05 | brs | 121.0 | d | H₃-11 |
| 4 | | | 142.8 | s | H₃-11, H₃-12 |
| 5 | | | 37.2 | s | H-3, H₃-11, H₃-12 |
| 6 | 1.53 | m | 34.9 | t | H₃-12 |
|   | 0.98 | m | | | |
| 7 | 1.33$^c$ | m | 26.9 | t | H₃-13 |
| 8 | 1.30 | m | 36.8 | d | H-6, H-10, H₃-14, H₂-15 |
| 9 | | | 41.2 | s | H-10, H₃-13, H₃-14, H₂-15 |
| 10 | 1.02 | m | 46.5 | d | H₃-12, H₃-14, H₂-15 |
| 11 | 1.48 | s | 17.5 | q | H-3 |
| 12 | 0.93 | s | 19.3 | q | |
| 13 | 0.90 | d | 7.0 | 17.2 q | |
| 14 | 0.78 | s | | 16.5 q | H-10, H₂-15 |
| 15 | 2.43 | d | 13.6 | 31.4 t | H₃-14 |
|   | 2.32 | d | 13.6 | | |

TABLE 17-continued

| position | $^1H^a$ | J(Hz) | $^{13}C^a$ | | H coupled with $C^b$ |
|---|---|---|---|---|---|
| 16 | | | 113.5 | s | H₂-15 |
| 17 | | | 158.5 | s | H₂-15, H-19 |
| 18 | | | 178.8 | s | H-19, NH-20 |
| 19 | 5.35 | s | 93.1 | d | NH-20 |
| 20 | | | 147.1 | s | |
| 20-NH | 7.15 | d | 8.0 | | |
| 21 | | | 182.0 | s | H₂-15, H-19, NH-20 |
| 22 | 4.20 | m | 56.5 | d | |
| 23 | | | 171.9 | s | H₂-24 |
| 24 | 3.78 | dd | 11.4, 2.9 | 59.8 t | |
|   | 3.82 | dd | 11.4, 2.9 | | |

$^a$δ in ppm
$^b$HMBC correlations
$^c$2H

<Preparation Example 29> Preparation of (2S)-2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien1-yl]amino]-3-hydroxybutanoic acid The compound of Preparation Example 10 (3.0 mg, 8.4 μmol) and L-threonine (1.3 mg, 13 μmol) were added to EtOH (1 mL) and stirred for 24 hours at 40° C. in the presence of NaHCO₃ (11 mg, 130 μmol). A residue prepared through filtration and evaporation was subjected to $C_{18}$ reversed-phase HPLC (YMC-Pack AM-323, 1.0×25 cm; flow rate 2.5 mL/min; UV detection at 300 nm; eluent $CH_3CN/H_2O/CF_3CO_2H$, 85:15:0.1) to obtain a compound of Preparation Example 29 (1.3 mg, 35%).

The obtained Preparation Example 29 compound had the following physicochemical properties and was identified as '(2S)-2-[[5-[[(1R,2S,4aS,8aS)-1,2,4a,5-tetramethyl-2,3,4,7,8,8a-hexahydronaphthalen-1-yl]methyl]-6-hydroxy-3,4-dioxocyclohexa-1,5-dien-1-yl]amino]-3-hydroxybutanoic acid'.

m.p.: 188-191° C.
$[\alpha]^{17}_D$ −183° (c 1.0, EtOH).
IR (K Br) $\nu_{max}$ 3400, 1670, 1630, 1590, 1540, 1380, 1200 cm$^{-1}$.
UV (MeOH) $\lambda_{max}$ 317 (c 12600) and 490 nm (1000).
FABMS (negative, diethanolamine matrix) m/z 446 [M+2H+H]⁻.
HRFABMS m/z 446.2524 [M+2H−H]⁻, calcd for $C_{25}H_{36}NO_6$, 446.2906.
$^1$HNMR (DMSO-d₆): see [Table 18].
$^{13}$C NMR (DMSO-d₆): see [Table 18].

TABLE 18

| position | $^1H^a$ | J(Hz) | $^{13}C^a$ | | H coupled with $C^b$ |
|---|---|---|---|---|---|
| 1 | 1.99 | m | 19.9 | t | H-10 |
|   | 1.35 | m | | | H-10 |
| 2 | 1.88$^c$ | m | 26.2 | t | |
| 3 | 5.05 | brs | 120.5 | d | H₃-11 |
| 4 | | | 143.5 | s | H₃-11, H₃-12 |
| 5 | | | 37.5 | s | H-3, H₃-11, H₃-12 |
| 6 | 1.56 | m | 35.7 | t | H₃-12 |
|   | 0.95 | m | | | |
| 7 | 1.28$^c$ | m | 28.5 | t | H₃-13 |
| 8 | 1.25 | m | 37.2 | d | H-10, H₃-13, H₃-14, H₂-15 |
| 9 | | | 41.9 | s | H 10, H₃ 13, H₃ 14, H₂ 15 |
| 10 | 0.98 | m | 46.9 | d | H₃-12, H₃-14, H₂-15 |
| 11 | 1.48 | s | 17.9 | q | H-3, |
| 12 | 0.94 | s | 20.0 | q | |
| 13 | 0.92 | d | 7.0 | 18.0 q | |

TABLE 18-continued

| position | $^1H^a$ | J(Hz) | $^{13}C^a$ | H coupled with $C^b$ |
|---|---|---|---|---|
| 14 | 0.78 s | | 17.1 q | H-10 |
| 15 | 2.47 d | 13.7 | 31.7 t | $H_3$-14 |
| | 2.32 d | 13.7 | | |
| 16 | | | 114.1 s | $H_2$-15 |
| 17 | | | 158.1 s | $H_2$-15 |
| 18 | | | 179.1 s | H-19 |
| 19 | 5.33 s | | 93.0 d | |
| 20 | | | 149.5 s | |
| 20-NH | 6.95 brd | 7.0 | | |
| 21 | | | 183.1 s | $H_2$-15, H-19 |
| 22 | 4.07 m | | 60.2 d | NH-20, $H_3$-25 |
| 23 | | | 171.0 s | |
| 24 | 4.27 m | | 66.5 d | H-22 |
| 25 | 1.09 d | 7.0 | 20.8 q | |

$^a$δ in ppm
$^b$HMBC correlations
$^c$2H

<Preparation Example 30> Preparation of 18-methoxy-22,22-dimethyl-16-[{(5R,8S,9R,10S)-5,8,9-trimethyl-4-methylenedecahydronaphthalen-9-yl}methyl]benzo[d]-oxazol-17(2H)-one

*Smenospongia aurea* and *Smenospongia cerebriformis* were homogenized and incubated with *Verongula rigida* in ethanol for a week. A dried ethanol extract (3.6 kg) of the mixture of the three sponge species was subjected to silica gel VLC (36 kg, 14 (H)×17.5 (D) cm) and eluted sequentially with hexane (100%), hexane-acetone (80:20, 60:40, 50:50, 40:60, 20:80), acetone (100%), acetone-MeOH (80:20, 60:40, 50:50), MeOH (100%), MeOH—$H_2O$ (50:50) and $H_2O$ (100%) to obtain 13 fractions (Fr. 1-13). The fraction 10 (39.3 g) was fractionated further with hexane-acetone mixtures (95:5, 90:10, 85:15, 80:20), MeOH (100%) and MeOH—$H_2O$ (50:50) using a silica gel VLC (12 (H)×17.5 (D) cm) into 9 fractions (Fr. 10-1 to 10-9). The fraction 10-7 (3.7 g) was subjected to $C_{18}$ MPLC (15.5×4 cm) under an isocratic condition of MeOH—$H_2O$ (85:15) to prepare 6 subfractions (Fr. 10-7-1 to 10-7-6). The fraction 10-7-3 (115.8 mg) was subjected to $C_{18}$ HPLC (250×21.20 mm, 10 µm) chromatography using MeOH—$H_2O$ (83:17) to prepare 3 fractions (Fr. 10-7-3-1 to 10-7-3-3). The fraction 10-7-3-2 (12.4 mg) was subjected to $C_{18}$ HPLC (250×4.60 mm and 150×4.60 mm, 5 µm, connected in line) using MeOH—$H_2O$ (75:25) to obtain a compound of Preparation Example 30 and an epimer mixture thereof.

The obtained substance had the following physicochemical properties and was identified as '18-methoxy-22,22-dimethyl-16-[{(5R,8 S,9R,10S)-5,8,9-trimethyl-4-methylenedecahydronaphthalen-9-yl}methyl]benzo[d]-oxazol-17(2H)-one'.

Yellow, amorphous solid.
$[α]^{25}_D$+21 (c 0.1, MeOH).
UV (MeOH) $λ_{max}$ 297 nm.
$^1$H NMR (150 MHz, $CDCl_3$): see [Table 19].
$^{13}$C NMR (150 MHz, $CDCl_3$): see [Table 19].
HRFABMS m/z 398.2696 [M+H]$^+$ (calcd for $C_{25}H_{36}NO_3$, 398.2695), 420.2509 [M+Na]$^+$ (calcd for $C_{25}H_{35}NO_3Na$, 420.2515).

TABLE 19

| position | $δ_H$, mult. (J in Hz) | $δ_C$ |
|---|---|---|
| 1 ax | 1.42, m | 23 |
| eq | 2.13, m | |
| 2 ax | 1.20, m | 28.8 |
| eq | 1.84, m | |
| 3 ax | 2.29, dt (14, 5.2) | 33.2 |
| eq | 2.04, m | |
| 4 | | 161 |
| 5 | | 40.5 |
| 6 ax | 1.30, m | 36.9 |
| eq | 1.47, m | |
| 7 ax | 1.36, m | 28.1 |
| eq | | |
| 8 | 1.22, m | 38.1 |
| 9 | | 42.9 |
| 10 | 0.80, m | 50 |
| 11 a | 4.40, br s | 102.4 |
| b | 4.38, br s | |
| 12 | 1.01, s | 20.7 |
| 13 | 0.97, d (6.6) | 18 |
| 14 | 0.81, s | 17.5 |
| 15 | 2.37, d(14) | 32.7 |
| | 2.53, d(14) | |
| 16 | | 110.3 |
| 17 | | 181.6 |
| 18 | | 158.9 |
| 19 | 6.14, s | 96.9 |
| 20 | | 155.6 |
| 21 | | 161.4 |
| 22 | | 116.2 |
| 23 | 1.58, s | 25.9 |
| 24 | 1.60, s | 26 |
| OH | | |
| $OCH_3$ | 3.83, s | 56.4 |

<Preparation Example 31> Preparation of 18-methoxy-22-methyl-16-[{(5S,8S,9R,10S)-5,8,9-trimethyl-4-methylenedecahydronaphthalen-9-yl}methyl]benzo[d]-oxazol-17-ol During the procedure of Preparation Example 30, the fraction 10-7-3-3 (9.7 mg) was subjected to $C_{18}$ HPLC (250×4.60 mm and 150×4.60 mm, 5 µm, connected in line) using MeOH—$H_2O$ (78:22) and then to $C_{18}$ HPLC (250× 4.60 mm, 5 µm) for 120 minutes with varying concentrations of MeOH—$H_2O$ (80:20→100:0) to obtain a compound of Preparation Example 31 (1.8 mg).

The obtained compound (Preparation Example 31) had the following physicochemical properties and was identified as '18-methoxy-22-methyl-16-[{(5S,8S,9R,10S)-5,8,9-trimethyl-4-methylenedecahydronaphthalen-9-yl}methyl]benzo[d]-oxazol-17-ol'.

White, amorphous solid.
$[α]^{25}_D$−29 (c 0.1, MeOH).
UV (MeOH) $λ_{max}$ 295 nm.
$^1$H NMR (150 MHz, $CDCl_3$): see [Table 20].
$^{13}$C NMR (150 MHz, $CDCl_3$): see [Table 20].
HRFABMS m/z 384.2540 [M+H]$^+$ (calcd for $C_{24}H_{34}NO_3$, 384.2539), 406.2357 [M+Na]$^+$ (calcd for $C_{24}H_{33}NO_3Na$, 406.2358).

TABLE 20

| position | $δ_H$, mult. (J in Hz) | $δ_C$ |
|---|---|---|
| 1 ax | 1.51, m | 23.4 |
| eq | 2.27, m | |
| 2 ax | 1.22, m | 28.9 |
| eq | 1.87, m | |

TABLE 20-continued

| position | | δ$_H$, mult. (J in Hz) | δ$_C$ |
|---|---|---|---|
| 3 | ax | 2.33, t (7.5) | 33.2 |
| | eq | 2.02, m | |
| 4 | | | 160.5 |
| 5 | | | 40.6 |
| 6 | ax | 1.19, m | 36.5 |
| | eq | 1.43, m | |
| 7 | ax | 1.39, m | 28.2 |
| | eq | | |
| 8 | | 1.40, m | 37.4 |
| 9 | | | 43.1 |
| 10 | | 0.92, m | 49.4 |
| 11 | a | 4.36, br s | 102.7 |
| | b | 4.32, br s | |
| 12 | | 1.04, s | 20.7 |
| 13 | | 1.04, d | 18.5 |
| 14 | | 0.91, s | 17.7 |
| 15 | | 2.80, d(14) | 34.6 |
| | | 2.89, d(14) | |
| 16 | | | 109.2 |
| 17 | | | 143.7 |
| 18 | | | 144.6 |
| 19 | | 6.98, s | 98.8 |
| 20 | | | 132.3 |
| 21 | | | 146.6 |
| 22 | | | 162 |
| 23 | | 2.54, s | 14.6 |
| 24 | | | |
| OH | | 5.87, s | |
| OCH$_3$ | | 3.90, s | 56.6 |

<Preparation Example 32> Preparation of 3-[[(1R, 2S,4aS,8aS)-1,2,4a-trimethyl-5-methylidene-3,4,6,7,8,8a-hexahydro-2H-naphthalen-1-yl]methyl]-4-hydroxy-5-(2-phenylethylamino)cyclohexa-3,5-diene-1,2-dione After preparing subfractions Fr. 10-7-1 to 10-7-6 according to the same method as in Preparation Example 30, Fr. 10-7-4 (53 mg) was subjected to C$_{18}$ HPLC (25×2.1 cm, 10 μm) repeatedly under an isocratic condition of MeOH—H$_2$O (87:13) to obtain a compound of Preparation Example 32 (t$_R$=113 min).

The obtained compound had the following physicochemical properties and was identified as '3-[[(1R,2S,4aS,8aS)-1,2,4a-trimethyl-5-methylidene-3,4,6,7,8,8a-hexahydro-2H-naphthalen-1-yl]methyl]-4-hydroxy-5-(2-phenylethylamino)cyclohexa-3,5-diene-1,2-dione'.

$C_{29}H_{37}NO_3$.

m.p.: 168-170° C.

SM m/e (%): 447 (7), 257 (64), 191 (11), 166 (59), 152 (25), 135 (16), 121 (23), 109 (23), 107 (20), 95 (100).

m/e 166.0495. calc. 166.0504 for $C_8H_8NO_3$; m/e 191.1795. calc. 191.1799 for $C_{14}H_{23}$; m/e 257.104. calc. 257.105 for $C_{15}H_{15}NO_3$.

IR (KBr) ν cm$^{-1}$: 3265, 1600, 1395.

$^1$H NMR (CDCl$_3$, 250 MHz) δ ppm: 6.47 (1H exch., s), 5.41 (1H, s), 4.45 (2H, br s), 3.43 (2H, q), 2.87 (2H, t), 2.52-2.51 (dd, AB syst., J=14 and 2 Hz), 1.05 (3H, s), 0.98 (3H, d, J=7.5 Hz), 0.84 (3H, s), 0.79 (1H, dd, J=11.2 and 2 Hz).

$^{13}$C NMR (ppm; CDCl$_3$): see [Table 21].

TABLE 21

| Carbon | Preparation Example 32 (δ ppm) |
|---|---|
| C-1 | 22.5 |
| C-2 | 25.0 |
| C-3 | 32.8 |
| C-4 | 153.6 |
| C-5 | 39.5 |
| C-6 | 37.9 |
| C-7 | 27.9 |
| C-8 | 39.3 |
| C-9 | 44.5 |
| C-10 | 48.3 |
| C-11 | 105.7 |
| C-12 | 33.2 |
| C-13 | 18.7 |
| C-14 | 18.4 |
| C-15 | 32.0 |
| C-16 | 114.0 |
| C-17 | 157.0 |
| C-18 | 178.4 |
| C-19 | 91.9 |
| C-20 | 150.1 |
| C-21 | 182.8 |

<Preparation Example 33> Preparation of 3-[[(1R, 2S,4aS,8aS)-1,2,4a-trimethyl-5-methylidene-3,4,6,7,8,8a-hexahydro-2H-naphthalen-1-yl]methyl]-2-hydroxy-5-methoxycyclohexa-2,5-diene-1,4-dione Three sponge species *Smenospongia aurea*, *Smenospongia cerebriformis* and *Verongula rigida* were mixed and an ethanol extract was prepared by adding ethanol (98%). The ethanol extract was separated with a silica gel column using hexane, acetone, methanol, water, etc. to obtain a total of 13 fractions. Among them, fractions 4, 5, 6 and 10 were concentrated and separated by C$_{18}$ RP column chromatography using a mobile phase (methanol:water=1:1 to 3:1) to obtain a pure compound (Preparation Example 33 compound). The compound was identified by HPLC (Agilent Technologies 1260 Infinity) using a UV spectrophotometer (203 nm) and a Bluespher AB2 (150×2 mm) column. The HPLC was conducted at a flow rate of 1 mL/min and 40° C. using water-methanol (78:22) as a mobile phase and the peaks of the compound were detected at 114 minutes.

The obtained compound had the following physicochemical properties and was identified as '3-[[(1R,2S,4 aS,8aS)-1,2,4a-trimethyl-5-methylidene-3,4,6,7,8,8a-hexahydro-2H-naphthalen-1-yl]methyl]-2-hydroxy-5-methoxycyclohexa-2,5-diene-1,4-dione'.

Yellow solid.

$C_{22}H_{30}O_4$.

Molecular weight: 358.47.

m.p.: 72.5° C.

IT-TOF/MS: m/z 381.1972 [M+Na]$^+$.

$^1$H-NMR (CDCl$_3$, 600 MHz): 2.08, 1.42 (each 1H, m, H$_2$-1), 1.84, 1.16 (each 1H, m, H$_{2-2}$), 2.29, 2.05 (each 1H, ddd, J=13.7, 8.6, 5.4, H$_2$-3), 1.49, 1.32 (each 1H, m, H$_2$-6), 1.37 (2H, m, H$_2$-7), 1.14 (1H, m, H-8), 0.74 (1H, d, J=12.0, H-10), 4.43, 4.41 (each 1H, s, H$_2$-11), 1.02 (3H, s, H$_3$-12), 0.96 (3H, d, J=6.4, H$_3$-13), 0.82 (3H, s, H$_3$-14), 2.51, 2.45 (each 1H, d, J=13.7, H$_{2-15}$), 5.83 (1H, s, H-19), 3.84 (3H, s, H$_3$-22).

$^{13}$C NMR (CDCl$_3$, 150 MHz): 23.34 (C-1), 28.11 (C-2), 33.13 (C-3), 160.69 (C-4), 40.63 (C-5), 36.82 (C-6), 28.80 (C-7), 38.25 (C-8), 43.50 (C-9), 50.30 (C-10), 102.66 (C-11), 20.73 (C-12), 18.01 (C-13), 17.52 (C-14), 32.52 (C-15), 117.49 (C-16), 153.49 (C-17), 182.51 (C-18), 102.17 (C-19), 161.90 (C-20), 182.20 (C-21), 57.01 (C-22).

<Preparation Example 34> Preparation of 3-[[(1S, 2R,4aR,8aR)-1,2,4a-trimethyl-5-methylidene-3,4,6, 7,8,8a-hexahydro-2H-naphthalen-1-yl]methyl]-5-ethoxy-2-hydroxycyclohexa-2,5-diene-1,4-dione 400 mg of the compound of Preparation Example 33 was dissolved in 20 mL of ethanol in a round flask. After adding 10.5 mL of a 1 M potassium hydroxide (KOH) solution, the reaction mixture was stirred at 70° C. for an hour. After adding a 1 M hydrochloric acid solution to the stirred reaction mixture and concentrating under reduced pressure, the mixture was transferred to a separation funnel and fractionated by dissolving in ethyl acetate and distilled water. The ethyl acetate layer was combined, dehydrated with magnesium sulfate, filtered and then concentrated under reduced pressure. In order to obtain a pure reaction product, the resulting concentrate was separated by silica gel column chromatography using a mobile phase (n-hexane:ethyl acetate=10:1) to obtain the final compound (Preparation Example 34).

The obtained final compound (Preparation Example 34) had the following physicochemical properties and was identified as '3-[[(1S,2R,4aR,8aR)-1,2,4a-trimethyl-5-methylidene-3,4,6,7,8,8a-hexahydro-2H-naphthalen-1-yl]methyl]-5-ethoxy-2-hydroxycyclohexa-2,5-diene-1,4-dione'.

Yellow semi-solid.
C$_{23}$H$_{32}$O$_4$.
Molecular weight: 372.5.
IT-TOF/MS: m/z 395.2146 [M+Na]$^+$.
$^1$H NMR (CDCl$_3$, 600 MHz): 7.47 (1H, s), 5.83 (1H, s), 4.46, 4.44 (each 1H, s), 4.06 (2H, q, J=7.2 Hz), 2.50 (2H, dd, J=12, 6.0 Hz), 2.33 (1H, dt, J=12, 6.0 Hz), 2.17-1.66 (4H, m), 1.49 (3H, t, J=7.2 Hz), 1.46-1.09 (7H, m), 1.04 (3H, m), 0.98 (3H, d, J=6 Hz), 0.84 (3H, s).
$^{13}$C NMR (CDCl$_3$, 150 MHz): 182.68, 182.26, 161.19, 160.75, 153.35, 117.45, 102.63, 102.40, 66.10, 50.35, 43.45, 40.63, 38.29, 36.82, 33.14, 32.63, 28.79, 28.12, 23.32, 20.73, 18.46, 18.05, 13.97.

<Example 1> Evaluation of Wnt/β-Catenin Pathway Inhibitory Activity

It was investigated whether the prepared compounds inhibit Wnt/β-catenin for some structurally representative compounds.

<1-1> Wnt/β-Catenin Pathway Inhibitory Activity of Compounds of Preparation Examples 30 and 31

HEK293 cells (human embryonic kidney cells) and Wnt3a-secreting L cells were obtained from the ATCC (American Type Culture Collection, USA) and were cultured in DMEM (Dulbecco's modified Eagle's medium) supplemented with 10% FBS (fetal bovine serum), 120 μg/mL penicillin and 200 μg/mL streptomycin.

Wnt3a-CM (Wnt3a-conditioned medium) was prepared by culturing Wnt3a-secreting L cells in DMEM supplemented with 10% [v/v] FBS (fetal bovine serum) for 4 days and recovering the DMEM medium and sterilizing by filtering through a 0.22-μm filter. Then, after adding a fresh DMEM (supplemented with 10% [v/v] FBS) medium to the cells and culturing for 3 days, the medium was recovered by the same method and then combined with the previously prepared Wnt3a-CM.

After treating HEK293 cells with the Wnt3a-CM, the compound of Preparation Example 30 or the compound of Preparation Example 31 (10, 20 or 40 μM) for 15 hours and extracting cytoplasmic proteins from the cells, the amount of β-catenin regulating the CRT (β-catenin response transcription) of the Wnt/β-catenin pathway in the cells was investigated by western blot using a β-catenin antibody (BD Transduction Laboratories, USA) and the ECL system (Santa Cruz Biotechnology). The result is shown in FIG. 1.

As seen from the western blot result of FIG. 1, the cells treated with the Wnt3a-CM showed increased β-catenin expression in the cytoplasm but the cells treated with the Preparation Example 30 compound or the Preparation Example 31 compound of the present disclosure showed decreased level of β-catenin.

<1-2> Wnt/β-Catenin Pathway Inhibitory Activity of Preparation Example 32 Compound The Wnt/β-catenin pathway inhibitory activity of the Preparation Example 32 compound was evaluated in the same manner as in Example <1-1>. Briefly, after treating HEK293 cells with the Wnt3a-CM or the compound of Preparation Example 32 (10 or 20 μM) for 15 hours and extracting cytoplasmic proteins from the cells, the amount of β-catenin regulating the CRT (β-catenin response transcription) of the Wnt/β-catenin pathway in the cells was investigated by western blot using a β-catenin antibody (BD Transduction Laboratories, USA) and the ECL system (Santa Cruz Biotechnology). The result is shown in FIG. 2.

Figure 2:
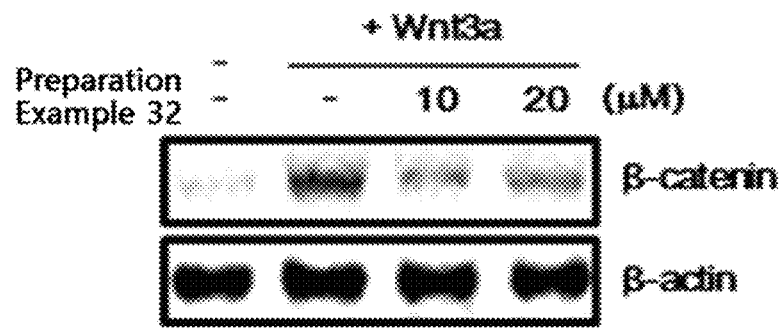
FIG. 2 shows a result of investigating the inhibitory effect of a compound of the present disclosure (Preparation Example 32) on β-catenin expression in HEK293 cells, in which the Wnt/β-catenin pathway is activated by treating with Wnt-3a CM, by western blot.

As seen from the western blot result of FIG. 2, the cells treated with the Wnt3a-CM showed increased β-catenin expression in the cytoplasm but the cells treated with the Preparation Example 32 compound of the present disclosure showed decreased level of β-catenin.

<1-3> Wnt/β-Catenin Pathway Inhibitory Activity of Preparation Example 33 and 34 Compounds ARPE-19 cells (human retinal epithelial cells) and Wnt3a-secreting L cells were obtained from the ATCC (American Type Culture Collection, USA) and were cultured in DMEM (Dulbecco's modified Eagle's medium) supplemented with 10% FBS, 120 μg/mL penicillin and 200 μg/mL streptomycin. Wnt3a-CM (Wnt3a-conditioned medium) was prepared by culturing Wnt3a-secreting L cells in DMEM supplemented with 10% [v/v] FBS (fetal bovine serum) for 4 days and recovering the DMEM medium and sterilizing by filtering through a 0.22-μm filter. Then, after adding fresh DMEM (supplemented with 10% [v/v] FBS) to the cells and culturing for 3 days, Wnt3a-CM was recovered.

After treating ARPE-19 cells with the Wnt3a-CM, the compound of Preparation Example 33 or the compound of Preparation Example 34 (3 or 6 μM) for 24 hours and extracting cytoplasmic proteins from the cells, the amount of β-catenin regulating the CRT (β-catenin response transcription) of the Wnt/β-catenin pathway in the cells was investigated by western blot using a β-catenin antibody (BD Transduction Laboratories, USA) and the ECL system (Santa Cruz Biotechnology). The result is shown in FIG. 3.

Figure 3:
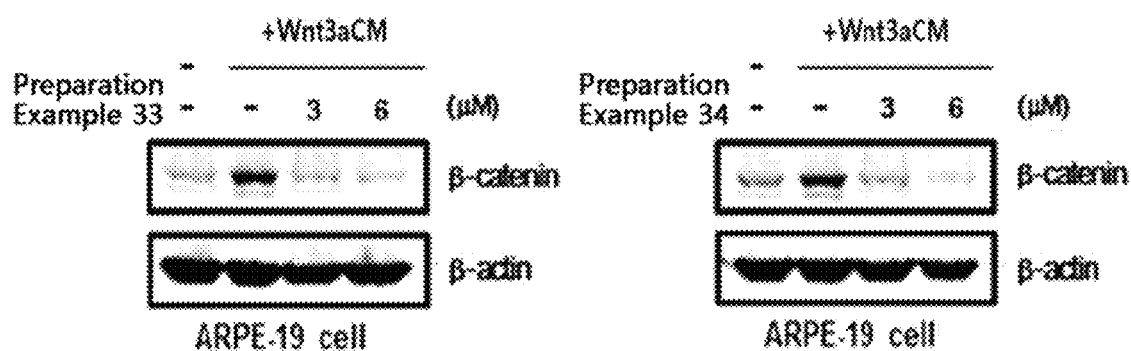
FIG. 3 shows a result of investigating the inhibitory effect of a compound of the present disclosure (Preparation Example 33 or Preparation Example 34) on β-catenin expression in human retinal epithelial cells, in which the Wnt/β-catenin pathway is activated by treating with Wnt-3a CM, by western blot.

As seen from FIG. 3, the cells treated with the Wnt3a-CM showed increased β-catenin expression in the cytoplasm but the cells treated with the Preparation Example 33 compound or Preparation Example 34 compound of the present disclosure showed decreased level of β-catenin, suggesting that the compounds inhibit the Wnt/β-catenin pathway in the human retinal epithelial cells. Meanwhile, this activity was not identified in the sponge ethanol extract used to isolate the compound of Preparation Example 33 (data not shown).

Figure 4:
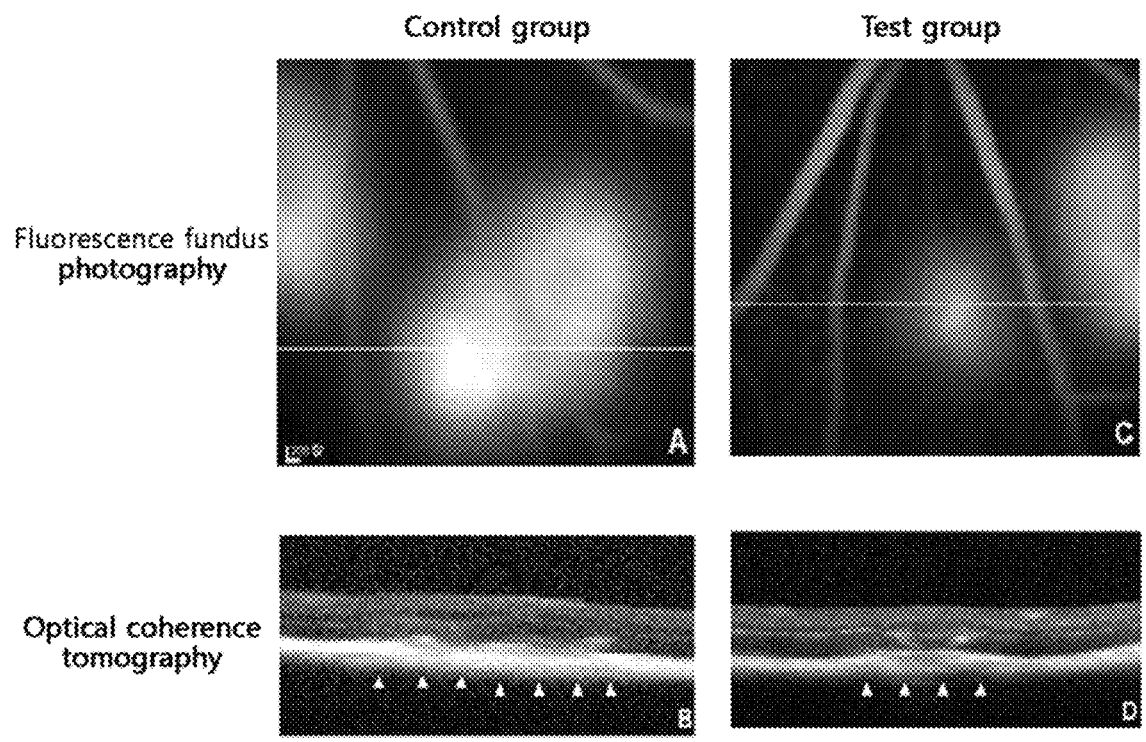
FIG. 4 shows a result of investigating the inhibitory effect of intravitreal administration of a compound of the present disclosure (Preparation Example 33) on vascular leakage in a macular edema mouse model by fluorescein angiography and optical coherence tomography (A and B are images for a control group (compound-untreated) obtained after DMSO injection and C and D are images for a test group (Preparation Example 33) obtained after injection. The arrows indicate blood vessels).

<Example 2> Evaluation of Inhibitory Activity of Vascular Leakage in the Eye <2-1> Intravitreal Administration For the compound of Preparation Example 33 which showed good activity in Example 1, the inhibitory activity on vascular leakage, which is a cause of macular degeneration or macular edema, was investigated in a macular edema-induced mouse model. Macular edema was induced in a 10-week-old $C_{57}BL/6$ mouse by irradiating a laser. After anesthetizing the mouse with ketamine (70 mg/kg) and xylazine (30 mg/kg), the pupil was dilated with 1% tropicamide. Hydroxypropylmethyl cellulose was dropped onto the eye and a microscope cover glass was used as a contact lens. Then, five laser burns were made in the space between the blood vessels around the optic disc (Zeiss 1149-630, laser power 180 mW, duration 0.1 s, spot size 50 μm). In this state, the blood vessel size and permeability were investigated by fluorescein angiography (FA) and optical coherence tomography (OCT). 24 hours after the laser irradiation, 0.5 μL of DMSO (dimethyl sulfoxide) was injected to a control group and 100 ng/0.5 μL of the Preparation Example 33 compound dissolved in DMSO was injected to a test group, into the vitreous cavity of the mouse. One week later, fluorescein angiography and optical coherence tomography were conducted again. FIG. 4 shows the images of the control group and the compound-treated group.

As seen from the fluorescein angiography and optical coherence tomography results of FIG. 4, the test group (FIG. 4, C, D) showed distinctly decreased vascular leakage, which is a cause of macular degeneration or macular edema, as compared to the control group (FIG. 4, A, B).

<2-2> Intraperitoneal Administration

After inducing macular edema in a $C_{57}BL/6$ mouse and intraperitoneally administering the compound of Preparation Example 33, vascular leakage in the retina was investigated.

Briefly, after anesthetizing an 8-to-12-week-old $C_{57}BL/6$ mouse with Zoletil (40 mg/kg) and xylazine (5 mg/kg), the pupil was dilated with 1% tropicamide. Hydroxypropylmethyl cellulose was dropped onto the eye and a microscope cover glass was used as a contact lens. Then, 3-5 laser burns were made in the space between the retinal blood vessels around the optic disc (Zeiss 1149-630, laser power 200 mW, duration 0.05 s, spot size 50 μm).

After the laser irradiation, 10 mL/kg of distilled water as a vehicle was intraperitoneally administered to a control group (FIG. 5, A) and 1 mg/kg of the compound of Preparation Example 33 (dissolved distilled water) was intraperitoneally administered to a test group (FIG. 5, B) every day for 7 days. On day 6, 10% sodium fluorescein was intraperitoneally administered and optical coherence tomography was conducted.

Figure 5:
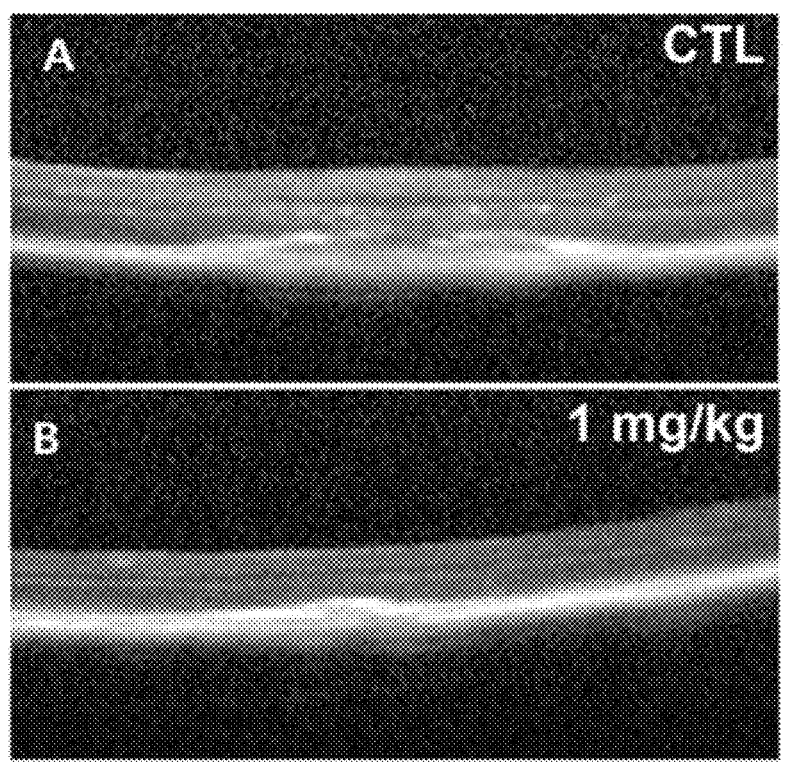
FIG. 5 shows a result of investigating the inhibitory effect of intraperitoneal injection of a compound of the present disclosure (Preparation Example 33) on vascular leakage in a macular edema mouse model by optical coherence tomography (A: vehicle-administered group, B: Preparation Example 33 compound 1 mg/kg administered group).

As seen from FIG. 5, it was confirmed that the compound of the present disclosure inhibited vascular leakage, which is a cause of macular degeneration or macular edema, even when it was injected intraperitoneally.

<Example 3> In Vivo PK (Pharmacokinetics) after Oral Administration

Male ICR mice (8 weeks, 30-35 g) were purchased from Samtako Co. (Osan, Korea). The test animals were acclimatized for a week under the following conditions: temperature 23±2° C., relative humidity 55±10%, illumination intensity 150-300 lux, ventilation frequency 15-20 times/h, illumination cycle 12 h (07:00-19:00). All the animal experiments were approved by the Animal Care and Use Committee of Kyungpook National University (Study No. 2016-0043).

The mice were fasted for 12 hours before drug administration. Feed and water were supplied ad libitum. The compound of Preparation Example 33 was dissolved in DW:PEG 400 (=60:40 (v/v)) and administered by oral gavage at a dose of 10 mg/kg.

0.5 hour and 2 hours after the oral administration, blood samples were taken from the abdominal artery. 50 mL of a plasma sample obtained after centrifuging the blood sample at 13,000 rpm for 5 minutes was stored at −80° C. until use for analysis. An eye sample taken from the mouse was homogenized with 9-fold saline to obtain a 10% cell homogenate. The obtained 50-mL aliquots were stored at −80° C. until use for analysis.

50 μL of the aliquot was added to 200 μL of an acetonitrile solution containing 0.5 ng/mL propranolol. After vortex mixing for 10 minutes, followed by centrifugation at 13,000 rpm for 10 minutes, the supernatant was transferred to a fresh tube and evaporated under nitrogen gas flow. The residue was added to 150 μL of a mobile phase and a 5-μL aliquot was injected directly into the LC-MS/MS system for analysis.

Figure 6:
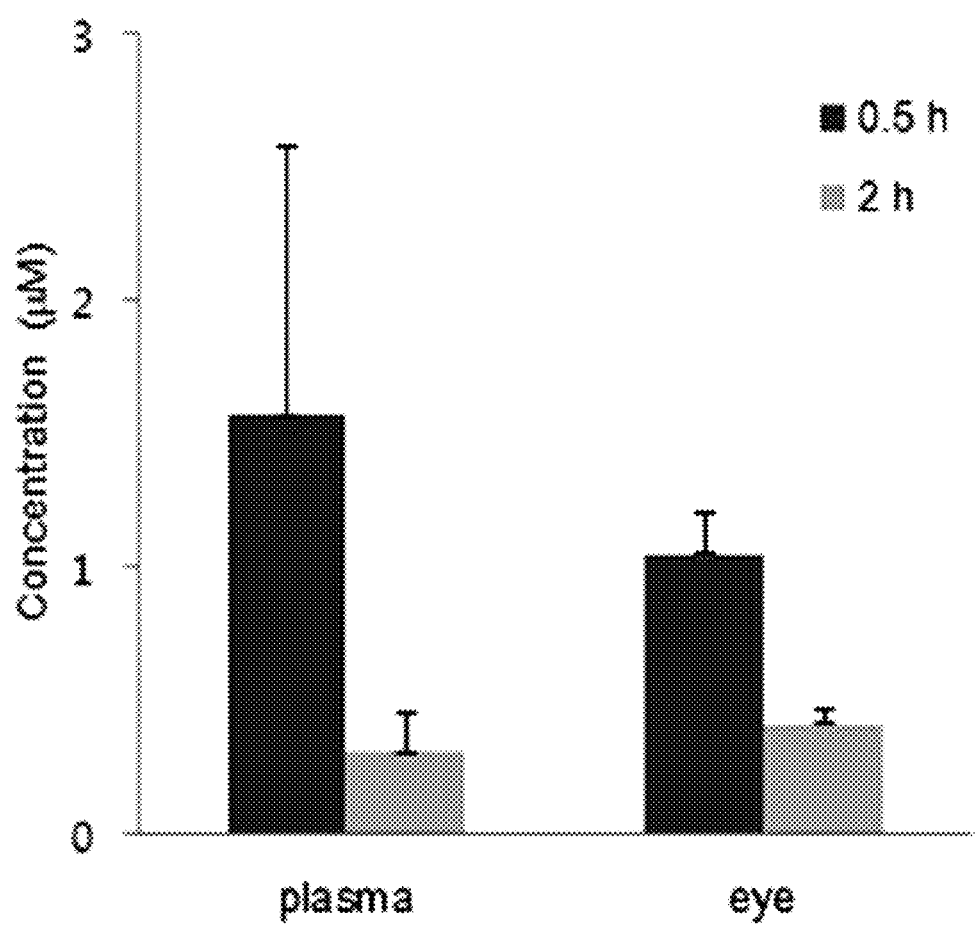
FIG. 6 shows a result of orally administering a compound of the present disclosure (Preparation Example 33) to an ICR mouse and measuring distribution of the compound in target tissues (particularly, eye).

In order to investigate the distribution of the compound of the present disclosure in the target tissue, the compound was orally administered at a dose of 10 mg/kg and the concentration of the compound in the blood plasma and eye was measured. The sampling times were determined as 0.5 hour and 2 hours based on the peak plasma concentration and the distribution phase. As seen from FIG. 6, the compound of the present disclosure (particularly, the compound of Preparation Example 33) showed high permeability for the target tissue and was found to be highly targeted in the eye even when it was administered orally. Through this result, it was confirmed that the compound of Preparation Example 33 of the present disclosure can exhibit therapeutic effect even when it is administered via different administration routes (oral administration, intraperitoneal injection, intravenous injection, etc.) other than being administered directly into the vitreous cavity. That is to say, whereas the currently available eye disease-related therapeutic agents cause inconvenience, pain and side effects because they have to be administered directly into the vitreous cavity, it was confirmed that the compound of the present disclosure can be administered orally.

<Example 4> Evaluation of Safety of Compound

<4-1> Evaluation of Acute Toxicity

This experiment was conducted to determine acute (within 24 hours) toxicity and lethality when the compound of Preparation Example 33 was administered in excessive amounts in a short period of time. 20 normal ICR mice were divided into a control group and a test group, with 10 mice per each. The control group was administered with PEG 400:Tween 80:ethanol (8:1:1, v:v:v) only and the test group was orally administered with the compound of Preparation Example 33 dissolved in PEG 400:Tween 80:ethanol (8:1:1, v:v:v). When lethality was investigated 24 hours after the administration, all the mice in the control group and the mice in the test group administered with the Preparation Example 33 compound at a dose of 2 g/kg/day survived.

<4-2> Evaluation of Tissue Toxicity

A long-term toxicity test was conducted by administering the compound of Preparation Example 33 at different doses to $C_{57}BL/6J$ mice (10 mice per group) for 8 weeks. In order to investigate the effect on different organs (tissues) of the animals, blood was taken from the animals of the test group to which the compound of Preparation Example 33 was administered and the control group to which only PEG 400:Tween 80:ethanol (8:1:1, v:v:v) was administered 8 weeks later and the level of GPT (glutamate-pyruvate transferase) and BUN (blood urea nitrogen) in the blood was measured using Select E (Vital Scientific NV, Netherlands). As a result, there was no significant difference between the control group and the test group in GPT, which is known to be related with liver toxicity, and BUN, which is known to be related with kidney toxicity. In addition, no special abnormality was observed in the liver and kidney tissues taken from the animals when they were prepared into tissue sections and observed under an optical microscope according to the common method.

<FORMULATION EXAMPLES> PREPARATION OF PHARMACEUTICAL FORMULATIONS

<Formulation Example 1> Preparation of Tablet 200 g of the compound of the present disclosure was mixed with 175.9 g of lactose, 180 g of potato starch and 32 g of colloidal silicate. After adding a 10% gelatin solution, the mixture was pulverized and passed through a 14-mesh sieve. A mixture obtained by drying the same and adding 160 g of potato starch, 50 g of talc and 5 g of magnesium stearate thereto was prepared into a tablet.

<Formulation Example 2> Preparation of Injection 1 g of the compound of the present disclosure, 0.6 g of sodium chloride and 0.1 g of ascorbic acid were dissolved in distilled water to make 100 mL. The resulting solution was put in a bottle and sterilized by heating at 20° C. for 30 minutes.

As described above, the present disclosure relates to a novel use of a sesquiterpene derivative, more particularly to a composition for preventing, improving or treating macular degeneration or macular edema caused by vascular leakage in the eye, which contains the sesquiterpene derivative compound represented by Chemical Formula 1 of the present disclosure or a pharmaceutically acceptable salt thereof as an active ingredient.

The compound of the present disclosure of Chemical Formula 1 has therapeutic effect for a disease caused by vascular leakage in the eye, such as macular edema, macular degeneration, etc., by inhibiting the vascular leakage in the eye, particularly in the retina. In addition, whereas the intraocular disease-related treating agents available in the market should be injected directly into the vitreous cavity, thus causing pain and side effects, the sesquiterpene derivative compound of the present disclosure is delivered to the target tissue (eye) via different administration routes (oral, intraperitoneal, etc.) other than the intravitreal route. Accordingly, the sesquiterpene derivative compound provides excellent therapeutic effect without being restricted by the administration routes. Accordingly, it is highly industrially applicable.

INDUSTRIAL APPLICABILITY

The compound of the present disclosure of Chemical Formula 1 has therapeutic effect for a disease caused by vascular leakage in the eye, such as macular edema, macular degeneration, etc., by inhibiting the vascular leakage in the eye, particularly in the retina. Whereas the intraocular disease-related treating agents available in the market should be injected directly into the vitreous cavity, thus causing pain and side effects, the sesquiterpene derivative compound of the present disclosure is delivered to the target tissue (eye) via different administration routes (oral, intraperitoneal, etc.) other than the intravitreal route. Accordingly, the sesquiterpene derivative compound provides excellent therapeutic effect without being restricted by the administration routes.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A method for treating macular degeneration or macular edema, comprising administering to a mammal in need thereof a pharmaceutical composition comprising a compound represented by Chemical Formula 1 or a pharmaceutically acceptable salt thereof as an active ingredient:

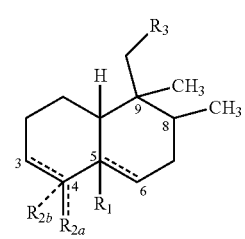

Chemical Formula 1 wherein the broken line denotes a single bond or a double bond, and wherein:
i) if the bond between C-3 and C-4 and the bond between C-5 and C-6 are single bonds, $R_{2b}$ is nonexistent and $R_{2a}$ is $CH_2$;
ii) if the bond between C-3 and C-4 is a double bond, the bond between C-5 and C-6 is a single bond, $R_{2b}$ is nonexistent and $R_{2a}$ is $CH_3$; or
iii) if the bond between C-5 and C-6 is a double bond, $R_1$ is absent and the bond between C-3 and C-4 is a single bond and $R_{2a}$ and $R_{2b}$ are $CH_3$, $R_1$ is H or $CH_3$, $R_3$ is a functional group selected from a group consisting of $R_{3a}$ through $R_{3d}$, -continued

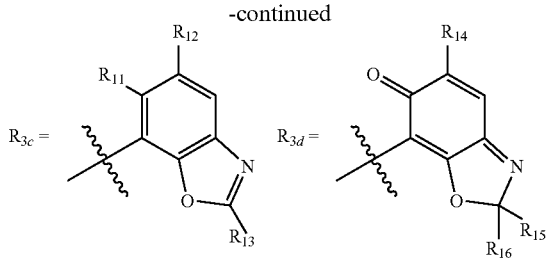

in $R_{3a}$,
  i) each of $R_4$ and $R_7$ is OH or $OCH_3$ and $R_5$, $R_6$ and $R_8$ are H; or
  ii) $R_5$ is $COOCH_3$, $R_7$ is H or OH, $R_8$ is OH and $R_4$ and $R_6$ are H, in $R_{3b}$,
  $R_9$ is a functional group selected from a group consisting of H, $NH_2$, $C_1$-$C_8$ alkoxy and $R_{9a}$ through $R_{9j}$ and $R_{10}$ is H or OH,

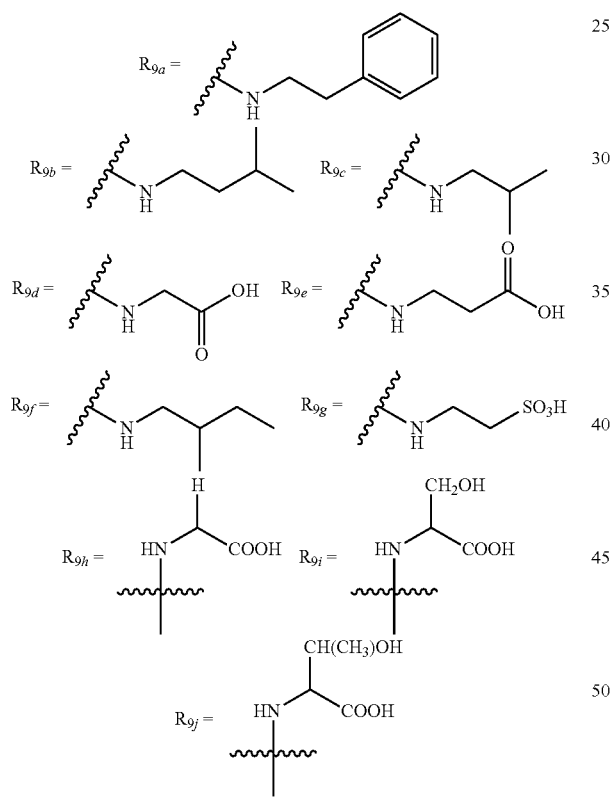

in $R_{3c}$,
  each of $R_{11}$ and $R_{12}$ is OH or OAc and $R_{13}$ is H; or
  each of $R_{11}$ and $R_{12}$ is OH or $OCH_3$ and $R_{13}$ is $CH_3$ and
in $R_{3d}$,
  $R_{14}$ is $OCH_3$ and $R_{15}$ and $R_{16}$ are $CH_3$.

2. The method according to claim 1, wherein, if the bond between C-3 and C-4 and the bond between C-5 and C-6 are single bonds, $R_{2b}$ is nonexistent, $R_{2a}$ is $CH_2$ and $R_3$ is a functional group selected from a group consisting of $R_{3b}$ through $R_{3d}$.

3. The method according to claim 2, wherein, in the functional group selected from a group consisting of $R_{3b}$ through $R_{3d}$,
  in $R_{3b}$, $R_9$ is selected from a group consisting of ethoxy, methoxy and $R_{9a}$;
  in $R_{3c}$, $R_{11}$ is OH, $R_{12}$ is $OCH_3$ and $R_{13}$ is $CH_3$; or
  in $R_{3d}$, $R_{14}$ is $OCH_3$ and $R_{15}$ and $R_{16}$ are $CH_3$.

4. The method according to claim 3, wherein the compound of Chemical Formula 1 is a compound selected from a group consisting of the compounds of Chemical Formula 31 to 35:

Chemical Formula 31

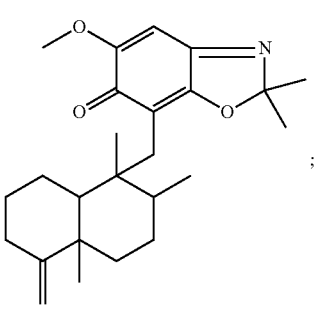

;

Chemical Formula 32

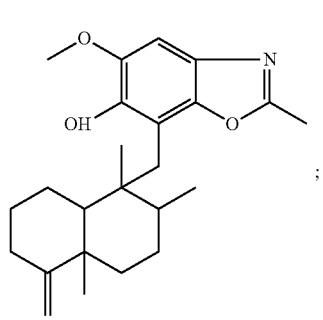

;

Chemical Formula 33

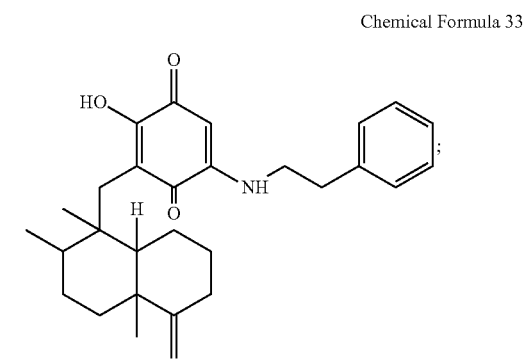

;

Chemical Formula 34

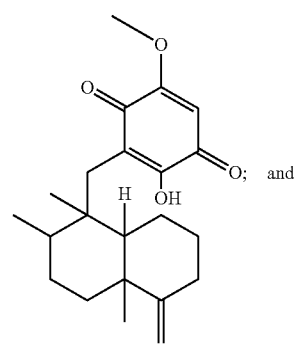

; and

-continued

Chemical Formula 35

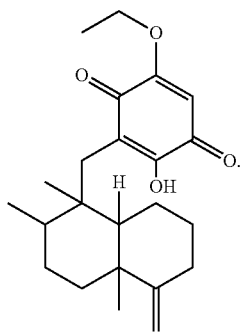

5. The method according to claim 1, wherein the composition is prepared into a formulation selected from a group consisting of an oral medication, an injection, an eye drop and an ointment.

6. A method for inhibiting vascular leakage in the eye, comprising administering to a mammal in need thereof a pharmaceutical composition comprising a compound represented by Chemical Formula 1 or a pharmaceutically acceptable salt thereof as an active ingredient:

Chemical Formula 1

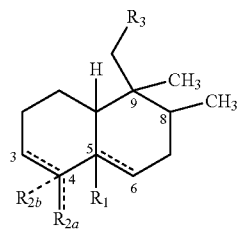

wherein the broken line denotes a single bond or a double bond, and wherein:
i) if the bond between C-3 and C-4 and the bond between C-5 and C-6 are single bonds, $R_{2b}$ is nonexistent and $R_{2a}$ is $CH_2$;
ii) if the bond between C-3 and C-4 is a double bond, the bond between C-5 and C-6 is a single bond, $R_{2b}$ is nonexistent and $R_{2a}$ is $CH_3$; or
iii) if the bond between C-5 and C-6 is a double bond, $R_1$ is absent and the bond between C-3 and C-4 is a single bond, and $R_{2a}$ and $R_{2b}$ are $CH_3$, $R_1$ is H or $CH_3$, $R_3$ is a functional group selected from a group consisting of $R_{3a}$ through $R_{3d}$,

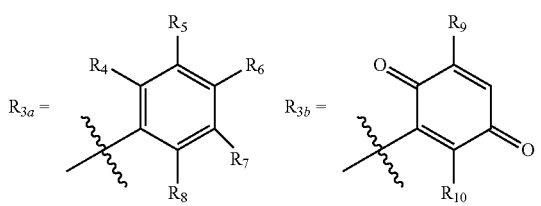

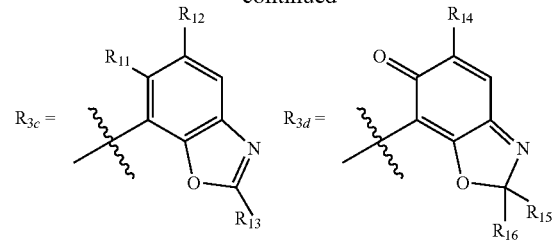

in $R_{3a}$,
i) each of $R_4$ and $R_7$ is OH or $OCH_3$ and $R_5$, $R_6$ and $R_8$ are H; or
ii) $R_5$ is $COOCH_3$, $R_7$ is H or OH, $R_5$ is OH and $R_4$ and $R_6$ are H, in $R_{2b}$,
$R_9$ is a functional group selected from a group consisting of H, $NH_2$, $C_1$-$C_8$ alkoxy and $R_{9a}$ through $R_{9j}$ and $R_{10}$ is H or OH,

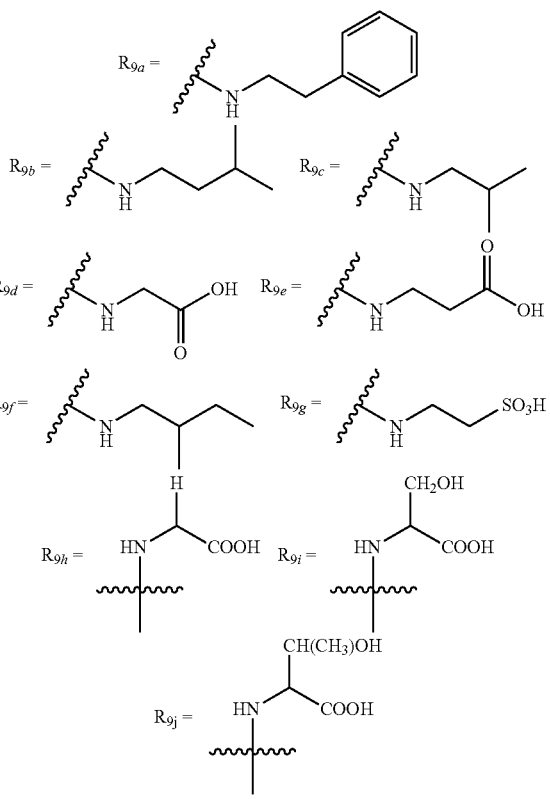

in $R_{3c}$,
each of $R_{11}$ and $R_{12}$ is OH or OAc and $R_{13}$ is H; or
each of $R_{11}$ and $R_{12}$ is OH or $OCH_3$ and $R_{13}$ is $CH_3$ and in $R_{3d}$,
$R_{14}$ is $OCH_3$ and $R_{15}$ and $R_{16}$ are $CH_3$.

7. The method according to claim 6, wherein, if the bond between C-3 and C-4 and the bond between C-5 and C-6 are single bonds, $R_{2b}$ is nonexistent, $R_{2a}$ is $CH_2$ and $R_3$ is a functional group selected from a group consisting of $R_{3b}$ through $R_{3d}$.

8. The method according to claim 7, wherein, in the functional group selected from a group consisting of $R_{3b}$ through $R_{3d}$, in $R_{3b}$, $R_9$ is selected from a group consisting of ethoxy, methoxy and $R_{9a}$;

in $R_{3c}$, $R_{11}$ is OH, $R_{12}$ is $OCH_3$ and $R_{13}$ is $CH_3$; or in $R_{3d}$, $R_{14}$ is $OCH_3$ and $R_{15}$ and $R_{16}$ are $CH_3$.

9. The method according to claim 8, wherein the compound of Chemical Formula 1 is a compound selected from a group consisting of the compounds of Chemical Formula 31 to 35:

Chemical Formula 31

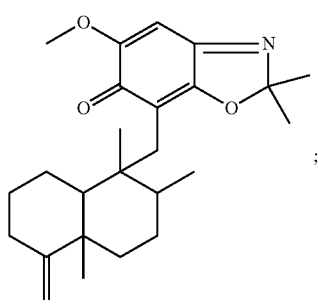

Chemical Formula 32

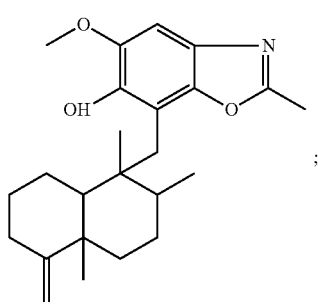

Chemical Formula 33

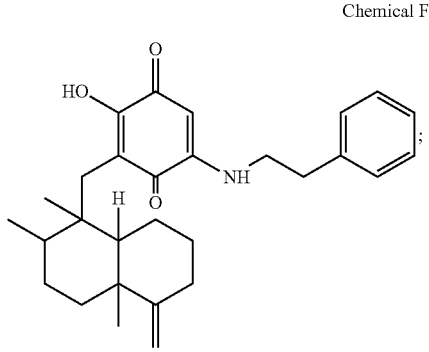

Chemical Formula 34

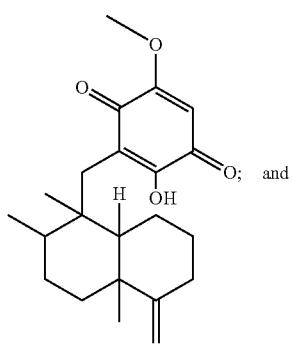

-continued

Chemical Formula 35

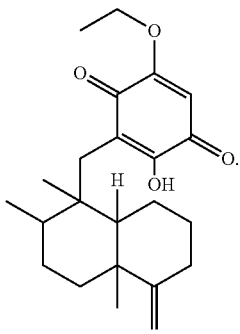

10. The method according to claim 8, wherein the compound of Chemical Formula 1 is a compound selected from a group consisting of the compounds of Chemical Formula 32 to 35:

Chemical Formula 32

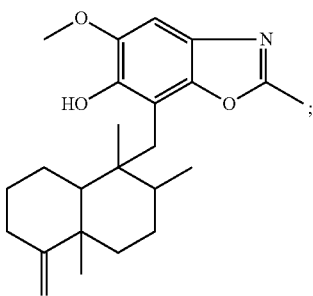

Chemical Formula 33

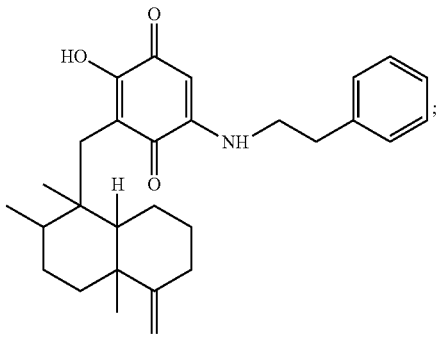

Chemical Formula 34

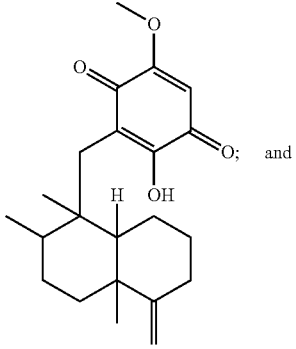

and

Chemical Formula 35

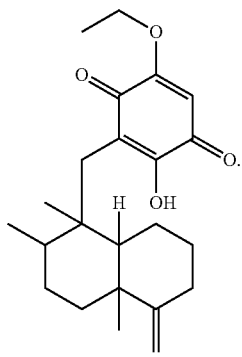

Chemical Formula 34

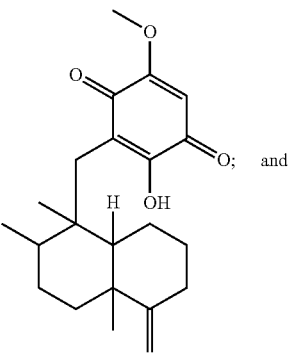
and

11. The method according to claim 3, wherein the compound of Chemical Formula 1 is a compound selected from a group consisting of the compounds of Chemical Formula 32 to 35:

Chemical Formula 32

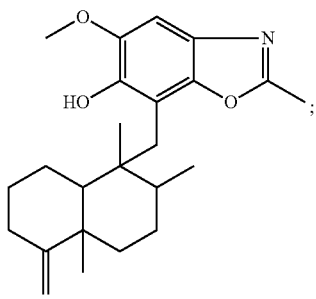

Chemical Formula 35

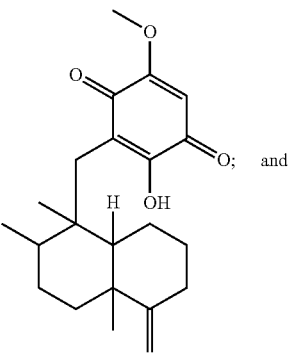

Chemical Formula 33

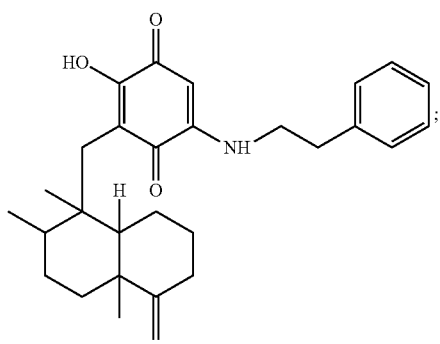

12. The method according to claim 1, wherein the bond between C-3 and C-4 and the bond between C-5 and C-6 are single bonds, $R_{2b}$ is nonexistent, and $R_{2a}$ is $CH_2$.

13. The method according to claim 1, wherein the bond between C-3 and C-4 is a double bond, the bond between C-5 and C-6 is a single bond, $R_{2b}$ is nonexistent, and $R_{2a}$ is $CH_3$.

14. The method according to claim 1, wherein the bond between C-5 and C-6 is a double bond, the bond between C-3 and C-4 is a single bond, and $R_{2a}$ is $CH_3$, and $R_{2b}$ is $CH_3$.

* * * * *